US008349574B2

(12) United States Patent
Bates et al.

(10) Patent No.: US 8,349,574 B2
(45) Date of Patent: Jan. 8, 2013

(54) METHODS OF DETERMINING PATIENT RESPONSE BY MEASUREMENT OF HER-3

(75) Inventors: Michael Bates, San Carlos, CA (US);
Ali Mukherjee, Millbrae, CA (US);
Gordon Parry, Oakland, CA (US); Jeff Sperinde, El Granada, CA (US);
Jennifer W. Cook, San Mateo, CA (US);
Gundo Diedrich, Potomac, MD (US);
Laurie Goodman, El Granada, CA (US); Stephen J. Williams, San Carlos, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 12/688,798

(22) Filed: Jan. 15, 2010

(65) Prior Publication Data
US 2010/0210034 A1 Aug. 19, 2010

Related U.S. Application Data

(60) Provisional application No. 61/145,029, filed on Jan. 15, 2009, provisional application No. 61/176,630, filed on May 8, 2009, provisional application No. 61/187,962, filed on Jun. 17, 2009.

(51) Int. Cl.
*G01N 33/574* (2006.01)
*G01N 33/53* (2006.01)
*G01N 33/567* (2006.01)
(52) U.S. Cl. ......... 435/7.23; 435/7.1; 435/7.2; 435/7.21
(58) Field of Classification Search .................. None
See application file for complete search history.

(56) References Cited

U.S. PATENT DOCUMENTS

| | | | |
|---|---|---|---|
| 4,650,750 A | 3/1987 | Giese |
| 5,340,716 A | 8/1994 | Ullman et al. |
| 5,360,819 A | 11/1994 | Giese |
| 5,480,968 A | 1/1996 | Kraus et al. |
| 5,516,636 A | 5/1996 | McCapra |
| 5,516,931 A | 5/1996 | Giese et al. |
| 5,536,834 A | 7/1996 | Singh et al. |
| 5,565,324 A | 10/1996 | Still et al. |
| 5,565,552 A | 10/1996 | Magda et al. |
| 5,602,273 A | 2/1997 | Giese et al. |
| 5,709,994 A | 1/1998 | Pease et al. |
| 5,763,602 A | 6/1998 | Li et al. |
| 6,001,673 A | 12/1999 | Marcinkiewicz |
| 6,204,007 B1 | 3/2001 | Owens et al. |
| 6,251,581 B1 | 6/2001 | Ullman et al. |
| 6,322,980 B1 | 11/2001 | Singh |
| 6,514,700 B1 | 2/2003 | Singh |
| 6,627,400 B1 | 9/2003 | Singh et al. |
| 6,630,296 B2 | 10/2003 | Xue et al. |
| 6,649,351 B2 | 11/2003 | Matray et al. |
| 6,673,550 B2 | 1/2004 | Matray et al. |
| 6,682,887 B1 | 1/2004 | Singh |
| 6,686,152 B2 | 2/2004 | Singh et al. |
| 6,770,439 B2 | 8/2004 | Singh et al. |
| 6,818,399 B2 | 11/2004 | Singh et al. |
| 6,846,645 B2 | 1/2005 | Xue et al. |
| 6,916,612 B2 | 7/2005 | Singh et al. |
| 6,949,347 B2 | 9/2005 | Singh et al. |
| 6,955,874 B2 | 10/2005 | Singh et al. |
| 7,001,725 B2 | 2/2006 | Singh et al. |
| 7,037,654 B2 | 5/2006 | Chenna et al. |
| 7,041,459 B2 | 5/2006 | Singh et al. |
| 7,045,311 B2 | 5/2006 | Ciambrone et al. |
| 7,105,308 B2 | 9/2006 | Chan-Hui et al. |
| 7,135,300 B2 | 11/2006 | Chan-Hui et al. |
| 7,160,735 B2 | 1/2007 | Dehlinger et al. |
| 7,217,531 B2 | 5/2007 | Singh et al. |
| 7,255,999 B2 | 8/2007 | Singh et al. |
| 7,279,585 B2 | 10/2007 | Singh et al. |
| 7,306,904 B2 | 12/2007 | Landegren et al. |
| 7,312,034 B2 | 12/2007 | Virgos et al. |
| 7,320,860 B2 | 1/2008 | Landegren et al. |
| 7,351,528 B2 | 4/2008 | Landegren |
| 7,358,052 B2 | 4/2008 | Singh |
| 7,402,397 B2 | 7/2008 | Chan-Hui et al. |
| 7,402,398 B2 | 7/2008 | Pidaparthi et al. |
| 7,402,399 B2 | 7/2008 | Mukherjeei et al. |
| 7,537,938 B2 | 5/2009 | Kirakossian et al. |
| 7,648,828 B2 | 1/2010 | Chan-Hui et al. |
| 7,771,929 B2 | 8/2010 | Singh et al. |
| 2002/0045738 A1 | 4/2002 | Singh et al. |
| 2002/0058263 A1 | 5/2002 | Singh et al. |

(Continued)

FOREIGN PATENT DOCUMENTS

AU 2001280222 8/2001

(Continued)

OTHER PUBLICATIONS

Amler, L. et al, "Downregulation of HER3 may predict clinical benefit in ovarian cancer from pertuzumab, a HER2 dimerization-inhibiting antibody," 2008 Molecular Markers Meeting, Amer. Soc. Clin. Onc., Abstract 25.
Antibodies: A Laboratory Manual, 1988, Harlow, E. And Lane, D. eds., Cold Spring Harbor Laboratory Press; New York.
Arkin, M. and Moasser, M., "HER-2-directed, small-molecule antagonists," 2008, Curr. Opin. Investig. Drugs, 9:1264-1276.
Atkinson, et al., "Biomarkers and surrogate endpoints: Preferred definitions and conceptual framework," 2001, Clin. Pharmacol. Ther., 69:89-95.
Bagshawe, K. et al., "A cytotoxic agent can be generated selectively at cancer sites," 1988, Br. J. Cancer, 58:700-703.
Basic Methods in Antibody Production and Characterization, 2001, Howard, C. and Bethell, D. eds, CRC Press.

(Continued)

*Primary Examiner* — Anne M. Gussow
(74) *Attorney, Agent, or Firm* — Kilpatrick Townsend & Stockton LLP

(57) ABSTRACT

The invention provides methods of measuring and/or quantifying the presence and/or amount of Her-3 and/or Her-3 in a complex in a sample. The invention also provides antibodies specific for Her-3.

51 Claims, 20 Drawing Sheets

U.S. PATENT DOCUMENTS

| | | |
|---|---|---|
| 2003/0059863 A1 | 3/2003 | Clinton |
| 2003/0092012 A1 | 5/2003 | Chenna et al. |
| 2003/0157109 A1 | 8/2003 | Corvalan et al. |
| 2003/0170734 A1 | 9/2003 | Williams et al. |
| 2003/0175747 A1 | 9/2003 | Singh |
| 2003/0203408 A1 | 10/2003 | Williams et al. |
| 2003/0207300 A1 | 11/2003 | Matray et al. |
| 2003/0235832 A1 | 12/2003 | Chenna et al. |
| 2004/0005643 A1 | 1/2004 | De Santis et al. |
| 2004/0005647 A1 | 1/2004 | Denardo et al. |
| 2004/0029139 A1 | 2/2004 | Singh |
| 2004/0052811 A1 | 3/2004 | Zielinski et al. |
| 2004/0067498 A1 | 4/2004 | Chenna et al. |
| 2004/0071696 A1 | 4/2004 | Adams et al. |
| 2004/0091850 A1 | 5/2004 | Boone et al. |
| 2004/0166529 A1 | 8/2004 | Singh et al. |
| 2004/0175765 A1 | 9/2004 | Singh et al. |
| 2004/0197815 A1 | 10/2004 | Singh et al. |
| 2004/0229293 A1 | 11/2004 | Chan-Hui et al. |
| 2004/0229294 A1 | 11/2004 | Chan-Hui et al. |
| 2004/0229299 A1 | 11/2004 | Badal et al. |
| 2004/0229380 A1 | 11/2004 | Chan-Hui et al. |
| 2004/0241686 A1 | 12/2004 | Nelson |
| 2004/0248150 A1 | 12/2004 | Singh et al. |
| 2004/0248151 A1 | 12/2004 | Bacus et al. |
| 2004/0248325 A1 | 12/2004 | Bukusoglu |
| 2004/0265858 A1 | 12/2004 | Singh et al. |
| 2005/0048553 A1 | 3/2005 | Chenna et al. |
| 2005/0130238 A1 | 6/2005 | Chan-Hui et al. |
| 2005/0130246 A1 | 6/2005 | Salimi-Moosavi et al. |
| 2005/0131006 A1 | 6/2005 | Mukherjee et al. |
| 2005/0170438 A1 | 8/2005 | Chan-Hui et al. |
| 2005/0226872 A1 | 10/2005 | Adam et al. |
| 2006/0199231 A1 | 9/2006 | Moore et al. |
| 2006/0204966 A1 | 9/2006 | Spector et al. |
| 2006/0212956 A1 | 9/2006 | Crocker et al. |
| 2006/0223107 A1 | 10/2006 | Chenna et al. |
| 2007/0037228 A1 | 2/2007 | Moecks et al. |
| 2007/0059785 A1 | 3/2007 | Bacus et al. |
| 2007/0190599 A1 | 8/2007 | Nakano et al. |
| 2007/0203408 A1 | 8/2007 | Say et al. |
| 2008/0131883 A1 | 6/2008 | Adams et al. |
| 2008/0182255 A1 | 7/2008 | Baker et al. |
| 2008/0187948 A1 | 8/2008 | Chan-Hui et al. |
| 2008/0233602 A1 | 9/2008 | Chan-Yui et al. |
| 2008/0254497 A1 | 10/2008 | Singh |
| 2008/0311674 A1 | 12/2008 | Singh et al. |
| 2009/0011432 A1 | 1/2009 | Chan-Hui et al. |
| 2009/0011440 A1 | 1/2009 | Mukherjee et al. |
| 2009/0111127 A1 | 4/2009 | Chan-Hui et al. |
| 2009/0155819 A1 | 6/2009 | Pidaparthi et al. |
| 2009/0173631 A1 | 7/2009 | Boone et al. |
| 2009/0191559 A1 | 7/2009 | Huang et al. |
| 2009/0311262 A1 | 12/2009 | Lopez et al. |
| 2010/0143927 A1 | 6/2010 | Sperinde et al. |
| 2010/0210034 A1 | 8/2010 | Bates et al. |
| 2010/0233732 A1 | 9/2010 | Bates et al. |
| 2010/0291594 A1 | 11/2010 | Chan-Hui et al. |
| 2011/0180408 A1 | 7/2011 | Badal et al. |

FOREIGN PATENT DOCUMENTS

| | | |
|---|---|---|
| CA | 2403326 | 11/2001 |
| EP | 0484027 | 5/1992 |
| EP | 1278760 | 6/2008 |
| EP | 1540347 | 9/2009 |
| ES | 2342646 | 7/2010 |
| WO | WO 93/16185 | 8/1993 |
| WO | WO 00/66607 | 11/2000 |
| WO | WO 01/83502 | 11/2001 |
| WO | WO 02/12547 | 2/2002 |
| WO | WO 02/94998 | 11/2002 |
| WO | WO 02/95356 | 11/2002 |
| WO | WO 03/006947 | 1/2003 |
| WO | WO 03/032867 | 4/2003 |
| WO | WO 03/033741 | 4/2003 |
| WO | WO 03/042398 | 5/2003 |
| WO | WO 03/042657 | 5/2003 |
| WO | WO 03/042658 | 5/2003 |
| WO | WO 03/042699 | 5/2003 |
| WO | WO 03/051669 | 6/2003 |
| WO | WO 03/076649 | 9/2003 |
| WO | WO 03/085374 | 10/2003 |
| WO | WO 2004/010842 | 2/2004 |
| WO | WO 2004/011900 | 2/2004 |
| WO | WO 2004/061131 | 7/2004 |
| WO | WO 2004/061446 | 7/2004 |
| WO | WO 2004/063700 | 7/2004 |
| WO | WO 2004/068116 | 8/2004 |
| WO | WO 2004/087887 | 10/2004 |
| WO | WO 2004/091384 | 10/2004 |
| WO | WO 2004/092353 | 10/2004 |
| WO | WO 2005/019470 | 3/2005 |
| WO | WO 2005/037071 | 4/2005 |
| WO | WO 2005/045058 | 5/2005 |
| WO | WO 2005/072507 | 8/2005 |
| WO | WO 2006/044748 | 4/2006 |
| WO | WO 2006/052788 | 5/2006 |
| WO | WO 2006/084018 | 8/2006 |
| WO | WO 2008/145338 | 12/2008 |
| WO | WO 2009/070772 | 6/2009 |
| WO | WO 2009/086197 | 7/2009 |
| WO | WO 2010/000565 | 1/2010 |
| WO | WO 2010/065568 | 6/2010 |
| WO | WO 2010/083463 | 7/2010 |
| WO | WO 2010/083470 | 7/2010 |

OTHER PUBLICATIONS

Beutner, S. et al., "Synthetic Singlet Oxygen Quenchers," 2000, In: Methods Enzymol., Packer, L. and Sies, H., eds., 319:226-241.

Bianco, R. et al., "Rational bases for the development of EGFR inhibitors for cancer treatment," 2007, Int. J. Biochem. Cell Biol., 39:1416-1431.

Bioconjugate Techniques, 1996, Hermanson, G., ed., Academic Press, New York.

Blume-Jensen, P. and Hunter, T., "Oncogenic kinase signalling," 2001, Nature, 411:355-365.

Burgess, A. et al., "An Open-and-Shut Case? Recent Insights into the Activation of EGF/ErbB Receptors," 2003, Mol. Cell, 12:541-542.

Burgess, A., "EGFR family: Structure physiology signaling and therapeutic targets,"2008, Growth Factors 26:263-274.

Cappuzzo, F. et al., "HER3 genomic gain and sensitivity to gefitinib in advanced non-small-cell lung cancer patients," 2005, Brit. J. Cancer, 93:1334-1340.

Carden, C.P. et al., "From Darkness to Light with Biomarkers in Early Clinical Trials of Cancer Drugs," 2009, Clin. Pharmacol. Ther., 85:131-133.

Carter, P. et al., "High Level *Escherichia coli* Expression and Production of a Bivalent Humanized Antibody Fragment," 1992, Bio/Technology, 10:163-167.

Carter, P. et al., "Humanization of an anti-p185$^{HER2}$ antibody for human cancer therapy," 1992, Proc. Natl. Acad. Sci. USA, 89:4285-4289.

Carter, P. and Senter, P., "Antibody-Drug Conjugates for Cancer Therapy," 2008, Cancer J., 14:154-169.

Chothia, C. And Lesk, A., "Canonical Structures for the Hypervariable Regions of Immunoglobulins," 1987, J. Mol. Biol., 196:901-917.

de Alava, E. et al., "Neuregulin Expression Modulates Clinical Response to Trastuzumab in Patients With Metastatic Breast Cancer," 2007, J. Clin. Oncol., 25:2656-2663.

Dhani, N.and Siu, L., "Clinical trials and biomarker development with molecularly targeted agents and radiotherapy," 2008, Cancer Metastasis Rev., 27:339-349.

Di Mascio, P. et al., "Singlet molecular oxygen production in the reaction of peroxynitrite with hydrogen peroxide," 1994, FEBS Lett., 355:287-289.

Engvall, E., "Enzyme-Linked Immunosorbent Assay, ELISA," 1977, Chap. 30, In: Biomedical Applications of Immobilized Enzymes and Proteins, Chang, T., ed., Plenum Press, NY, 2:87-96.

Frank, R. and Hargreaves, R., "Clinical Biomarkers in Drug Discovery and Development," 2003, Nature Reviews Drug Discovery, 2:566-580.

Fuchs, I. et al., "Epidermal Growth Factor Receptor Changes During Breast Cancer Metastasis," 2006, Anticancer Res., 26:4397-4402.
George, S. et al., "G-Protein-Coupled Receptor Oligomerization and its Potential for Drug Discovery," 2002, Nature Reviews Drug Discovery, 1:808-820.
Giese, R., "Electrophoric release tags: ultrasensitive molecular labels providing multiplicity," 1983, Trends in Anal. Chem., 2:166-168.
Goding, J.W., "Antibody Production by Hybridomas," 1980, J. Immunol. Methods, 39:285-308.
Graham, F. et al., "Characteristics of a Human Cell Line Transformed by DNA from Human Adenovirus Type 5," 1977, J. Gen. Virol., 36:59-74.
Harris, J. and Chess, R., "Effect of Pegylation on Pharmaceuticals," 2003, Nat. Rev. Drug Discov.; 2:214-221.
Herbst, R. and Shin, D., "Monoclonal Antibodies to Target Epidermal Growth Factor Receptor-Positive Tumors. A New Paradigm for Cancer Therapy," 2002, Cancer, 94:1593-1611.
Jones, P. et al., "Replacing the complementarity-determining regions in a human antibody with those from a mouse," 1986, Nature, 321:522-525.
Kanofsky, J., "Singlet Oxygen Production by Lactoperoxidase: Evidence from 1270 nm Chemiluminescence," 1983, J. Biol. Chem., 258:5991-5993.
Köhler, G. and Milstein, C., "Continuous cultures of fused cells secreting antibody of predefined specificity," 1975, Nature, 256:495-497.
Kraus, M. et al., "Isolation and characterization of *ERBB3*, a third member of the *ERBB*/epidermal growth factor receptor family: Evidence for overexpression in a subset of human mammary tumors," 1989, Proc. Natl. Acad. Sci. USA, 86:9193-9197.
Kreitman, R., "Immunotoxins for Targeted Cancer Therapy," 2006, AAPS J., 18:E532-E551.
Lee, J. et al., "Biomarker Assay Translation from Discovery to Clinical Studies in Cancer Drug Development : Quantification of Emerging Protein Biomarkers," 2007, In: Advances in Cancer Research, Woude, G. et al., eds., 96:269-298.
Lee-Hoeflich, S. et al., "A Central Role for HER3 in *HER2*-Amplified Breast Cancer: Implications for Targeted Therapy," 2008, Cancer Res., 68:5878-5887.
Lizardi, P. et al., "Mutation detection and single-molecule counting using isothermal rolling-circle amplification," 1998, Nat. Genet., 19:225-232.
Ludwig, J. and Weinstein, J., "Biomarkers in Cancer Staging, Prognosis and Treatment Selection," 2005, Nature Reviews Cancer, 5:845-856.
Ma, C. and Bose, R., "Current and Future Roles of Lapatinib in HERs-Positive Breast Cancer," 2008, E-Updates in HER1 and HER2 Targeting in Breast Cancer, vol. 2.
Makhija, S. et al., "HER pathway gene expression analysis in a phase II study of pertuzumab + gemcitabine vs. gemcitabine + placebo in patients with platinum-resistant epithelial ovarian cancer," 2008, J. Clin. Oncol., 26:Supp. Pt 1, Abstract 5552.
Manual of Histologic Staining Methods of the Armed Forces Institute of Pathology, 1960, Third Edition, Luna, L., ed., McGraw-Hill Book Company, New York.
Martin, J. and Burch, P., "Production of Oxygen Radicals by Photosensitization," 1990, In: Methods Enzymol., Packer, L. and Glazer, A., eds., 186:635-645.
McCormick, F., "Signalling networks that cause cancer," 1999, Trends in Cell Biology, 9:M53-M56.
Mellado, M. et al., "Chemokine Signaling and Functional Responses: The Role of Receptor Dimerization and TK Pathway Activation," 2001, Annu. Rev. Immunol., 19:397-421.
Menendez, J. and Lupu, R., "Transphosphorylation of kinase-dead HER3 and breast cancer progression: a new standpoint or an old concept revisited?," 2007, Breast Cancer Research, 9:111 (5 pp.).
Mignot, G. et al., "Prospects for exosomes in immunotherapy of cancer," 2006, J. Cell. Mol. Med., 10:376-388.
Monoclonal Antibodies. Hybridomas: A New Dimension in Biological Analyses, 1980, Kennet, R. et al., eds., Plenum Press, NY.
Mosesson, Y. and Yarden, Y., "Oncogenic growth factor receptors: implications for signal transduction therapy," 2004, Semin. Cancer. Biol., 14:262-270.

Normanno, N. et al., "Epidermal growth factor receptor (EGFR) signaling in cancer," 2006, Gene, 366:2-16.
Ono, M. and Kuwano, M., "Molecular Mechanisms of Epidermal Growth Factor Receptor (EGFR) Activation and Response to Gefitinib and Other EGFR-Targeting Drugs," 2006, Clin. Cancer Res., 12:7242-7251.
Osipo, C. et al., "Role for HER2/neu and HER3 in fulvestrant-resistant breast cancer," 2007, Int. J. Oncol., 30:509-520.
Pearse, A.G.E., Histochemistry: Theoretical and Applied, vol. 1, Preparative and Optical Technology, 4th Ed., 1980, Churchill Livingstone, Edinburgh.
Petricoin, E. et al., "Clinical Proteomics: Translating Benchside Promise into Bedside Reality," 2002, Nature Review Drug Discovery, 1:683-695.
Pierlot, C. et al., "Naphthalene Endoperoxides as Generators of Singlet Oxygen in Biological Media," 2000, In: Methods Enzymol., Packer, L. and Sies, H., eds., 319:3-20.
Plowman, G. et al., "Molecular cloning and expression of an additional epdermal growth factor receptor-related gene," 1990, Proc. Natl. Acad. Sci. USA, 87:4905-4909.
Plückthun, A., "Mono- and Bivalent Antibody Fragments Produced in *Escherichia coli*: Engineering, Folding and Antigen Binding," 1992, Immunological Rev., 130:151-188.
Presta, L. et al., "Humanization of an Antibody Directed Against IgE," 1993, J. Immunol., 151:2623-2632.
Protective Groups in Organic Synthesis, 1991, 2nd Edition, Greene, T. and Wuts, P., eds., John Wiley & Sons, New York.
Radiommunoassay and Saturation Analysis, 1974, Sönksen, P.H., ed., Brit. Med. Bull. 30:1-103.
Riechmann, L. et al., "Reshaping human antibodies for therapy," 1988, Nature, 332:323-327.
Schlessinger, J., "Cell Signaling by Receptor Tyrosine Kinases," 2000, Cell, 103:211-225.
Semba, K. et al., "A v-*erbB*-related protooncogene, c-*erbB*-2, is distinct from the c-*erbB-1*/epidermal growth factor-receptor gene and is amplified in a human salivary gland adenocarcinoma," 1985, Proc. Natl. Acad. Sci. USA, 82:6497-6501.
Senter, P. et al., "Anti-tumor effects of antibody—alkaline phosphatase conjugates in combination with etoposide phosphate," 1988, Proc. Natl. Acad. Sci. USA, 85:4842-4846.
Sergina, N. et al., "Escape from HER-family tyrosine kinase inhibitor therapy by the kinase-inactive HER3," 2007, Nature, 445:437-441.
Sidransky, D., "Emerging Molecular Markers of Cancer," 2002, Nature Reviews Cancer, 2:210-219.
Sithanandam, G. and Anderson, L., "The ERBB3 receptor in cancer and cancer gene therapy," 2008, Cancer Gene Ther., 15:413-448.
Stern, D., "ERBB3/HER3 and ERBB2/HER2 Duet in Mammary Development and Breast Cancer," 2008, J. Mammary Gland Biol. Neoplasia, 13:215-223.
Strong, L. et al., "Antibody-targeted Photolysis: Photophysical, Biochemical, and Pharmacokinetic Properties of Antibacterial Conjugates," 1994, Ann. New York Acad. Sci., 745:297-320.
Taylor, D. and Black, P., "Inhibition of Macrophage Ia Antigen Expression by Shed Plasma Membrane Vesicles From Metastatic Murine Melanoma Lines," 1985, J. Natl. Cancer Inst., 74:859-867.
The Armed Forces Institute of Pathology Advanced Laboratory Methods in Histology and Pathology, Armed Forces Institute of Pathology, American Registry of Pathology, 1994, Mikel, U., ed., Washington, DC.
The Immunoassay Handbook, 1994, Wild, D. ed., Stockton Press, New York.
Theory and Practice of Histological Techniques, 1997, Bancroft, J. and Stevens, A., eds., Churchill Livingston, New York.
Therasse, P. et al., "New Guidelines to Evaluate the Response to Treatment in Solid Tumors," 2000, J. Natl. Cancer Institute, 92:205-216.
Tovey, S. et al., "Low expression of HER2 protein in breast cancer is biologically significant," 2006, J. Pathol., 210:358-362.
Ullman, E. et al., "Luminescent oxygen channeling immunoassay : Measurement of particle binding kinetics by chemiluminescence," 1994, Proc. Natl. Acad. Sci. USA, 91:5426-5430.
Verhoeyen, M. et al., "Reshaping Human Antibodies: Grafting an Antilysozyme Activity," 1988, Science, 239:1534-1536.

Voller, A. et al., "Enzyme immunoassays with special reference to ELISA techniques," 1978, J. Clin. Pathol., 31:507-520.

Xu, F. et al., "The Outcome of Heregulin-induced Activation of Ovarian Cancer Cells Depends on the Relative Levels of HER-2 and HER-3 Expression," 1999, Clin. Cancer Res., 5:3653-3660.

Yamamoto, T. et al., "Similarity of protein encoded by the human c-erb-B-2 gene to epidermal growth factor receptor," 1986, Nature, 319:230-234.

Yarden, Y. and Sliwkowski, M., "Untangling the ErbB Signalling Network," 2001, Nature Reviews Molecular Cell Biology, 2:127-137.

Yarden, Y., "The EGFR family and its ligands in human cancer: signalling mechanisms and therapeutic opportunities," 2001, Eur. J. Cancer, 37:S3-S8.

Yarmush, M. et al., "Antibody Targeted Photolysis," 1993, Crit. Rev. Therapeutic Drug Carrier Syst., 10:197-252.

Zhang, X. et al., "Synthesis of Releasable Electrophore Tags for Applications in Mass Spectrometry," 2002, Bioconjugate Chem., 13:1002-1012.

Zola, H., 1987, Monoclonal Antibodies: A Manual of Techniques, CRC Press, FL.

International Search Report mailed Jun. 2, 2010 corresponding to Application No. PCT/US10/21281.

Written Opinion of the International Searching Authority mailed Jun. 2, 2010 corresponding to Application No. PCT/US10/21281.

International Preliminary Report on Patentability mailed Jul. 28, 2011 for corresponding International Application No. PCT/US2010/021281.

Patent Cooperation Treaty, International Search Report and Written Opinion, International Application No. PCT/US10/21272, mailed Mar. 1, 2010.

Patent Cooperation Treaty, International Preliminary Report on Patentability, International Application No. PCT/US10/21272, mailed Dec. 2, 2011.

Patent Cooperation Treaty, International Search Report and Written Opinion, International Application No. PCT/US09/66295, mailed May 25, 2010.

Patent Cooperation Treaty, International Search Report and Written Opinion, International Application No. PCT/US08/87828, mailed Mar. 17, 2009.

Huang, W. et al., "Comparison of Central HER-2 Tests With Quantitative HER-2 Expression and HER-2 Homodimer Measurements Using A Novel Proximity Based Assay," Abstract 40, American College of Pathologist Annual Meeting, Sep. 25-28, 2008. Available on the Internet: <URL:http://www.hermarkassay.com/publications.aspx>.

Saez, R. et al., "p95HER-2 Predicts Worse Outcome in Patients With HER-2-Positive Breast Cancer," Clin. Cancer Res., 2006, 12(2):424-431.

Xia, W. et al., "Truncated ErbB2 Receptor ($p95^{ErbB2}$) Is Regulated by Heregulin Through Heterodimer Formation With ErbB3 Yet Remains Sensitive to the Dual EGFR/ErbB2 Kinase Inhibitor GW572016," Oncogene, 2004, 23(3):646-653.

Bates, M.P., et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," J. of Clinical Oncology, 2007 (Jun. 20, 2007 Supplement), 25:18S (Abstract).

Dua, R., et al., "Profiling HER-Family Receptor Dimerization in HER2 Overexpressing Cells that Coexpress Mutated EGFR Receptors," Breast Cancer Research and Treatment, Dec. 13, 2007, 106(1):S203 (Abstract).

Dua, R., et al., "Profiling HER-Family Receptor Dimerization in HER2 Overexpressing Cells that Coexpress Mutated EGFR Receptors," 30th Annual San Antonio Breast Cancer Symposium, Dec. 13-16, 2007; San Antonio, TX, USA (Poster).

Dua, R., et al., "Patterns of HER-Family Receptor Dimerization Intrastuzumab Susceptible and Trastuzumab Resistant Cell Lines," J. of Clinical Oncology, Jun. 20, 2007, 25:18S (Abstract).

Dua, R., et al., "Patterns of HER-Family Receptor Dimerization Intrastuzumab Susceptible and Trastuzumab Resistant Cell Lines," American Society of Clinical Oncology (ASCO) Conference 2007, Jun. 1-5, Chicago, IL, USA (Poster).

Eli, L., et al., "Development of Novel Proximity-Based Immunoassays for the Detection of HER Heterodimerization in Breast Cancer Cell Line Lysates and Formalin-Fixed, Paraffin-Embedded Tissue," Breast Cancer Research and Treatment, Dec. 13, 2007, 106(1):S87-S88 (Abstract).

Eli, L., et al., "Development of Novel Proximity-Based Immunoassays for the Detection of HER Heterodimerization in Breast Cancer Cell Line Lysates and Formalin-Fixed, Paraffin-Embedded Tissue," 30th Annual San Antonio Breast Cancer Symposium, Dec. 13-16, 2007; San Antonio, TX, USA (Poster).

Huang, W., et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," Breast Cancer Research and Treatment, Dec. 13, 2007, 106(1):586 (Abstract).

Huang, W., et al., "Quantitative Measurements of HER2 Expression and HER2: HER2 Dimerization Identify Subgroups of HER2 Positive Metastatic Breast Cancer Patients with Different Probabilities of Response to Trastuzumab Treatment," 30th Annual San Antonio Breast Cancer Symposium, Dec. 13-16, 2007; San Antonio, TX, USA (Poster).

Toi, M., et al., "Differential Survival Following Trastuzumab Treatment Based on Quantitative HER2 Expression and HER2 Dimerization in a Clinic-Based Cohort of Patients With Metastatic Breast Cancer," J. of Clinical Oncology, 2007 (Jun. 20, 2007 Supplement), 25:18S (Abstract).

Wallweber, J., et al., "Increased Detection of Breast Cancer Markers Human Epidermal Growth Factor Receptor Dimer and Downstream Signaling Proteins Utilizing the VeraTag Technology with Dextran Modified Antibodies," Breast Cancer Research and Treatment, Dec. 13, 2007, 106(1):5207 (Abstract).

Wallweber, J., et al., "Increased Detection of Breast Cancer Markers Human Epidermal Growth Factor Receptor Dimer and Downstream Signaling Proteins Utilizing the VeraTag Technology with Dextran Modified Antibodies," 30th Annual San Antonio Breast Cancer Symposium, Dec. 13-16, 2007; San Antonio, TX, USA (Poster).

Winslow, J., et al., "Characterization of a Novel Proximity Immunoassay for the Quantitative Determination of HER2 Protein Expression and HER2 Homodimerization in Famalin-Fixed, Paraffin-Embedded Breast Cancer Tissue," Breast Cancer Research and Treatment, Dec. 13, 2007, 106(1):588 (Abstract).

Winslow, J., et al., "Characterization of a Novel Proximity Immunoassay for the Quantitative Determination of HER2 Protein Expression and HER2 Homodimerization in Famalin-Fixed, Paraffin-Embedded Breast Cancer Tissue," 30th Annual San Antonio Breast Cancer Symposium, Dec. 13-16, 2007; San Antonio, TX, USA (Poster).

Mukherjee, A. et al., "Correlation of ErbB activation status and clinical response in Herceptin treated breast cancer patients," Proc. Amer. Canc. Res., Apr. 16-20, 2005, 46: 3688 (Abstract).

Mukherjee, A. et al., "Correlation of ErbB activation status and clinical response in Herceptin treated breast cancer patients," 96th Annual Meeting of the American Association for Cancer Research, Apr. 16-20, 2005, Anaheim/Orange County, CA, USA (Poster).

Wolff, A.C., et al., "American Society of Clinical Oncology/College of American Pathologists Guideline Recommendations for Human Epidermal Growth Factor Receptor 2 Testing in Breast Cancer," J. of Clinical Oncology, Jan. 1, 2007, 25(1): 118-145 (published online Dec. 11, 2006).

Anido, J., et al., "Biosynthesis of tumorigenic HER2 C-terminal Fragments by Alternative Initiation of Translation," EMBO J., 2006, 25:3234-3244.

Conover, W. J., Practical Nonparametric Statistics, 3rd Ed, 1999., John Wiley and Sons Inc.

Gee, J. and Knowlden J., "ADAM Metalloproteases and EGFR Signalling," Breast Cancer Res., 2003, 5:223-224.

Goldenberg, M., "Trastuzumab, A Recombinant DNA-Derived Humanized Monoclonal Antibody, A Novel Agent for the Treatment of Metastatic Breast Cancer," Clin. Ther., 1999, 21(2):309-318.

Kearney, J.F. et al., "A New Mouse Myeloma Cell Line That Has Lost Immunoglobin Expression But Permits the Construction of Antibody-Secreting Hybrid Cell Lines," J. Immunology, 1979, 123:1548-1550.

Liu, P. et al., "Identification of ADAM10 As A Major Source of HER2 Ectodomain Sheddase Activity in HER2 Overexpressing Breast Cancer Cells," Cancer Biol. Therapy, 2006, 6:657-664.

Pendersen, K. et al., A Naturally Occurring HER2 Carboxy-Terminal Fragment Promotes Mammary Tumor Growth and Metastasis, Mol. Cell Biol., 2009, 29:331-31.

Molina, M. et al., "$NH_2$-terminal Truncated HER-2 Protein But Not Full-Length Receptor Is Associated With Nodal Metastasis in Human Breast Cancer," Clin. Can. Res., 2002, 8:347-353.

Romond, E., "Trastuzumab Plus Adjuvant Chemotherapy For Operable HER2-Positive Breast Cancer," N. Engl. J. Med., 2005, 353(16):1673-1684.

Sahin, U. et al., "Distinct Roles for ADAM10 and ADAM17 in Ectodomain Shedding of Six EGFR Ligands," J. Cell Biol., 2004, 164(5):769-779.

Shak, S., "Overview of the Trastuzumab (Herceptin) Anti-HER2 Monoclonal Antibody Clinical Program in HER2-Overexpressing Metastatic Breast Cancer," Semin Oncol., 1999, 26(4):71-77.

Sims, M. et al., A Humanized CD18 Antibody Can Block Function without Cell Destruction, J. Immunol., 1993, 151:2296-2308.

Spector, N. et al., "Small Molecule HER-2 Tyrosine Kinase Inhibitors," Breast Cancer Res., 2007, 9:205-212.

Yuan, C. et al., Purification of HER-2 Extracellular Domain and Identification of Its Cleavage Site, Pro. Expr & Purifi, 2003, 29:217-222.

Zabrecky, J. et al., "The Extracellular Domain of p185/neu Is Released From the Surface of Human Breast Carcinoma Cells, SK-BR-3," J. Biol. Chem., 1991, 266(3):1716-1720.

Biernat, W. et al., "Quantitative HER2 levels and steroid receptor expression in primary breast cancers and in matched brain metastases," 2012 J. Clin. Oncol. 30 (Jun. 20 Suppl.): Abstract 603.

Biernat, W. et al., "Quantitative HER2 levels and steroid receptor expression in primary breast cancers and in matched brain metastases," American Society of Clinical Oncology (ASCO) Annual Meeting, May 31-Jun. 4, 2012; Chicago, IL (Poster 603).

Huang, W. et al., "Quantitative HER2 measurement and PI3K mutation profile in matched primary and metastatic breast cancer tissues," 2012 J. Clin. Oncol. 30 (Jun. 20 Suppl.): Abstract 614.

Huang, W. et al., "Quantitative HER2 measurement and PI3K mutation profile in matched primary and metastatic breast cancer tissues," American Society of Clinical Oncology (ASCO) Annual Meeting, May 31-Jun. 4, 2012, Chicago, IL (Poster 614).

Sperinde, J. et al., "A comparative study of p95-HER2 carboxy terminal fragment (CTF) detected by immunohistochemistry and VeraTag immunoassays in human breast tumors," In: Proc. Am. Assoc. Cancer Res., Mar. 31-Apr. 4, 2012, Chicago, IL. Philadelphia (PA): AACR; Cancer Res. 2012, 72(8 Suppl): Abstract 687.

Sperinde, J. et al., "A comparative study of p95-HER2 carboxy terminal fragment (CTF) detected by immunohistochemistry and VeraTag immunoassays in human breast tumors," American Association for Cancer Research (AACR) Annual Meeting, Mar. 31-Apr. 4, 2012, Chicago, IL (Poster 687).

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," 2012 J. Clin. Oncol. 30 (Jun. 20 Suppl.): Abstract 608.

Villasboas, J.C. et al., "Correlation of quantitative p95HER2, HER3, and HER2 protein expression with pathologic complete response (pCR) in HER2-positive breast cancer patients treated with neoadjuvant (NEO) trastuzumab containing therapy," American Society of Clinical Oncology (ASCO) Annual Meeting, May 31-Jun. 4, 2012, Chicago, IL (Poster 608).

Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," 2011 J. Clin. Oncol. 29(15)(May 20 Suppl.): Abstract 586.

Biernat, W. et al., "Quantitative measurements of p95HER2 (p95) and total HER2 (H2T) protein expression in patients with trastuzumab-treated, metastatic breast cancer (MBC): Independent confirmation of clinical cutoffs," American Society of Clinical Oncology (ASCO) Annual Meeting, Jun. 3-7, 2011, Chicago, IL (Poster 586).

Cook, J.W. et al., "Mutations in the catalytic domain of PI3 kinase and correlation with clinical outcome in trastuzumab-treated metastatic breast cancer (MBC)," 2011 J. Clin. Oncol. 29(15)(May 20 Suppl.): Abstract 582.

Cook, J.W. et al., "Mutations in the catalytic domain of PI3 kinase and correlation with clinical outcome in trastuzumab-treated metastatic breast cancer (MBC)," American Society of Clinical Oncology (ASCO) Annual Meeting, Jun. 3-7, 2011, Chicago, IL (Poster 582).

Duchnowska, R. et al., "Correlation between Quantitative HER2 Protein Expression and Risk of Brain Metastases in HER2-Positive Advanced Breast Cancer Patients Receiving Trastuzumab-Containing Therapy," Cancer Research, Dec. 15, 2011, 71(24 Suppl. 3):291s (Abstract P2-12-05).

Duchnowska, R. et al., "Correlation between Quantitative HER2 Protein Expression and Risk of Brain Metastases in HER2-Positive Advanced Breast Cancer Patients Receiving Trastuzumab-Containing Therapy," Annual San Antonio Breast Cancer Symposium, Dec. 6-10, 2011, San Antonio, TX, USA (Poster P2-12-05).

Huang, W. et al., "Comparison of four HER2 testing methods in detection of HER2-positive breast cancer: results in the FinHer study cohort," Cancer Research, Dec. 15, 2011, 71(24)(Suppl. 3):187s-188s (Abstract P1-07-01).

Huang, W. et al., "Comparison of four HER2 testing methods in detection of HER2-positive breast cancer: results in the FinHer study cohort," Annual San Antonio Breast Cancer Symposium, Dec. 6-10, 2011, San Antonio, TX, USA (Poster P1-07-01).

Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Cancer Research, Dec. 15, 2011, 71(24)(Suppl. 3):192s-193s (Abstract P1-07-12).

Huang, W. et al., "Assessment of real-world HER2 status by immunohistochemistry (IHC) and fluorescence in situ hybridization (FISH) in breast cancers: Comparison with HERMark®, a validated quantitative measure of HER2 protein expression," Annual San Antonio Breast Cancer Symposium, Dec. 6-10, 2011, San Antonio, TX, USA (Poster P1-07-12).

Shi, Y. et al., "Quantitative measurement of HER3-PI3K complex and total p85α subunit in formalin-fixed, paraffin-embedded (FFPE) tissues using VeraTag™ immunoassays," American Association for Cancer Research Special Conference: Targeting PI3K/mTOR Signaling in Cancer, Feb. 24-27, 2011, San Francisco, CA: Poster.

Wallweber, J. et al., "Subclassification of squamous cell carcinomas of the head and neck based on HER/ErbB and c-MET receptor protein expression and activation profiles," In: Proc. Am. Assoc. Cancer Res. AACR, Apr. 2-6, 2011, Orlando, FL: Abstract LB-323.

Wallweber, J. et al., "Subclassification of squamous cell carcinomas of the head and neck based on HER/ErbB and c-MET receptor protein expression and activation profiles," American Association for Cancer Research (AACR) Annual Meeting, Apr. 2-6, 2011, Orlando, FL (Poster LB-323).

Duchnowska, R. et al., "Correlation between quantitative HER2 Protein level and the risk of brain metastases (BM) in patients (ots) with metastatic breast cancer (MBC) treated with trastuzumab-containing therapy," 2010 J. Clin. Oncol. 28(15s) (Jun. 20 Suppl.): Abstract 1030.

Duchnowska, R. et al., "Correlation between quantitative HER2 Protein level and the risk of brain metastases (BM) in patients (ots) with metastatic breast cancer (MBC) treated with trastuzumab-containing therapy," American Society of Clinical Oncology (ASCO) Annual Meeting, Jun. 4-8, 2010, Chicago, IL (Poster 1030).

Wallweber, J., "Quantitative assessment of HER/erbB receptor protein expression and activation status in FFPE tumor samples identifies an activated HER1 signature in squamous cell carcinomas of the head and neck," In: Proc. Am. Assoc. Cancer Res. AACR, Apr. 17-21, 2010, Washington, D.C.: Abstract LB-66.

Wallweber, J., "Quantitative assessment of HER/erbB receptor protein expression and activation status in FFPE tumor samples identifies an activated HER1 signature in squamous cell carcinomas of the head and neck," American Association for Cancer Research (AACR) Annual Meeting, Apr. 17-21, 2010, Washington, D.C. (Poster LB-66).

Bates, M. et al., "Relationship between Quantitative HER2 Protein Expression and Clinical Outcomes in ER-Positive and ER-Negative Sub-Groups of Patients with Trastuzumab," Dec. 15, 2009, Cancer Research 69(24)(Suppl. 1): Abstract 5136.

Bates, M. et al., "Relationship between Quantitative HER2 Protein Expression and Clinical Outcomes in ER-Positive and ER-Negative Sub-Groups of Patients with Trastuzumab," $32^{nd}$ Annual San Antonio Breast Cancer Symposium, Dec. 9-13, 2009, San Antonio, TX, USA (Poster 5136).

Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," In: Proc. Am. Assoc. Cancer Res. AACR, Apr. 18-22, 2009, Denver, CO: Abstract 5247.

Eli, L. et al., "Quantitative measurements of phosphorylated HER1, HER2, and HER1-HER2 heterodimers in formalin-fixed, paraffin-embedded (FFPE) breast and head/neck tumors using proximity-based immunoassays," American Association of Cancer Research (AACR) Annual Meeting, Apr. 18-22, 2009, Denver, CO (Poster 5247).

Joensuu, H. et al. "Breast cancer patients with very high tumor HER2 expression levels might not benefit from treatment with trastuzumab plus chemotherapy: A retrospective exploratory analysis of the FinHer trial," Dec. 15, 2009, Cancer Research 69(24)(Suppl. 1): Abstract 5083.

Joensuu, H. et al. "Breast cancer patients with very high tumor HER2 expression levels might not benefit from treatment with trastuzumab plus chemotherapy: A retrospective exploratory analysis of the FinHer trial," $32^{nd}$ Annual San Antonio Breast Cancer Symposium, Dec. 10-13, 2009, San Antonio, TX, USA.

Williams, S. et al., "Profiling PI3K-Akt pathway activation in formalin fixed, paraffin-embedded cell line models and breast and ovarian tumors using a novel proximity assay," In: Proc. Am. Assoc. Cancer Res. AACR, Apr. 18-22, 2009, Denver, CO: Abstract 5251.

Williams, S. et al., "Profiling PI3K-Akt pathway activation in formalin fixed, paraffin-embedded cell line models and breast and ovarian tumors using a novel proximity assay," American Association of Cancer Research (AACR) Annual Meeting, Apr. 18-22, 2009, Denver, CO (Poster 5251).

Lipton, A. et al., "Multiple Subtypes of HER-2/Neu-Positive Metastatic Breast Cancer," Cancer Research, Dec. 15, 2009, 69(24 Suppl. 1): Abstract 2030.

Lipton, A. et al., "Multiple Subtypes of HER-2/Neu-Positive Metastatic Breast Cancer," $32^{nd}$ Annual San Antonio Breast Cancer Symposium, Dec. 9-13, 2009, San Antonio, TX, USA (Poster 2030).

Shi, Y. et al., "Quantitative, sensitive, and reproducible measurement of epidermal growth factor receptor/HER1 homodimerization and total expression in formalin-fixed, paraffin-embedded tumors using a novel proximity-based assay," In: Proc. Am. Assoc. Cancer Res. Aacr, Apr. 18-22, 2009, Denver, CO: Abstract 5244.

Shi, Y. et al., "Quantitative, sensitive, and reproducible measurement of epidermal growth factor receptor/HER1 homodimerization and total expression in formalin-fixed, paraffin-embedded tumors using a novel proximity-based assay," American Association of Cancer Research (AACR) Annual Meeting, Apr. 18-22, 2009 Denver, CO (Poster 5244).

Leitzel, A. et al., "Discordant HER2 Total and HER2 Homodimer Levels by HERmark Analysis in Matched Primary and Metastatic Breast Cancer FFPE Specimens," Cancer Research, Dec. 15, 2009, 69(24 Suppl. 1): Abstract 2131.

Leitzel, A. et al., "Discordant HER2 Total and HER2 Homodimer Levels by HERmark Analysis in Matched Primary and Metastatic Breast Cancer FFPE Specimens," $32^{nd}$ Annual San Antonio Breast Cancer Symposium, Dec. 9-13, 2009, San Antonio, TX, USA (Poster 2132).

Badal, M.Y. et al., "Measurement of the HER3-PI3K complex as a marker of PI3K-Akt pathway activation in formalin fixed, paraffin-embedded cell line models and breast and ovarian tumors using a novel proximity assay," American Association for Cancer Research (AACR) Special Conference on Targeting the PI3K-Kinase Pathway in Cancer, Nov. 11-14, 2008, Cambridge, MA, USA (Poster).

Bates, M., et al., "Quantitative HER2 homodimer levels correlate with time to first recurrence in HER2-positive breast cancer patients who did not receive trastuzumab in the adjuvant setting," Cancer Res. Jan. 15, 2009, 69(2 Suppl. 1): Abstract 1074.

Bates, M. et al., "Quantitative HER2 homodimer levels correlate with time to first recurrence in HER2-positive breast cancer patients who did not receive trastuzumab in the adjuvant setting," $31^{st}$ Annual San Antonio Breast Cancer Symposium, Dec. 10-14, 2008, San Antonio, TX, USA (Poster 1074).

Eli, L. et al., "Development of novel-proximity-based immunoassays for activated HER1, HER2, HER1-HER2 heterodimers in formalin-fixed, paraffin-embedded (FFPE) cells," 2008 Eur. J. Cancer 6(Oct. 12):30 (Abstract 88).

Eli, L. et al., "Development of novel-proximity-based immunoassays for activated HER1, HER2, HER1-HER2 heterodimers in formalin-fixed, paraffin-embedded (FFPE) cells," International Conference on Molecular Targets and Cancer Therapeutics, AACR-NCI-EORTC, Oct. 21-24, 2008, Geneva, Switzerland (Poster 88).

Huang, W. et al., "Comparison of Central HER-2 Tests With Quantitative HER-2 Expression and HER-2 Homodimer Measurements Using A Novel Proximity Based Assay," 2008 Arch. Pathol. Lab. Med. 132 (Sep.):1476 (CAP Abstract 40).

Huang, W. et al., "Comparison of Central HER-2 Tests With Quantitative HER-2 Expression and HER-2 Homodimer Measurements Using A Novel Proximity Based Assay," American College of Pathologist (CAP) Annual Meeting, Sep. 25-28, 2008 (Poster 40).

Joensuu, H. et al., "Quantitative measurement of HER2 expression and HER2 homodimer using a novel proximity based assay: comparison with HER2 status by immunohistochemistry and chromogenic in situ hybridization in the FinHer study," Cancer Research, Jan. 15, 2009, 69(2 Suppl. 1): Abstract 2071.

Joensuu, H. et al., "Quantitative measurement of HER2 expression and HER2 homodimer using a novel proximity based assay: comparison with HER2 status by immunohistochemistry and chromogenic in situ hybridization in the FinHer study," $3^{st}$ Annual San Antonio Breast Cancer Symposium, Dec. 10-14, 2008, San Antonio, TX, USA (Poster 2071).

Lipton, A. et al., "HER2 protein expression predicts response to trastuzumab in FISH-positive patients," Cancer Research, Jan. 15, 2009, 69(2 Suppl. 1): Abstract 32.

Lipton, A. et al., "HER2 protein expression predicts response to trastuzumab in FISH-positive patients," $31^{st}$ Annual San Antonio Breast Cancer Symposium, Dec. 10-14, 2008, San Antonio, TX, USA (Poster 32).

Leitzel K., et al., "Use of total HER2 and HER2 homodimer levels to predict response to trastuzumab," J. Clin. Oncol. 2008 (May 20 Suppl.): Abstract 1002.

Leitzel, K. et al., "Total HER2 and HER2 homodimer levels predict response to trastuzumab," American Society of Clinical Oncology (ASCO) Annual Meeting, May 30-Jun. 3, 2008, Chicago, IL (Oral Presentation 1002).

Mukherjee, A. et al., "Proximity-based assays for the detection of activated HER3, HER2/3 heterodimers and HER3/PI3K complexes in FFPE cell line controls and tumors," Cancer Research, Jan. 15, 2009, 69(2 Suppl. 1): Abstract 4040.

Mukherjee, A. et al., "Proximity-based assays for the detection of activated HER3, HER2/3 heterodimers and HER3/PI3K complexes in FFPE cell line controls and tumors," $31^{st}$ Annual San Antonio Breast Cancer Symposium, Dec. 10-14, 2008, San Antonio, TX, USA (Poster 4040).

Shi, Y. et al., "Development of highly quantitative, sensitive, and reproducible assays for the detection of EGFR/HER1 and ErbB3/HER3 in in formalin-fixed, paraffin-embedded cells," 2008 Eur. J. Cancer 6(Oct. 12):34-35 (Abstract 103).

Shi, Y. et al., "Development of highly quantitative, sensitive, and reproducible assays for the detection of EGFR/HER1 and ErbB3/HER3 in in formalin-fixed, paraffin-embedded cells," International Conference on Molecular Targets and Cancer Therapeutics, AACR-NCI-EORTC, Oct. 21-24, 2008, Geneva, Switzerland, Poster 103.

Bates, M. et al., "HER2 Expression and HER2:HER2 Dimerization Identifies Subpopulations of Metastatic Breast Cancer Patients With Different Probabilities of Long-Term Survival Following Trastuzumab Treatment and With Different Requirements for Concomitant Chemotherapy," American Society of Clinical Oncology (ASCO) Annual Meeting, Jun. 2-5, 2007, Chicago, IL (Poster 10557).

Toi, M. et al., "Differential Survival following Trastuzumab Treatment based on Quantitative HER2 Expression and HER2:HER2 Dimerization in a Clinic-Based Cohort of Patients with Metastatic Breast Cancer," American Society of Clinical Oncology (ASCO) Annual Meeting, Jun. 2-5, 2007, Chicago, IL (Poster 1025).

Hameed, M.R. et al., "The ERB family receptor dimerization in glioblastoma—An eTag assay analysis of 23 cases," 2006 J. Clin. Oncol. 24(18S) (Jun. 20 Suppl.): Abstract 1582.

Hameed, M.R. et al., "The ERB family receptor dimerization in glioblastoma—An eTag assay analysis of 23 cases," American Society of Cancer Oncology (ASCO) Annual Meeting, Jun. 2-6, 2006, Atlanta, GA (Poster 1582).

Jimeno, A. et al., "Combined targeted therapy shows increased efficacy in a novel in vivo pancreas cancer model," American Association for Cancer Research (AACR) Annual Meeting, Apr. 1-6, 2006, Washington, D.C. (Abstract 2181).

Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA: Abstract A121.

Dua, R. et al., "ErbB/HER pathway profiling in formalin-fixed paraffin embedded preclinical xenograft models using multiplexed proximity-based assays," International Conference on Molecular Targets and Cancer Therapeutics, AACR-NCI-EORTC, Nov. 14-18, 2005, Philadelphia, PA (Poster A121).

Shi, Y., "Analysis of ErbB/HER receptor pathways in formalin-fixed and paraffin-embedded cancer cell lines using multiplexed eTag™ assays," 2005 J. Clin. Oncol. 23(16S) (Jun. 1 Suppl.): Abstract 9565.

Shi, Y.. et al., "Analysis of ErbB/HER receptor pathways in formalin-fixed and paraffin-embedded cancer cell lines using multiplexed eTag™ assays," American Society of Clinical Oncology (ASCO) Annual Meeting, May 13-17, 2007, Orlando, FL (Poster 9565).

Mukherjee, A., "The Use of ErbB/HER Activation Status as Prognostic Markers in Breast Cancer Patients Treated with Trastuzumab," 2005 J. Clin. Oncol. 23(16S) (Jun. 1 Suppl.): Abstract 553.

Mukherjee, A. et al., "The use of ErbB activation Status as Prognostic Markers in Breast Cancer Patients Treated with Trastuzumab," American Society of Clinical Oncology (ASCO) Annual Meeting, May 13-17, 2005, Orlando, FL (Poster 553).

Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA: Abstract A127.

Salimi-Moosavi, H. et al., "Effect of Erbitux, Erlotinib, Gefitinib, and Rapamycin on the inhibition of EGFR dimer formation and downstream signaling pathways in different cancer cell lines," International Conference on Molecular Targets and Cancer Therapeutics, AACR-NCI-EORTC, Nov. 14-18, 2005, Philadelphia, PA (Poster A127).

Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA: Abstract A124.

Salimi-Moosavi, H. et al., "Effect of gefitinib on EGFR activation in lung cancer cell lines," Intl. Conference on Molecular Targets and Cancer Therapeutics, AACR-NCI-EORTC, Nov. 14-18, 2005, Philadelphia, PA (Poster A124).

Salimi-Moosavi, H. et al., "IC50 determination for receptor-targeted compounds and downstream signaling," In: Proc. Am. Assoc. Cancer Res. AACR, Apr. 16-20, 2005, Anaheim, CA: Abstract 4567.

Shi, Y. et al., "Multiplexed assay for assessing ErbB/HER receptor pathways in formalin-fixed and paraffin-embedded cancer cell lines," In: Proc. Am. Assoc. Cancer Res. AACR Apr. 16-20, 2005 Anaheim, CA: Abstract 5762.

Shi, Y. et al., "Multiplexed assay for assessing ErbB/HER receptor pathways in formalin-fixed and paraffin-embedded cancer cell lines," American Association for Cancer Research (AACR) Annual Meeting, Apr. 16-20, 2005, Anaheim, CA (Poster 5762).

Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA: Abstract B17.

Sperinde, J. et al., "Multiplex detection of vascular endothelial growth factor receptor 2 (VEGFR2) homodimers and phosphorylation in xenografts, human tumor tissues and formalin-fixed paraffin-embedded (FFPE) samples from cell lines using the eTag™ assay system," International Conference on Molecular Targets and Cancer Therapeutics, Nov. 14-18, 2005, Philadelphia, PA (Poster B17).

Toi, M. et al., "The Correlation of ErbB/HER Activation Status with Breast Cancer Patient Response to Trastuzumab," National Cancer Research Cancer Institute (NCRI) Conference, Oct. 2-5, 2005, Birmingham, UK (Poster 1025).

Yatabe, Yet al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA: Abstract A123.

Yatabe, Yet al., "Application of Proximity Based Assay to Develop Algorithms That Correlate ErbB/HER Pathway Profiling and Predictive Response to EGFR/HER1 Targeted Therapy in Lung Cancer Patients," Intl. Conference on Molecular Targets and Cancer Therapeutics, Nov. 14-18, 2005, Philadelphia, PA (Poster A123).

Duchnowska, R. et al., "Correlation between quantitative HER2 protein expression and risk of brain metastasis in HER2-positive advanced breast cancer patients receiving trastuzumab-containing therapy," Oncologist 17(1):26-35 (2012) (pub. online Jan. 10, 2012).

Han, S-W, "Correlation of HER2, p95HER2 and HER3 expression and treatment outcome of lapatinib plus capecitabine in HER2-positive metastatic breast cancer," PLoS ONE 7(7):e39943 (2012) (pub. online Jul. 27, 2012).

Bates, M. et al., "Identification of a Subpopulation of Metastatic Breast Cancer Patients with Very High HER2 Expression Levels and Possible resistance to Trastuzumab," Ann. Oncol., 22(9):2014-2020 (2011) (pub. online Feb. 11, 2011).

Defazio-Eli, L. et al., "Quantitative assays for the measurement of HER1-HER2 heterodimerization and phosphorylation in cell lines and breast tumors: applications for diagnostics and targeted drug mechanism of action," Breast Canc. Res. 13:R44 (2011) (pub. Apr. 15, 2011).

Dua, R. et al., "Detetion of hepatocyte growth factor (HGF) ligand-C-met receptor activation in formalin-fixed, paraffin-embedded specimans by a novel proximity assay," PLOS One 6(1): e15932 (2011) (pub. online Jan. 21, 2011).

Joensuu, H. et al., "Very high quantitative tumor HER2 content and outcome in early breast cancer," Ann. Oncol. 22(9): 2007-2013 (2011) (pub. online Feb. 1, 2011).

Ghosh, M. et al., "Trastuzumab has preferential activity against breast cancers driven by HER2 homodimers," Cancer Res. 71(5):1871 (2011) (pub. online Feb. 15, 2011).

Mukherjee, A. et al., "Profiling the HER3/PI3K Pathway in Breast Tumors Using Proximity-Directed Assays Identifies Correlations between Protein Complexes and Phosphoproteins," PLoS One 6(1): e16443 (2011) (pub. online Jan. 28, 2011).

Dua, R. et al., "EGFR over-expression and activation in high HER2, ER negative breast cancer cell lines induces trastuzumab resistance," Breast Cancer Res. Treat. 122(3):6850697 (2010) (pub. online Oct. 27, 2009).

Jain, A. et al., "HER kinase axis receptor dimer partner switching occurs in response to EGFR tyrosine kinase inhibition despite failure to block cellular proliferation," Cancer Res. 70(5):1989-1999 (2010) (pub. online Feb. 16, 2010).

Huang, Q. et al., "Comparison of central HER2 testing with quantitative total HER2 expression and HER2 homodimer measurement using a novel proximity based assay," Am. J. Clin. Pathol. 134:303-311 (2010) (pub. Aug. 2010).

Larson, J.S. et al., "Analystical validation of a highly senstivie, accurate, and reproducible assay (HERmark®) for the measurement of HER2 total protein and HER2 homodimers in FFPE breast cancer tumor specimens," Pathol. Res. Intl, 2010: Article ID 814176 (2010) (pub. online Jun. 28, 2010).

Lipton, A. et al., "Quantitative HER2 protein levels predict outcome in fluorescence in situ hybridization-positive patients with metastatic breast cancer treated with trastuzumab," Cancer 116:5168-5178 (2010) (pub. online Nov. 3, 2010).

Mamluk, R. et al., "Anti-tumor effect of CT-322 as an adnectin inhibitor of vascular endothelial growth factor receptor-2," MAbs 2(2):199-208 (2010) (pub. online Mar. 1, 2010).

Sperinde, J. et al., "Quantitation of p95HER2 in paraffin sections by using a p95-specific antibody and correlation with outcome in a cohort of trastuzumab-treated breast cancer patients," Clin. Canc. Res. 16(16):4226-4235 (2010) (pub. online Jul. 27, 2010).

Toi, M. et al., "Differential survival following trastuzumab treatment based on quantitative HER2 expression and HER2 homodimers in a clinic-based cohort of patients with metastatic breast cancer," BMC Cancer 10:56 (2010) (pub. Feb. 23, 2010) (10 pages).

Desmedt, C. et al., "Quantitation of HER2 expression or HER2:HER2 dimers and differential survival in a cohort of metastatic breast cancer patients carefully selected for trastuzumab treatment primarily by FISH," Diagn. Mol. Pathol. 18(1):22-29 (2009) (pub. Mar. 2009).

Shi, Y. et al., "A novel proximity assay for the detection of proteins and protein complexes: quantitation of HER1 and HER2 total protein expression and homodimerization in formalin-fixed, paraffin-embedded cell lines and breast cancer tissue," Diagn. Mol. Pathol. 18(1):11-21 (2009) (pub. Mar. 2009).

Chan-Hui, P-Y et al., "Applications of eTag™ assay platform to systems biology approaches in molecular oncology and toxicology studies," Clin. Immun. 111:162-174 (2004) (pub. online Mar. 11, 2004).

Tian, H. et al., "Multiplex mRNA assay using electrophoretic tags for high-throughput gene expression analysis," Nucl. Acid Res. 32(16):e126 (pub. online Sep. 8, 2004).

ELISA: Cell Line Panel

| Cell Line | HER3 (ng/mg) |
|---|---|
| 293H3-Clone 13 | 967 |
| 293H3-Clone 1 | 460 |
| 293H3-Clone 4 | 314 |
| 293H3-Clone 10 | 82 |
| Wild Type 293 | 1.0 |

| Peptide Sequence | Length | HER3 Amino Acids | Clone ID | ELISA/IHC/VeraTag |
|---|---|---|---|---|
| LGSALSLPVLNRPRGTGSQSLLSP | 24 | 1027-1050 | | |
| SAYHSQRHSLLTPVTPLSP | 19 | 1130-1148 | A2 | Positive |
| VGSDLSASLGSTQSCPLHPVPI | 22 | 1227-1248 | | |
| CQGPGHQAPHVHYARLKTLRS | 21 | 1296-1315 | | |
| LEEVELEPELDLDLDLEAE | 19 | 1000-1018 | | |
| CFDNPDYWHSRLFPKANA | 18 | 1323-1339 | B9A11, B11 | Positive |
| CPDYWHSRLFPKANAQRT | 18 | 1326-1342 | F9, F9B10 | Positive |
| CFPKANAQRT | 10 | 1334-1342 | F9 | Positive |

Figure 2A

| Cell Line | IHC Score | VeraTag | ELISA [HER3] ng/mg | Flow Cytometry (Receptors/cell) |
|---|---|---|---|---|
| 293H3-Clone 1 | 3+ | 10.01 | 502.2 | 188,045 |
| MDA-MB-453 | 1+ | 1.00 | 46.2 | 25,716 |
| MDA-MB-468 | 0 | 0.24 | 2.5 | 5669 |
| SKOV3 | 0 | 0.06 | 0.4 | 500 |

IHC

```
                        SEQUENCE LISTING

<160> NUMBER OF SEQ ID NOS: 24

<210> SEQ ID NO 1
<211> LENGTH: 24
<212> TYPE: PRT
<213> ORGANISM: Artificial Sequence
<220> FEATURE:
<223> OTHER INFORMATION: Note: Artificial = synthetic construct

<400> SEQUENCE: 1

Leu Gly Ser Ala Leu Ser Leu Pro Val Leu Asn Arg Pro Arg Gly Thr
1               5                   10                  15

Gly Ser Gln Ser Leu Leu Ser Pro
            20

<210> SEQ ID NO 2
<211> LENGTH: 19
<212> TYPE: PRT
<213> ORGANISM: Artificial Sequence
<220> FEATURE:
<223> OTHER INFORMATION: Note: Artificial = synthetic construct

<400> SEQUENCE: 2

Ser Ala Tyr His Ser Gln Arg His Ser Leu Leu Thr Pro Val Thr Pro
1               5                   10                  15

Leu Ser Pro

<210> SEQ ID NO 3
<211> LENGTH: 22
<212> TYPE: PRT
<213> ORGANISM: Artificial Sequence
<220> FEATURE:
<223> OTHER INFORMATION: Note: Artificial = synthetic construct

<400> SEQUENCE: 3

Val Gly Ser Asp Leu Ser Ala Ser Leu Gly Ser Thr Gln Ser Cys Pro
1               5                   10                  15

Leu His Pro Val Pro Ile
            20

<210> SEQ ID NO 4
<211> LENGTH: 21
<212> TYPE: PRT
<213> ORGANISM: Artificial Sequence
<220> FEATURE:
<223> OTHER INFORMATION: Note: Artificial = synthetic construct

<400> SEQUENCE: 4

Cys Gln Gly Pro Gly His Gln Ala Pro His Val His Tyr Ala Arg Leu
1               5                   10                  15
```

```
Lys Thr Leu Arg Ser
            20

<210> SEQ ID NO 5
<211> LENGTH: 19
<212> TYPE: PRT
<213> ORGANISM: Artificial Sequence
<220> FEATURE:
<223> OTHER INFORMATION: Note: Artificial = synthetic construct

<400> SEQUENCE: 5

Leu Glu Glu Val Glu Leu Glu Pro Glu Leu Asp Leu Asp Leu Asp Leu
1               5                   10                  15

Glu Ala Glu

<210> SEQ ID NO 6
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 6

Cys Phe Asp Asn Pro Asp Tyr Trp His Ser Arg Leu Phe Pro Lys Ala
1               5                   10                  15

Asn Ala

<210> SEQ ID NO 7
<211> LENGTH: 18
<212> TYPE: PRT
<213> ORGANISM: Artificial Sequence
<220> FEATURE:
<223> OTHER INFORMATION: Note: Artificial = synthetic construct

<400> SEQUENCE: 7

Cys Pro Asp Tyr Trp His Ser Arg Leu Phe Pro Lys Ala Asn Ala Gln
1               5                   10                  15

Arg Thr

<210> SEQ ID NO 8
<211> LENGTH: 10
<212> TYPE: PRT
<213> ORGANISM: Artificial Sequence
<220> FEATURE:
<223> OTHER INFORMATION: Note: Artificial = synthetic construct

<400> SEQUENCE: 8

Cys Phe Pro Lys Ala Asn Ala Gln Arg Thr
1               5                   10

<210> SEQ ID NO 9
<211> LENGTH: 132
<212> TYPE: PRT
<213> ORGANISM: Artificial Sequence
<220> FEATURE:
<223> OTHER INFORMATION: Note: Artificial = synthetic construct

<400> SEQUENCE: 9

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Leu Ser Cys Lys Ser Ser Gln Ser
        35                  40                  45
```

```
Leu Leu Asn Ser Arg Thr Arg Lys Asn Tyr Leu Ala Trp Tyr Gln Gln
     50                  55                  60

Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Val Ser Ser Val Gln Ala Glu Asp Leu Ala Val Tyr
             100                 105                 110

Tyr Cys Lys Gln Ser Tyr Asn Leu Trp Thr Phe Gly Gly Gly Thr Lys
         115                 120                 125

Leu Glu Ile Lys
        130
```

<210> SEQ ID NO 10
<211> LENGTH: 132
<212> TYPE: PRT
<213> ORGANISM: Artificial Sequence
<220> FEATURE:
<223> OTHER INFORMATION: Note: Artificial = synthetic construct

<400> SEQUENCE: 10

```
Met Arg Cys Leu Ala Glu Phe Leu Gly Leu Leu Val Leu Trp Ile Pro
 1               5                  10                  15

Gly Ala Ile Gly Asp Ile Val Met Thr Gln Ala Pro Ser Val Pro
             20                  25                  30

Val Thr Pro Gly Glu Ser Val Ser Ile Ser Cys Arg Ser Ser Lys Ser
         35                  40                  45

Leu Leu Gln Asn Asn Gly Asn Thr Tyr Leu Tyr Trp Phe Leu Gln Arg
     50                  55                  60

Pro Gly Gln Ser Pro Gln Leu Leu Ile Tyr Arg Met Ser Asn Leu Ala
 65                  70                  75                  80

Ser Gly Val Pro Asp Arg Phe Ser Gly Ser Gly Ser Gly Thr Ala Phe
                 85                  90                  95

Thr Leu Arg Ile Ser Arg Val Glu Ala Glu Asp Val Gly Val Tyr Tyr
             100                 105                 110

Cys Met Gln His Leu Glu Tyr Pro Leu Thr Phe Gly Ala Gly Thr Lys
         115                 120                 125

Leu Gly Leu Lys
        130
```

<210> SEQ ID NO 11
<211> LENGTH: 139
<212> TYPE: PRT
<213> ORGANISM: Artificial Sequence
<220> FEATURE:
<223> OTHER INFORMATION: Note: Artificial = synthetic construct

<400> SEQUENCE: 11

```
Met Glu Cys Asn Trp Ile Leu Pro Phe Ile Leu Ser Val Thr Ser Gly
 1               5                  10                  15

Val Tyr Ser Glu Val Gln Leu Gln Gln Pro Gly Thr Val Leu Ala Arg
             20                  25                  30

Pro Gly Ala Ser Val Arg Met Ser Cys Lys Ala Ser Gly Tyr Thr Phe
         35                  40                  45

Thr Ser Tyr Trp Met His Trp Val Lys Gln Arg Pro Gly Gln Gly Leu
     50                  55                  60

Glu Trp Ile Gly Ala Ile Tyr Pro Gly Asn Ser Asp Thr Arg Asp Asn
 65                  70                  75                  80
```

Gln Lys Phe Lys Gly Lys Ala Glu Leu Thr Ala Val Thr Ser Ala Ser
                85                  90                  95

Thr Ala Tyr Met Glu Leu Ser Ser Leu Thr Asn Glu Asp Ser Ala Val
            100                 105                 110

Tyr Tyr Cys Thr Ser Tyr Tyr Phe Asp Gly Ala Gly Tyr Phe Asp Phe
            115                 120                 125

Trp Gly Gln Gly Thr Thr Leu Thr Val Ser Ser
        130                 135

<210> SEQ ID NO 12
<211> LENGTH: 142
<212> TYPE: PRT
<213> ORGANISM: Artificial Sequence
<220> FEATURE:
<223> OTHER INFORMATION: Note: Artificial = synthetic construct

<400> SEQUENCE: 12

Met Glu Trp Ser Trp Val Phe Leu Phe Leu Leu Ser Val Ile Ala Ser
1               5                   10                  15

Val Gln Ser Gln Val Gln Leu Gln Gln Ser Gly Ala Glu Val Val Arg
            20                  25                  30

Pro Gly Ala Ser Val Thr Leu Ser Cys Lys Ala Ser Ala Tyr Thr Phe
        35                  40                  45

Thr Asp Tyr Glu Leu His Trp Met Arg Gln Thr Pro Val His Gly Leu
    50                  55                  60

Glu Trp Ile Gly Ala Ser Asp Pro Glu Thr Gly Gly Ser Ala Tyr Asn
65                  70                  75                  80

Gln Lys Phe Lys Gly Lys Ala Ile Leu Thr Ala Asp Lys Ser Ser Ser
                85                  90                  95

Thr Ala Phe Met Glu Leu Arg Ser Leu Thr Ser Glu Asp Ser Ala Val
            100                 105                 110

Tyr Phe Cys Thr Arg Arg Ile Phe Tyr Phe Gly Ser Arg Gly Asp Phe
            115                 120                 125

Phe Asp Tyr Trp Gly Gln Gly Thr Ser Leu Thr Val Ser Ser
        130                 135                 140

<210> SEQ ID NO 13
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 13

Lys Ser Ser Gln Ser Leu Leu Asn Ser Arg Thr Arg Lys Asn Tyr Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: Note: Artificial = synthetic construct

<400> SEQUENCE: 14

Trp Ala Ser Thr Arg Glu Ser
1               5

<210> SEQ ID NO 15

```
<211> LENGTH: 8
<212> TYPE: PRT
<213> ORGANISM: Artificial Sequence
<220> FEATURE:
<223> OTHER INFORMATION: Note: Artificial = synthetic construct

<400> SEQUENCE: 15

Lys Gln Ser Tyr Asn Leu Trp Thr
1               5

<210> SEQ ID NO 16
<211> LENGTH: 5
<212> TYPE: PRT
<213> ORGANISM: Artificial Sequence
<220> FEATURE:
<223> OTHER INFORMATION: Note: Artificial = synthetic construct

<400> SEQUENCE: 16

Ser Tyr Trp Met His
1               5

<210> SEQ ID NO 17
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 17

Ala Ile Tyr Pro Gly Asn Ser Asp Thr Arg Asp Asn Gln Lys Phe Lys
1               5                   10                  15

Gly

<210> SEQ ID NO 18
<211> LENGTH: 11
<212> TYPE: PRT
<213> ORGANISM: Artificial Sequence
<220> FEATURE:
<223> OTHER INFORMATION: Note: Artificial = synthetic construct

<400> SEQUENCE: 18

Tyr Tyr Phe Asp Gly Ala Gly Tyr Phe Asp Phe
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Note: Artificial = synthetic construct

<400> SEQUENCE: 19

Arg Ser Ser Lys Ser Leu Leu Gln Asn Asn Gly Asn Thr Tyr Leu Tyr
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Note: Artificial = synthetic construct

<400> SEQUENCE: 20

Arg Met Ser Asn Leu Ala Ser
1               5

<210> SEQ ID NO 21
```

```
<211> LENGTH: 9
<212> TYPE: PRT
<213> ORGANISM: Artificial Sequence
<220> FEATURE:
<223> OTHER INFORMATION: Note: Artificial = synthetic construct

<400> SEQUENCE: 21

Thr Met Gln His Leu Glu Tyr Pro Leu
1               5

<210> SEQ ID NO 22
<211> LENGTH: 5
<212> TYPE: PRT
<213> ORGANISM: Artificial Sequence
<220> FEATURE:
<223> OTHER INFORMATION: Note: Artificial = synthetic construct

<400> SEQUENCE: 22

Asp Tyr Glu Leu His
1               5

<210> SEQ ID NO 23
<211> LENGTH: 17
<212> TYPE: PRT
<213> ORGANISM: Artificial Sequence
<220> FEATURE:
<223> OTHER INFORMATION: Note: Artificial = synthetic construct

<400> SEQUENCE: 23

Ala Ser Asp Pro Glu Thr Gly Gly Ser Ala Tyr Asn Gln Lys Phe Lys
1               5                   10                  15

Gly

<210> SEQ ID NO 24
<211> LENGTH: 14
<212> TYPE: PRT
<213> ORGANISM: Artificial Sequence
<220> FEATURE:
<223> OTHER INFORMATION: Note: Artificial = synthetic construct

<400> SEQUENCE: 24

Arg Ile Phe Tyr Phe Gly Ser Arg Gly Asp Phe Phe Asp Tyr
1               5                   10
```

METHODS OF DETERMINING PATIENT RESPONSE BY MEASUREMENT OF HER-3

CROSS-REFERENCE TO RELATED APPLICATIONS

This application claims the benefit of and priority under 35 USC §119(e) to U.S. Provisional Application No. 61/176,630, filed May 8, 2009, U.S. Provisional Application No. 61/187,962, filed Jun. 17, 2009, and U.S. Provisional Application 61/145,029, filed Jan. 15, 2009, which are incorporated by reference in their entireties.

BACKGROUND OF THE INVENTION

A biomarker generally has a characteristic that can be objectively measured and evaluated as an indicator of normal biological processes, pathogenic processes or pharmacological responses to a therapeutic intervention. See Atkinson et al., 2001, *Clin. Pharmacol. Ther.* 69:89-95. Biomarkers vary widely in nature, ease of measurement and correlation with physiological states of interest. See, e.g., Frank et al., 2003, *Nature Reviews Drug Discovery* 2:566-580. It is widely believed that the development of new validated biomarkers will lead both to significant reductions in healthcare and drug development costs and to significant improvements in treatment for a wide variety of diseases and conditions. Thus, a great deal of effort has been directed to using new technologies to find new classes of biomarkers. See, e.g., Petricoin et al., 2002, *Nature Reviews Drug Discovery*, 1:683-695; and Sidransky, 2002, *Nature Reviews Cancer* 2:210-219; Ludwig and Weinstein, 2005, *Nature Reviews Cancer* 5:845-856; Lee et al., 2007, *Adv. Cancer. Res.*, 96:269-298; Dhani and Siu, 2008, *Cancer Metastasis Rev.* 27:339-349; Carden et al., 2009, *Clin. Pharmacol. Ther.* 85:131-133.

The interactions of cell surface membrane components play crucial roles in transmitting extracellular signals to a cell in normal physiology and in disease conditions. In particular, many types of cell surface receptors undergo dimerization, oligomerization or clustering in connection with the transduction of an extracellular event or signal into a cellular response, such as, e.g., proliferation, increased or decreased gene expression or the like. See, e.g., George et al., 2002, *Nature Reviews Drug Discovery* 1:808-820; Mellado et al, 2001, *Ann. Rev. Immunol.* 19:397-421; Schlessinger, 2000, *Cell* 103:211-225; and Yarden, 2001, *Eur. J. Cancer* 37:S3-S8. The role of such events in diseases, such as cancer, has been the object of intense research and has led to the development of several new drugs and drug candidates. See, e.g., Herbst and Shin, 2002, *Cancer* 94:1593-1611; Yarden and Sliwkowski, 2001, *Nature Reviews Molecular Cell Biology* 2:127-137; McCormick, 1999, *Trends in Cell Biology* 9:53-56 (1999); and Blume-Jensen and Hunter, 2001, *Nature* 411:355-365.

Expression levels of individual cell surface receptors, such as Her-2 in breast cancer, have been used as biomarkers, especially to determine patient prognosis or whether a patient will or will not respond to certain treatments. In addition, oncogenic tyrosine kinases such as members of the epidermal growth factor receptor family have provided targets for drug development. However, the tyrosine kinase inhibitors targeted to EGFR and Her-2 have shown less clinical efficacy than anticipated from promising preclinical studies, which has led to interest in other EGFR-family members, such as Her-3, in part for prognostic value as biomarkers and in part because of interactions with other family members, leading to potential new drug targets. See Menendez and Lupu, 2007, *Breast Cancer Research* 9:111; Lee-Hoeflich et al., 2008, *Cancer Res* 68:5878-5887; Fuchs et al., 2006, *Anticancer Res.* 26:4397-4402; Sergina et al., 2007, *Nature* 445:437-441; and Tovey et al., 2006, *J. Pathol.* 210:358-362.

Her-3 is sometimes over-expressed in breast cancer, colorectal cancer, ovarian cancer, bladder cancer, prostate cancer, non-small cell lung cancer, melanoma, pharyngeal cancer, pancreatic cancer, esophageal cancer, glioma, biliary tract carcinoma, cholangiocarcinoma, gastric cancer, endometrial cancer, gall bladder cancer, squamous cell carcinoma or basal cell carcinoma. Conventional immunohistochemical (IHC) or fluorescence in situ hybridization (FISH) analyses have been used to detect Her-3 over-expression. Unfortunately, IHC and FISH have certain limitations as diagnostic tools in that they are not necessarily accurate and also prone to different interpretations by different laboratory personnel. There are currently no methods for accurately assessing the level of Her-3. The advent of a quantitative method for measuring Her-3 would facilitate the ability to accurately determine a cancer patient's prognosis and/or whether a patient is likely to respond to a certain treatment. See Mosesson et al., 2004, *Semin. Cancer. Biol.* 14:262-270.

SUMMARY OF THE INVENTION

In a first aspect, the invention is drawn to a method of measuring and/or quantifying the presence and/or amount of Her-3 and/or Her-3 in a complex in a sample, the method comprising providing a sample and determining the presence and/or quantity of Her-3 and/or Her-3 in a complex in the sample. In certain embodiments, the amount of Her-3 is above a first threshold, such that the sample is stratified as having a "high" amount of Her-3 (e.g., either total Her-3 and/or Her-3 homodimers and/or Her-3 heterodimers). In some embodiments the first threshold value for Her-3 is a total Her-3 (H3T) of $\geq 0.158$ and a low Her-3 value is below this threshold. Or, other ranges may be used depending upon the patient cohort and/or the significant event being monitored. Thus, each of the threshold values and/or threshold ranges described herein may vary by about 0.5 log units or less on a log scale and/or 25% or less on a linear scale (i.e., be $\leq 25\%$ larger and/or $\leq 25\%$ smaller than the specific ranges disclosed herein), or by about 20% or less, or by about 15% or less, or by about 10% or less, or by about 5% or less.

In a preferred embodiment, the sample is a biological sample. In a preferred embodiment, the sample is a tissue sample. In a preferred embodiment, the sample is a fresh tissue sample, a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate from a fresh or frozen tumor sample. In a preferred embodiment, the sample is an FFPE or solubilized FFPE sample. In a preferred embodiment, the sample comprises a breast cancer sample. In a certain embodiments, the breast cancer is early stage (i.e., adjuvant) breast cancer or metastatic breast cancer.

In certain embodiments of each of the methods and/or aspects of the invention as disclosed herein, the method comprises detection of other biomarkers in the sample. For example, other biomarkers such as Her-2 and/or p95 may be measured. Or, other biomarkers such as can be at least one of FOXM1, PRAME, Bcl2, STK15, CEGP1, Ki-67, GSTM1, CA9, PR, BBC3, NME1, SURV, GATA3, TFRC, YB-1, DPYD, GSTM3, RPS6 KB1, Src, Chk1, ID1, EstR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, CDH1, HIF1α, IGFBP3; CTSB, Her3 or DIABLO. In certain embodiments, the other biomarker can be VEGF, CD31, KDR, p95, or Her-2.

In certain embodiments of each of the methods and/or aspects of the invention as disclosed herein, the level of Her-2 expression in the breast cancer is high. In certain embodiments, high Her-2 expression is a log 10H2T$\geq$ about 1.14-1.25. In certain embodiments, the high Her-2 expression comprises expression that is very high and/or moderately high. In certain embodiments, the very high Her-2 expression is a log 10H2T$\geq$ about 1.84-2.21. In certain embodiments of each of the methods disclosed herein, the moderately high expression is between 1.14-1.25 and 1.84-2.21 (i.e., $\geq$1.14-1.25 and $\leq$1.84-2.21). Or, other ranges may be used depending upon the patient cohort and/or the significant event being monitored. Thus, each of the threshold values and/or threshold ranges described herein may vary by about 0.5 log units or less on a log scale and/or 25% or less on a linear scale (i.e., be $\leq$25% larger and/or $\leq$25% smaller than the specific ranges disclosed herein), or by about 20% or less, or by about 15% or less, or by about 10% or less, or by about 5% or less.

Also, in certain embodiments of each of the methods and/or aspects of the invention as disclosed herein, the level of p95 may be evaluated as either high or low. In some embodiments the first threshold value for p95 is a total p95 value of $\geq$90 (on a linear scale) and a low p95 value is below this threshold. Or, other ranges may be used depending upon the patient cohort and/or the significant event being monitored. Thus, each of the threshold values and/or threshold ranges described herein may vary by about 0.5 log units or less on a log scale and/or 25% or less on a linear scale (i.e., be $\leq$25% larger and/or $\leq$25% smaller than the specific ranges disclosed herein), or by about 20% or less, or by about 15% or less, or by about 10% or less, or by about 5% or less.

In certain embodiments, if the level of Her-3 is high, the patient is less likely or unlikely to respond to the targeted therapy. In certain embodiments, if the level of Her-3 is low, the patient is more likely to respond to the targeted therapy. In certain embodiments, the therapy is a Her-acting agent. In certain embodiments, the therapy is at least one of a Her-2 acting agent or a Her-3-targeted agent.

Thus, in certain embodiments of each of the methods and aspects of the invention as disclosed herein, the method comprises measuring in a biological sample from the subject's cancer an amount of Her-2 and/or Her-2 homodimers, wherein if the amount of Her-2 and/or Her-2 homodimers is moderately high and Her-3 expression is low, then the patient is likely to respond to the Her-2 acting agent and/or the patient has a long time course. In certain embodiments, the method comprises measuring in a biological sample from the subject's cancer an amount of Her-2 and/or Her-2 homodimers, wherein if the amount of Her-2 and/or Her-2 homodimers is moderately high and Her-3 expression is high, then the patient is unlikely to respond to the Her-2 acting agent and/or the patient has a short time course.

Additionally and/or alternatively, in certain embodiments of each of the methods and aspects of the invention as disclosed herein, the method comprises measuring in a biological sample from the subject's cancer an amount p95, wherein if the amount of p95 and Her-3 expression is low, then the patient is likely to respond to the therapeutically acting agent and/or the patient has a long time course. In an embodiment, the patient also has a high (or moderately high) level of Her-2. In certain embodiments, the method comprises measuring in a biological sample from the subject's cancer an amount of Her-2 and/or Her-2 homodimers, wherein if the amount of Her-2 and/or Her-2 homodimers is high and/or moderately high and Her-3 expression and/or p95 expression is high, then the patient is unlikely to respond to the Her-2 acting agent and/or the patient has a short time course.

In a preferred embodiment, the sample is a blood, plasma or lymph sample. In a preferred embodiment, the blood or plasma sample contains circulating tumor cells. In a preferred embodiment, the sample comprises cell lines. In a preferred embodiment, the measurement may be quantitative across a wide dynamic range.

In a preferred embodiment, the method comprises mixing the sample with a binding compound and determining the presence and/or quantity of the binding compound bound to Her-3 and/or Her-3 in a complex. In a preferred embodiment, the binding compound binds specifically to Her-3. In a preferred embodiment, the binding compound comprises an antibody. In a preferred embodiment, the antibody is raised against one of the peptides having SEQ ID NOs:1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively. In a preferred embodiment, the antibody is the antibody with the amino acid sequence having SEQ ID NOs:9 and 11 as set forth in Table 1 (see Detailed Description) for the light and heavy chains, respectively, and/or SEQ ID NOs:10 and 12 as set forth in Table 1 (see Detailed Description) for the light and heavy chains, respectively. In a preferred embodiment, the method comprises mixing (i) a sample that may contain Her-3 and/or Her-3 in a complex; (ii) a proximity probe that is capable of binding Her-3, the proximity probe having an effective proximity and (iii) at least one binding compound, the at least one binding compound being capable of binding Her-3 and having one or more signaling molecules attached, wherein binding of the proximity probe and the binding compound within the effective proximity produces a signal from the molecular tags that correlates with the presence and/or quantity of Her-3 and/or Her-3 in a complex. In a preferred embodiment, the proximity probe and/or binding compound is capable of binding specifically to Her-3 or the at least one other analyte. In a preferred embodiment, the proximity probe and/or binding compound further comprises an antibody and each antibody can bind to a specific epitope on Her-3. In a preferred embodiment, the antibody is raised against one of the peptides having SEQ ID NOs:1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively. In a preferred embodiment, the antibody is the antibody with the amino acid sequence having SEQ ID NOs:9 and 11 as set forth in Table 1 (see Detailed Description) for the light and heavy chains, respectively, and/or SEQ ID NOs:10 and 12 as set forth in Table 1 (see Detailed Description) for the light and heavy chains, respectively. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample or solubilized FFPE sample. In a preferred embodiment, the sample is a blood, plasma or lymph sample. In a preferred embodiment, the blood or plasma sample contains circulating tumor cells. In a preferred embodiment, the sample comprises cell lines. In a preferred embodiment, the measurement may be quantitative across a wide dynamic range. In a preferred embodiment, the wide dynamic range is approximately 2 logs. In a more preferred embodiment, the wide dynamic range is about 1-1.5 logs in breast cancer samples. In a preferred embodiment, the method provides a quantitative continuum of Her-3 expression. In a preferred embodiment, the measurement or quantity is sensitive to at least about 1000 receptors per cell to about 200,000 receptors per cell as determined by accuracy studies utilizing well-characterized cell line models and cross-validating technologies such as ELISA and flow cytometry. In a preferred embodiment, the measurement or quantity is sensitive to at least about 5000 receptors per cell to about 200,000 receptors per cell. In a preferred embodiment, the measurement or quantity is sensitive to at least about 10,000 receptors per cell to about 200,000 receptors per cell. In a preferred embodiment, the measurement or quantity is sensitive to at least about 25,000 receptors per cell to about 200,000 receptors per cell. In a preferred embodiment, the measurement is specific as determined using isotype control antibodies and comparison with conventional IHC methods.

In a further preferred embodiment, the proximity probe comprises an antibody and a first nucleic acid and the binding compound comprises an antibody and a second nucleic acid, wherein the first and the second nucleic acids are complementary to each other and able to hybridize to determine the effective proximity and produce the signal, directly or indirectly, through hybridization. In a preferred embodiment, the proximity probe and/or binding compound is capable of binding specifically to Her-3. In a preferred embodiment, the binding compound and/or the proximity probe further comprises an antibody and each antibody binds to a different epitope on Her-3. In a preferred embodiment, the antibody is raised against one of the peptides having SEQ ID NOs: 1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively. In a preferred embodiment, the antibody is the antibody with the amino acid sequence having SEQ ID NOs:9 and 11 as set forth in Table 1 (see Detailed Description) for the light and heavy chains, respectively, and/or SEQ ID NOs:10 and 12 as set forth in Table 1 (see Detailed Description) for the light and heavy chains, respectively. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample or solubilized FFPE sample. In a preferred embodiment, the sample is a blood, plasma or lymph sample. In a preferred embodiment, the blood or plasma sample contains circulating tumor cells. In a preferred embodiment, the sample comprises cell lines. In a preferred embodiment, the measurement may be quantitative across a wide dynamic range. In a preferred embodiment, the wide dynamic range is about 2 logs. In a more preferred embodiment, the wide dynamic range is about 1-1.5 logs in breast cancer samples. In a preferred embodiment, the method provides a quantitative continuum of Her-3 expression. In a preferred embodiment, the measurement or quantity is sensitive to at least about 1000 receptors per cell to about 200,000 receptors per cell as determined by accuracy studies utilizing well-characterized cell line models and cross-validating technologies such as ELISA and flow cytometry. In a preferred embodiment, the measurement or quantity is sensitive to at least about 5000 receptors per cell to about 200,000 receptors per cell. In a preferred embodiment, the measurement or quantity is sensitive to at least about 10,000 receptors per cell to about 200,000 receptors per cell. In a preferred embodiment, the measurement or quantity is sensitive to at least about 25,000 receptors per cell to about 200,000 receptors per cell. In a preferred embodiment, the measurement is specific as determined by using isotype control antibodies and comparison with conventional IHC methods.

In a preferred embodiment, the proximity probe comprises a cleaving probe that has a cleavage-inducing moiety and the at least one binding compound has one or more molecular tags attached to the binding compound by a cleavable linkage, wherein the cleavable linkage may be cleaved within the effective proximity, producing a signal that correlates with the presence and/or quantity of Her-3. In a preferred embodiment, the cleaving probe and/or binding compound is capable of binding specifically to Her-3. In a preferred embodiment, the binding compound and/or the proximity probe further comprises an antibody and each antibody binds to a different epitope on Her-3. In a preferred embodiment, the antibody is raised against one of the peptides having SEQ ID NOs: 1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively. In a preferred embodiment, the antibody is the antibody with the amino acid sequence having SEQ ID NOs:9 and 11 as set forth in Table 1

(see Detailed Description) for the light and heavy chains, respectively, and/or SEQ ID NOs:10 and 12 as set forth in Table 1 (see Detailed Description) for the light and heavy chains, respectively. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample. In a preferred embodiment, the sample is an FFPE sample or solubilized FFPE sample. In a preferred embodiment, the sample is a blood, plasma or lymph sample. In a preferred embodiment, the blood or plasma sample contains circulating tumor cells. In a preferred embodiment, the sample comprises cell lines. In a preferred embodiment, the measurement may be quantitative across a wide dynamic range. In a preferred embodiment, the wide dynamic range is about 2 logs. In a more preferred embodiment, the wide dynamic range is about 1-1.5 logs in breast cancer samples. In a preferred embodiment, the method provides a quantitative continuum of Her-3 expression. In a preferred embodiment, the measurement or quantity is sensitive to at least about 1000 receptors per cell to about 200,000 receptors per cell as determined by accuracy studies utilizing well-characterized cell line models and cross-validating technologies such as ELISA and flow cytometry. In a preferred embodiment, the measurement or quantity is sensitive to at least about 5000 receptors per cell to about 200,000 receptors per cell. In a preferred embodiment, the measurement or quantity is sensitive to at least about 10,000 receptors per cell to about 200,000 receptors per cell. In a preferred embodiment, the measurement or quantity is sensitive to at least about 25,000 receptors per cell to about 200,000 receptors per cell. In a preferred embodiment, the measurement is specific as determined by using isotype control antibodies and comparison with conventional IHC methods.

In a second aspect, the invention is drawn to a method for determining whether a subject with a cancer is likely to respond to treatment with a targeted therapy, for predicting a time course of disease and/or for predicting the probability of a significant event in the time course of the subject's cancer, comprising measuring in a biological sample from the subject's cancer an amount of Her-3, wherein the method is dependent on the level of Her-3. In certain embodiments, if the level of Her-3 is high, the patient is less likely or unlikely to respond to the targeted therapy. In certain embodiments, if the level of Her-3 is low, the patient is more likely to respond to the targeted therapy. In certain embodiments, as described in more detail herein, the therapy is a Her acting agent. In further embodiments, the therapy is at least one of a Her-2 acting agent or a Her-3-targeted agent. In certain embodiments, the amount of Her-3 is above a first threshold, such that the sample is stratified as having a "high" amount of Her-3 (e.g., either total Her-3 and/or Her-3 homodimers and/or Her-3 heterodimers). In some embodiments the first threshold value for her-3 is a total Her-3 (H3T) of $\geq 0.158$ and a low Her-3 value is below this threshold. Or, other ranges may be used depending upon the patient cohort and/or the significant event being monitored. Thus, each of the threshold values and/or threshold ranges described herein may vary by about 0.5 log units or less on a log scale and/or 25% or less on a linear scale (i.e., be $\leq 25\%$ larger and/or $\leq 25\%$ smaller than the specific ranges disclosed herein), or by about 20% or less, or by about 15% or less, or by about 10% or less, or by about 5% or less.

In a preferred embodiment, the subject's cancer is breast cancer, colorectal cancer, ovarian cancer, bladder cancer, prostate cancer, non-small cell lung cancer, melanoma, pharyngeal cancer, pancreatic cancer, esophageal cancer, glioma, biliary tract carcinoma, cholangiocarcinoma, gastric cancer, endometrial cancer, gall bladder cancer, squamous cell carcinoma or basal cell carcinoma. In a preferred embodiment, the subject's cancer is breast cancer, melanoma, synovial carcinoma, colorectal cancer or ovarian cancer. In a preferred embodiment, the subject's cancer is a Her-2 positive breast cancer. In a certain embodiments, the breast cancer is early stage (i.e., adjuvant) breast cancer or metastatic breast cancer.

As noted above, in certain embodiments, the method comprises detection of other biomarkers in the sample. For example, other biomarkers such as Her-2 and/or p95 may be measured. Or, other biomarkers such as can be at least one of FOXM1, PRAME, Bcl2, STK15, CEGP1, Ki-67, GSTM1, CA9, PR, BBC3, NME1, SURV, GATA3, TFRC, YB-1, DPYD, GSTM3, RPS6 KB1, Src, Chk1, ID1, EstR1, p27, CCNB1, XIAP, Chk2, CDC25B, IGF1R, AK055699, P13KC2A, TGFB3, BAGI1, CYP3A4, EpCAM, VEGFC, pS2, hENT1, WISP1, HNF3A, NFKBp65, BRCA2, EGFR, TK1, VDR, Contig51037, pENT1, EPHX1, IF1A, CDH1, HIF1α, IGFBP3; CTSB, Her3 or DIABLO. In certain embodiments, the other biomarker can be VEGF, CD31, KDR, p95, or Her-2.

In certain embodiments, the level of Her-2 expression in the breast cancer is high. In certain embodiments, high Her-2 expression is a log $10H2T \geq$ about 1.14-1.25. In certain embodiments, the high Her-2 expression comprises expression that is very high and/or moderately high. In certain embodiments, the very high Her-2 expression is a log $10H2T \geq$ about 1.84-2.21. In certain embodiments of each of the methods disclosed herein, the moderately high expression is between 1.14-1.25 and 1.84-2.21 (i.e., $\geq 1.14$-1.25 and $\leq 1.84$-2.21). Or, other ranges may be used depending upon the patient cohort and/or the significant event being monitored. Thus, each of the threshold values and/or threshold ranges described herein may vary by about 0.5 log units or less on a log scale and/or 25% or less on a linear scale (i.e., be $\leq 25\%$ larger and/or $\leq 25\%$ smaller than the specific ranges disclosed herein), or by about 20% or less, or by about 15% or less, or by about 10% or less, or by about 5% or less.

Also, in certain embodiments, the level of p95 may be evaluated as either high or low. In some embodiments the first threshold value for p95 is a total p95 value of > or $\geq 90$ (on a linear scale) and a low p95 value is below this threshold. Or, other ranges may be used depending upon the patient cohort and/or the significant event being monitored. Thus, each of the threshold values and/or threshold ranges described herein may vary by about 25% or less (i.e., be $\leq 25\%$ larger and/or $\leq 25\%$ smaller than the specific ranges disclosed herein), or by about 20% or less, or by about 15% or less, or by about 10% or less, or by about 5% or less.

In certain embodiments, if the level of Her-3 is high, the patient is less likely or unlikely to respond to the targeted therapy. In certain embodiments, if the level of Her-3 is low, the patient is more likely to respond to the targeted therapy. In certain embodiments, the therapy is a Her-acting agent. In certain embodiments, the therapy is at least one of a Her-2 acting agent or a Her-3-targeted agent.

Thus, in certain embodiments, the method comprises measuring in a biological sample from the subject's cancer an amount of Her-2 and/or Her-2 homodimers, wherein if the amount of Her-2 and/or Her-2 homodimers is moderately high and Her-3 expression is low, then the patient is likely to respond to the Her-2 acting agent and/or the patient has a long time course. In certain embodiments, the method comprises measuring in a biological sample from the subject's cancer an amount of Her-2 and/or Her-2 homodimers, wherein if the amount of Her-2 and/or Her-2 homodimers is moderately high and Her-3 expression is high, then the patient is unlikely to respond to the Her-2 acting agent and/or the patient has a short time course.

Additionally and/or alternatively, in certain embodiments, the method comprises measuring in a biological sample from the subject's cancer an amount p95, wherein if the amount of p95 and Her-3 expression is low, then the patient is likely to respond to the therapeutically acting agent and/or the patient has a long time course. In an embodiment, the patient also has a high (or moderately high) level of Her-2. In certain embodiments, the method comprises measuring in a biological sample from the subject's cancer an amount of Her-2 and/or Her-2 homodimers, wherein if the amount of Her-2 and/or Her-2 homodimers is high and/or moderately high and Her-3 expression and/or p95 expression is high, then the patient is unlikely to respond to the Her-2 acting agent and/or the patient has a short time course.

In a preferred embodiment, the targeted therapy is at least one Her family-targeted agent. In a preferred embodiment, the Her family-targeted agent is a multi- or single-targeted agent. In a preferred embodiment, the multi-targeted agent is a dual kinase inhibitor or a bispecific antibody. In a preferred embodiment, the Her family-targeted agent is trastuzumab, lapatinib or pertuzumab. In a preferred embodiment, the at least one Her family-targeted agent is at least two agents, wherein the at least two agents are one or more Her-2-targeted monoclonal antibodies and/or EGFR-targeted monoclonal antibodies and/or an EGFR and Her-2 dual kinase inhibitor. In a preferred embodiment, the monoclonal antibody is trastuzumab. In a preferred embodiment the EGFR-targeted monoclonal antibody is cetuximab or panitumumab. In a preferred embodiment, the dual kinase inhibitor is lapatinib, erlotinib or gefitinib. In a preferred embodiment, the targeted therapy is a Her-3 or Her-3 signaling pathway acting agent. In a preferred embodiment, the Her-3 or Her-3 signaling pathway targeted agent is a Her-3 monoclonal antibody, a Her-3 dimerization inhibitor, a Her-3 phosphorylation inhibitor and/or an inhibitor of a Her-3 signaling pathway member selected from the group consisting of PI3K, Akt, mTOR and ERK½. In a preferred embodiment, likeliness to respond, likeliness to have a long time course and/or likeliness to have a significant event is measured as an overall survival rate, as time to progression, as disease-free survival, as progression-free survival, and/or as objective tumor response using the RECIST criteria.

In a preferred embodiment, whether the cancer is Her-2 positive is determined by IHC, FISH, CISH, quantitative mRNA, a hybridization array, or VERATAG®. In a preferred embodiment, determining the level of Her-3 is performed using IHC, FISH, CISH, quantitative mRNA, hybridization array, or VERATAG®.

In a preferred embodiment, the method further comprises determining that a subject is afflicted with a Her-2 positive cancer that is unlikely to respond to treatment according to a method of the invention, then advising a medical professional of the treatment option of administering to the subject an effective amount of a different therapeutic agent.

In a third aspect, the invention is drawn to a purified antibody that binds to Her-3. In a preferred embodiment, the antibody is a polyclonal antibody or a monoclonal antibody. In a preferred embodiment, the antibody is a monoclonal antibody. In a preferred embodiment, the antibody is raised against one of the peptides having SEQ ID NOs:1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs: 19, 20 and 21, respectively, and (b) a heavy chain variable region comprising CDR1, CDR2 and CDR3 having sequences as set forth in SEQ ID NOs:22, 23 and 24, respectively. In a preferred embodiment, the antibody is the antibody with the amino acid sequence having SEQ ID NOs:9 and 11 as set forth in Table 1 (see Detailed Description) for the light and heavy chains, respectively, and/or SEQ ID NOs:10 and 12 as set forth in Table 1 (see Detailed Description) for the light and heavy chains, respectively.

BRIEF DESCRIPTION OF THE DRAWINGS

FIG. 2A lists peptide sequences used to immunize mice to raise Her-3-specific antibodies, wherein SEQ ID NO: 1 is LGSALSLPVLNRPRGTGQSLLSP; SEQ ID NO: 2 is SAYHSQRHSLLTPVTPLSP; SEQ ID NO: 3 is VGSDL-SASLGSTQSCPLHPVPI; SEQ ID NO; 4 is CQG-PGHQAPHVHYARLKTLRS; SEQ ID NO; 5 is LEEVELE-PELDLDLDLEAE; SEQ ID NO; 6 is CFDNPDYWHSRLFPKANA; SEQ ID NO: 7 is CPDYWH-SRLFPKANAQRT; and SEQ ID NO; 8 is CFPKANAQRT. The peptide sequences represent different epitopes from the C-terminal region of Her-3 (the length of each peptide and the position relative to the N-terminus of the protein are shown). Antibodies raised against each peptide are listed in the fourth column. Each antibody has been confirmed to test positive in ELISA, IHC, and VERATAG® assays.

DETAILED DESCRIPTION OF THE INVENTION

Figure 1:
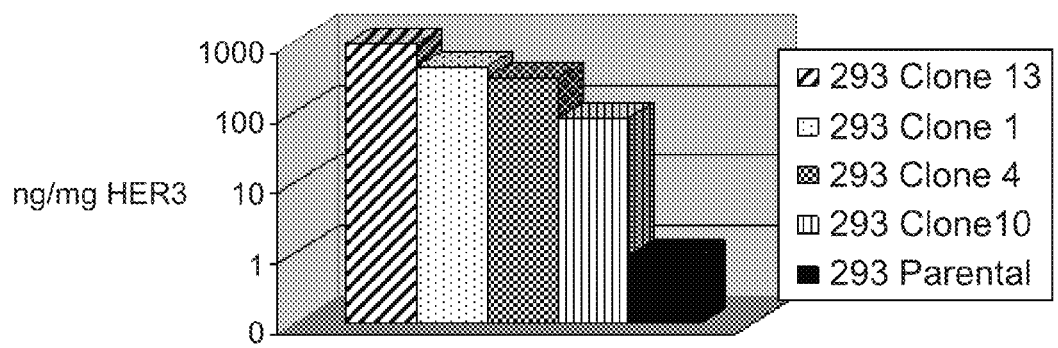
FIG. 1 shows the levels of Her-3 expression as determined by a Her-3 ELISA kit (R&D Systems, Inc.) in several stably-transfected clones of HEK 293 (human embryonic kidney cells) transfected with an HER3 expression vector. The construction of the expression vector is described in Example 1. One clone, 293H3-Clone 1, expressed high levels of HER3 and was selected as a control for use in the optimized HER3 VERATAG® assay.

As used herein, the terms "embodiment" and "aspect" are used interchangeably.

"Antibody" means an immunoglobulin that binds to, and is thereby defined as complementary with, a particular spatial and polar organization of another molecule. The antibody can be monoclonal, polyclonal or recombinant and can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for binding. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab' and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity for a particular binding site is maintained. Guidance in the production and selection of antibodies and antibody derivatives for use in immunoassays, including such assays employing releasable molecular tags (as described below) can be found in readily available texts and manuals, e.g., Harlow and Lane, 1988, *Antibodies: A Laboratory Manual*, Cold Spring Harbor Laboratory Press, New York; Howard and Bethell, 2001, *Basic Methods in Antibody Production and Characterization*, CRC Press; Wild, ed., 1994, *The Immunoassay Handbook*, Stockton Press, New York.

"Binding compound" shall refer to a molecule capable of binding to another molecule of interest. A binding compound may be an antibody, a peptide, a peptide or non-peptide ligand for a cell surface receptor, a protein, an oligonucleotide, an oligonucleotide analog, such as a peptide nucleic acid, a lectin or any other molecular entity that is capable of specifically binding to a target molecule or complex. In one embodiment, the target molecule is a protein or protein complex. In another embodiment, a binding compound further comprises a proximity probe. In one embodiment, a binding compound comprises one or more molecular tags attached to a binding moiety. In another embodiment, a second binding compound may be bound to the binding compound and measured or quantified as a correlative for the presence of the binding compound, which is bound to the target protein. As another specific example, either the first or second binding compound may generate an effector molecule that acts in conjunction with a proximity probe with an effective proximity, producing a signal that correlates with the presence of the target protein. Further, in another embodiment, binding compounds may have molecular tags that interact with one another within an effective proximity to form a complex that generates a signal or can be detected and measured in a manner that correlates with the presence of the target protein. More specifically, the target protein or complex may be Her-3 or Her-3 in a complex.

"Binding moiety" means any molecule to which molecular tags can be directly or indirectly attached that is capable of binding to an analyte. Binding moieties include, but are not limited to, antibodies, peptides, proteins, nucleic acids and organic molecules having a molecular weight of up to about 1000 daltons and containing atoms selected from the group consisting of hydrogen, carbon, oxygen, nitrogen, sulfur and phosphorus. Preferably, binding moieties are antibodies.

"Cell lines" refers to cells that have been separated from their original tissue, clonally multiplied and/or maintained in culture. As specific examples, cell lines may be derived from each type of cancer and multiple different cell lines may be derived from samples of the same type of cancer. Examples of different types of cell lines include, but are not limited to, breast cancer cell lines, such as MCF-7, MDA-MB-453, MDA-MB-468, or T-47D or cell lines derived from other tissues, such as SKOV3 or HEK293.

"Chemotherapeutic agent" means a chemical substance that is used to treat a condition, particularly cancer.

A "cleavable linkage," as used herein, refers to a chemical linking group that may be cleaved to release a detectable molecular tag connected to a binding moiety with the cleavable linkage.

A "cleavage-inducing moiety," or "cleaving agent," as used herein, is a group that produces an active species that is capable of cleaving a cleavable linkage. Preferably, the active species is a chemical species that exhibits short-lived activity so that its cleavage-inducing effects are only in the proximity of the site of its generation.

A "cleaving probe," as used herein, refers to a reagent that comprises a cleavage-inducing moiety, as defined herein, and a binding compound such as an antibody, a peptide, a peptide or non-peptide ligand for a cell surface receptor, a protein, such as streptavidin, a small molecule, such as biotin, an oligonucleotide, an oligonucleotide analog, such as a peptide nucleic acid, a lectin or any other molecular entity that is capable of binding to a target protein or molecule or stable molecular complex.

"Dual kinase inhibitor" refers to molecules that inhibit more than one kinase, for example but not limited to, an inhibitor of both EGFR and Her-2 kinase activity, such as lapatinib.

"Effective proximity," as used herein, describes the distance between two binding compounds that is sufficient to generate a detectable signal, indicating the presence of the target molecule. For example, a proximity probe and a binding compound that are bound on Her-3 (or with another analyte of interest) within an effective proximity will generate a detectable signal, indicating and/or quantifying the presence of Her-3 and/or a Her-3 complex. Preferably, the effective proximity range for many detection systems is less than 200 nM, more preferably, less than 50 nM.

"EGFR", "ErbB1", "erbB-1", "HER1", "her-1", "Her-1" and refers to the epidermal growth factor receptor and allelic variants thereof, as described, for example, by Ono and Kuwano (see Ono and Kuwano (2006) *Cuin. Cancer Res.* 12:7242-7251) and Genbank accession number P00533. Unless indicated otherwise, the terms "EGFR", "ErbB1", "erbB-1", "HER1", "her-1", "Her-1" when used herein refer to the human protein.

"Epitope" refers to a site on the surface of a molecule, usually a protein, to which an antibody molecule or other binding compound binds. Generally, a protein has several or many different epitopes, also called antigenic determinants, and reacts with antibodies of different specificities.

"FFPE" shall refer to a group of cells or quantity of tissue that are fixed, particularly conventional formalin-fixed paraffin-embedded samples. Such samples are typically, for example, without limitation, used in an assay for receptor complexes in the form of thin sections, e.g. 3-10 µm thick, of fixed tissue mounted on a microscope slide or equivalent surface. Such samples also typically undergo a conventional re-hydration procedure, and optionally, an antigen retrieval procedure as a part of, or preliminary to, assay measurements.

As used herein, "greater than or equal to" (i.e., $\geq$ or >=) can in certain alternative embodiments mean "greater than" (>). Also, as used herein, "less than or equal to" (i.e., $\leq$ or <=) can in certain alternative embodiments mean "less than" (<).

"Her-2", "ErbB2", "c-Erb-B2", "HER2", "Her2" and "neu" are used interchangeably herein and refer to native Her-2, and allelic variants thereof, as described, for example, in Semba et al., 1985, *P.N.A.S. USA* 82:6497-650 and Yamamoto et al., 1986, *Nature* 319:230-234 and Genebank accession number X03363. Unless indicated otherwise, the terms "Her-2", "ErbB2", "c-Erb-B2", "HER2" and "Her2" when used herein refer to the human protein. The gene encoding Her2 is referred to herein as "erbB2."

"Her-2-acting agent," as used herein, refers to a compound that can alter a biological activity of Her-2 or a Her-2 expressing cell or a Her-2 positive cancer cell. Such biological activities include, but are not limited to, dimerization, autophosphorylation, phosphorylation of another receptor, signal transduction and the like. Biological activities can include, without limitation, cell survival and cell proliferation and inhibition of such activities by a Her-2 acting agent could be direct or indirect cell killing (e.g., ADCC), disruption of protein complexes or complex formation, modulation of protein trafficking or enzyme inhibition. Biological activities can also include patient response as set forth in this application. Exemplary Her-2-acting agents include, but are not limited to, the large molecules 4D5, pertuzumab, and trastuzumab and small molecules such as AEE-788 and lapatinib. A Her-2 complex is used to describe complexes of proteins, such as heterodimers, in which Her-2 is a component. A Her-2 complex may include a Her-2 homodimer, or a heterodimer that includes Her-2 (e.g., a Her-2/Her-3 heterodimer)

"Her-3", "ErbB3", "c-erb-B3", "erbB-3", "HER3" and "Her3" are used interchangeably herein and refer to native Her-3, and allelic variants thereof, as described, for example, in Kraus M H, et al. (1989) *Proc Natl Acad Sci USA* 86:9193-9197 and Plowman G D, et al. (1990) *Proc Natl Acad Sci USA*. 87:4905-4909 and Genbank accession number P21860. Unless indicated otherwise, the terms "Her-3", "ErbB3", "c-erb-B3", "erbB-3", "HER3" and "Her3" when used herein refer to the human protein. The gene encoding Her3 is referred to herein as "erbB3."

"Her-3 complex" is used to describe complexes of proteins, such as heterodimers, in which Her-3 is a component. Examples of heterodimers including Her-3 include but are not limited to Her-1/Her-3 and Her-2/Her-3.

"Her-3-targeted agent" or "Her-3 signaling pathway targeted agent" refers to therapeutics that alter the biological activity of Her-3 or members of the Her family signaling pathway. Such biological activities include, but are not limited to, dimerization, autophosphorylation, phosphorylation of another receptor, signal transduction and the like. Biological activities can include, without limitation, cell survival and cell proliferation and inhibition of such activities by a Her-3 or Her-3 signaling pathway member acting agent could be direct or indirect cell killing (e.g., ADCC), disruption of protein complexes or complex formation, modulation of protein trafficking or enzyme inhibition. Biological activities can also include patient response as set forth in this application. Exemplary Her-3 or Her-3 signaling pathway member acting agents might include, but are not limited to, large molecules (such as antibodies) or small molecules (such as small molecule kinase inhibitors) targeted to Her-3, PI3K, Akt, mTOR, ERK½, or PYK2.

"High" refers to a measure that is greater than normal, greater than a standard such as a predetermined measure or a subgroup measure or that is relatively greater than another subgroup measure. For example, high Her-3 refers to a measure of Her-3 that is greater than a normal Her-3 measure. A normal Her-3 measure may be determined according to any method available to one skilled in the art. High Her-3 may also refer to a measure that is equal to or greater than a predetermined measure, such as a predetermined cutoff. High Her-3 may also refer to a measure of Her-3 wherein a high Her-3 subgroup has relatively greater levels of Her-3 than another subgroup. For example, without limitation, according to the present specification, two distinct patient subgroups can be created by dividing samples around a mathematically determined point, such as, without limitation, a median, thus creating a subgroup whose measure is high (i.e., higher than the median) and another subgroup whose measure is low. Her-3 can be measured by any method known to one skilled in the art such as, for example, without limitation, using VERATAG® or using any standard immunohistochemical (IHC) method. In some cases, a "high" expression level may comprise a range of expression that is very high and a range of expression that is "moderately high" where moderately high is a level of expression that is greater than normal, but less than "very high". Example ranges for high (including very high and moderately high) Her-2 expression and/or high Her-3 and/or high p95 expression are provided herein.

"IHC, FISH and CISH" are methods (immunohistochemistry, fluorescence in situ hybridization, and chromogenic in situ hybridization, respectively) used to detect the presence of molecular entities in cells or tissues. For example, membrane receptors such as Her-3 and/or other members of the EGFR family of receptors can be detected using these methods.

"Isotype control antibodies" refers to antibodies that have the same underlying immunoglobulin structure as a specific antibody used as a binding compound but that do not have specificity for the targeted epitope. The use of isotype control antibodies allows one to observe any binding that is due to non-specific binding.

"Likely to" (and "unlikely to"), as used herein, refers to an increased (or decreased) probability that an item, object, thing or person will occur. Thus, in one example, a subject that is likely to respond to treatment with trastuzumab has an increased probability of responding to treatment with trastuzumab relative to a reference subject or group of subjects.

"Long," as used herein, refers to a time measure that is greater than normal, greater than a standard such as a predetermined measure or a subgroup measure that is relatively longer than another subgroup measure. For example, with respect to a patient's longevity, a long time progression refers to time progression that is longer than a normal time progression. Whether a time progression is long or not may be determined according to any method available to one skilled in the art. In one embodiment, "long" refers to a time that is greater than the median time course required for a significant event to occur in a disease.

"Low" is a term that refers to a measure that is less than normal, less than a standard such as a predetermined measure or a subgroup measure that is relatively less than another subgroup measure. For example, low Her-3 means a measure of Her-3 that is less than a normal Her-3 measure in a particular set of samples of patients. A normal Her-3 measure may be determined according to any method available to one skilled in the art. Low Her-3 may also mean a measure that is less than a predetermined measure, such as a predetermined cutoff. Low Her-3 may also mean a measure wherein a low Her-3 subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high (i.e., greater than the median). Her-3 can be measured by any method known to one skilled in the art such as, for example, without limitation, using the VERATAG® method or using any standard immunohistochemical (IHC) method. Example ranges for low values of Her-3, Her-2, and p95 expression are provided herein.

"Lysate" refers to the solution produced when the cell membranes of cells are disrupted, whether by physical or chemical methods. For example, "tumor lysates" typically contain representative components of the cells comprising the tumor, including but not limited to, protein markers, enzymes, nucleic acids and complexes of proteins and other molecules that can subsequently be measured in various assays.

A "molecular tag," as used herein, refers to a molecule that can be measured directly or indirectly, can be distinguished from other molecules based on one or more physical, chemical or optical differences among the molecules being separated, including but not limited to, electrophoretic mobility, molecular weight, shape, solubility, pKa, hydrophobicity, charge, charge/mass ratio, polarity or the like. In one embodiment, molecular tags in a plurality or set differ in electrophoretic mobility and optical detection characteristics and can be separated by electrophoresis. In another embodiment, molecular tags in a plurality or set may differ in molecular weight, shape, solubility, pKa, hydrophobicity, charge, polarity and can be separated by normal phase or reverse phase HPLC, ion exchange HPLC, capillary electrochromatography, mass spectroscopy, gas phase chromatography or a like technique.

Measurement of molecular tags may also involve using secondary molecular interactions, with or without further modification, to detect, enhance or amplify a measurable signal that acts as a correlative for the presence and/or quantity of an analyte, such as Her-3 or a Her-3 in a complex. In one embodiment, a set of two or more molecular tags may interact within an effective proximity to produce a measurable signal. As molecular tags, a measurable signal may be generated, for example, by detection of two complementary nucleic acid sequences that will hybridize when the complementary sequences are within an effective proximity. Other examples that either generate a measurable signal or that can be measured using detection methods know in the art include, but are not limited to, FRET, BRET, BiFC, LCI and QPCR.

"Overall survival" or "OS" refers to a time as measured from the start of treatment to death or censor. Censoring may come from a study end or change in treatment. Overall survival can refer to a probability as, for example, a probability when represented in a Kaplan-Meier plot of being alive at a particular time, that time being the time between the start of the treatment to death or censor.

"Pre-determined cutoff" as used herein, refers to the value of a predetermined measure on subjects exhibiting certain attributes that allow the best discrimination between two or more categories of an attribute. For example, a pre-determined cutoff that allows one to discriminate between two categories such as high Her-3 expression and low Her-3 expression for determining overall survival may be used. Pre-determined cutoffs may be used to separate the subjects with values lower than or higher than the pre-determined cutoff to optimize the prediction model.

A "proximity probe," as used herein, refers to a reagent that comprises a moiety capable of acting within effective proximity to a molecular tag on a binding compound to generate a detectable signal and an antibody, a peptide, a peptide or non-peptide ligand for a cell surface receptor, a protein, such as streptavidin, a small molecule, such as biotin, an oligonucleotide, an oligonucleotide analog, such as a peptide nucleic acid, a lectin or any other molecular entity that is capable of specifically binding to a target protein or molecule or stable complex. For example, a proximity probe comprised of a Her-3-targeted antibody with a molecular tag may be capable of binding to Her-3 within an effective proximity to one or more Her-3 binding compounds, or a binding compound of another protein of interest, that has one or more molecular tags attached. In one embodiment, a proximity probe comprises a binding molecule and a first nucleic acid and a binding molecule comprises an antibody and a second nucleic acid, wherein the first and second nucleic acids are complementary to each other and each is a predetermined length so that when the nucleic acids are within an effective proximity of one another, they hybridize. Hybridization may be measured by any method known to one skilled in the art. For example, fluorophores may be attached to the nucleic acids as indicators of hybridization. In a preferred embodiment, hybridization is measured with a nucleic acid amplification method such as, for example, without limitation, the rolling circle amplification method (see, for example, Lizardi et al., (1998) *Nat Genet.* 19: 225-232).

"RECIST" shall mean "Response Evaluation Criteria in Solid Tumours" and is a set of published rules that define when cancer patients improve ("respond"), stay the same ("stable") or worsen ("progression") during treatments. Response as defined by RECIST criteria have been published, for example, at *Journal of the National Cancer Institute*, Vol. 92, No. 3, Feb. 2, 2000 and RECIST criteria may include other similar published definitions and rule sets.

"Respond" to treatment, and other forms of this verb, as used herein, refer to the reaction of a subject to treatment with an agent. As an example, a subject responds to treatment if growth of a tumor in the subject is retarded about 10%, 20%, 30%, 40%, 50%, 60%, 70%, 80%, 90% or more. In another example, a subject responds to treatment if a tumor in the subject shrinks by about 5%, 10%, 20%, 30%, 40%, 50% or more as determined by any appropriate measure, e.g., by mass or volume. In another example, a subject responds to treatment with a Her2-acting agent if the subject experiences a life expectancy extended by about 5%, 10%, 20%, 30%, 40%, 50% or more beyond the life expectancy predicted if no treatment is administered. In another example, a subject responds to treatment with an agent if the subject has an overall survival or increased time to progression. Several methods may be used to determine if a patient responds to a treatment including the RECIST criteria, as set forth herein.

"Sample" or "tissue sample" or "patient sample" or "patient cell or tissue sample" or "specimen" each refer to a collection of similar cells obtained from a tissue of a subject or patient. The source of the tissue sample may be solid tissue as from a fresh tissue, frozen and/or preserved organ or tissue or biopsy or aspirate; blood or any blood constituents, bodily fluids such as cerebral spinal fluid, amniotic fluid, peritoneal fluid or interstitial fluid or cells from any time in gestation or development of the subject. The tissue sample may contain compounds that are not naturally intermixed with the tissue in nature such as preservatives, anticoagulants, buffers, fixatives, nutrients, antibiotics or the like. Cells may be fixed in a conventional manner, such as in an FFPE manner.

"Short," as used herein, refers to a time measure that is shorter than normal, shorter than a standard such as a predetermined measure or a subgroup measure that is relatively shorter than another subgroup measure. For example, with respect to a patient's longevity, a short time progression refers to time progression that is shorter than a normal time progression or shorter than predicted. Whether a time progression is short or not may be determined according to any method available to one skilled in the art. In one embodiment, "short" refers to a time that is less than the median time course required for a significant event to occur in a disease.

"Signaling pathway", as used herein, refers to a process in which the binding of extracellular signaling molecules to cell-surface receptors trigger events inside the cell and/or a process in which intracellular signaling cascades can be triggered through intracellular interactions. For example, receptor tyrosine kinases are transmembrane proteins that propagate growth factor signals from the cell surface to intracellular processes that control critical functions such as growth, differentiation, angiogenesis and inhibition of apoptosis. In cancer, these signaling pathways are often exploited to facilitate tumor growth and metastasis. One such family of receptor tyrosine kinases is the epidermal growth factor receptor (EGFR) family. EGFR family members, EGFR, HER2, HER3 and HER4, are over-expressed in a wide variety of tumor types.

"Significant event," as used herein, shall refer to an event in a patient's disease that is important as determined by one skilled in the art. Examples of significant events include, for example, without limitation, primary diagnosis, death, recurrence, the determination that a patient's disease is metastatic, relapse of a patient's disease or the progression of a patient's disease from any one of the above noted stages to another. A significant event may be any important event used to assess OS, TTP and/or using the RECIST or other response criteria, as determined by one skilled in the art.

As used herein, the terms "subject" and "patient" are used interchangeably. As used herein, the terms "subject" and "subjects" refer to an animal, preferably a mammal including a non-primate (e.g., a cow, pig, horse, donkey, goat, camel, cat, dog, guinea pig, rat, mouse or sheep) and a primate (e.g., a monkey, such as a cynomolgus monkey, gorilla, chimpanzee or a human).

"Targeted therapy" refers to therapeutic treatment that attempts to identify and treat specific cells involved in disease without harming or altering normal cells. Targeted therapeutics may be comprised of, but not limited to, small molecules, such as lapatinib and iressa/gleevec, monoclonal antibodies, such as trastuzumab or nucleic acids, such as siRNAs used to block expression of gene products involved in disease processes. Targeted therapies are useful in the treatment of many disease processes, such as cancer.

As used herein, "time course" shall refer to the amount of time between an initial event and a subsequent event. For example, with respect to a patient's cancer, time course may relate to a patient's disease and may be measured by gauging significant events in the course of the disease, wherein the first event may be diagnosis and the subsequent event may be metastasis, for example.

"Time to progression" or "TTP" refers to a time as measured from the start of the treatment to progression or a cancer or censor. Censoring may come from a study end or from a change in treatment. Time to progression can also be represented as a probability as, for example, in a Kaplan-Meier plot where time to progression may represent the probability of being progression free over a particular time, that time being the time between the start of the treatment to progression or censor.

"Treatment," and other forms of this word refer to the administration of an agent to impede a disease, such as the growth of a cancer, to cause a cancer to shrink by weight or volume, to extend the expected survival time of the subject and/or time to progression of the tumor or the like. Treatment may also refer to any course which one skilled, for example, a treating physician, deems expedient.

The term "VERATAG®" refers to single and multiplexed and multi-label assays, materials, methods and techniques for performing and utilizing such assays, including but not limited to reagents, analytical procedures and software related to those assays. The terms VERATAG®, vTag and ETAG® shall be used interchangeably.

In a first aspect, the invention is drawn to a method of measuring and/or quantifying the presence and/or amount of Her-3 and/or Her-3 in a complex in a sample, the method comprising providing a sample and determining the presence and/or quantity of Her-3 and/or Her-3 in a complex in the sample. In a preferred embodiment, the sample is a biological sample. In a preferred embodiment, the sample is a tissue sample. In a preferred embodiment, the sample is a fresh tissue sample, a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate from a fresh or frozen tumor sample. In a preferred embodiment, the sample is an FFPE sample or solubilized FFPE sample. In a preferred embodiment, the sample comprises a breast cancer sample. In a certain embodiments, the breast cancer is early stage (i.e., adjuvant) breast cancer or metastatic breast cancer. In certain embodiments, the level of Her-2 expression in the breast cancer is high. In certain embodiments, high Her-2 expression is a log 10H2T≧about 1.14-1.25. In certain embodiments, the high Her-2 expression comprises expression that is very high and/or moderately high. In certain embodiments, the very high Her-2 expression is a log 10H2T≧ about 1.84-2.21. Or, other ranges may be used depending upon the patient cohort. In certain embodiments, if the level of Her-3 is high, the patient is less likely or unlikely to respond to the targeted therapy. In certain embodiments, if the level of Her-3 is low, the patient is more likely to respond to the targeted therapy. In certain embodiments, as described in more detail herein, the therapy is a Her acting agent. In further embodiments, the therapy is at least one of a Her-2 acting agent or a Her-3-targeted agent.

In a preferred embodiment, the sample is a blood, plasma or lymph sample. In a preferred embodiment, the blood or plasma sample contains circulating tumor cells. In a preferred embodiment, the sample comprises cell lines. In a preferred embodiment, the measurement may be quantitative across a wide dynamic range.

In a preferred embodiment, the method comprises mixing the sample with a binding compound and determining the presence and/or quantity of the binding compound bound to Her-3 and/or Her-3 in a complex. In a preferred embodiment, the binding compound binds specifically to Her-3. In a preferred embodiment, the binding compound comprises an antibody. In a preferred embodiment, the antibody is raised against one of the peptides having SEQ ID NOs:1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively, as shown in Table 1B. In a preferred embodiment, the antibody is the antibody with the amino acid sequence having SEQ ID NOs:9 and 11 as set forth in Table 1A for the light and heavy chains, respectively, and/or SEQ ID NOs:10 and 12 as set forth in Table 1B for the light and heavy chains, respectively.

TABLE 1A

Her3 light chain sequences:
>Her3.B9A11.H1_LC (clone 6-6)

SEQ ID NO: 9
MDSQAQVLILLLLWVSGTCGDIVMSQSPSSLAVSAGEKVTLSC<u>KSSQSLLNSRTRKNYLA</u>WYQQKPGQSPKL
LIY<u>WASTRES</u>GVPD RFTGSGSGTDFTLTVSSVQAEDLAVYYC<u>KQSYNLWT</u>FGGGTKLEIK

TABLE 1A-continued

>Her3.F9B10.3_LC (clone 7-3)

SEQ ID NO: 10
MRCLAEFLGLLVLWIPGAIGDIVMTQGAPSVPVTPGESVSISCRSSKSLLQNNGNTYLYWFLQRPGQSPQLL
IYRMSNLASGVPDRFSGSGSGTAFTLRISRVEAEDVGVYYCMQHLEYPLTFGAGTKLGLK

Her3 heavy chain sequences:
>Her3.B9A11.H1_HC (clone 1-14)

SEQ ID NO: 11
MECNWILPFILSVTSGVYSEVQLQQPGTVLARPGASVRMSCKASGYTFTSYWMHWVKQRPGQGLEWIGAIYP
GNSDTRDNQKFKGKAELTAVTSASTAYMELSSLTNEDSAVYYCTSYYFDGAGYFDFWGQGTTLTVSS

>Her3.F9B10.3_HC (clone 2-1)

SEQ ID NO: 12
MEWSWVFLFLLSVIASVQSQVQLQQSGAEVVRPGASVTLSCKASAYTFTDYELHWMRQTPVHGLEWIGAS
DPETGGSAYNQKFKGKAILTADKSSSTAFMELRSLTSEDSAVYFCTRRIFYFGSRGDFFDYWGQGTSLTVSS

TABLE 1B

Complementarity-Determining Regions (CDRs)

|  | Her3.B9A11.H1_LC | Her3.B9A11.H1_HC | Her3.F9B10.3_LC | Her3.F9B10.3_HC |
|---|---|---|---|---|
| CDR1 | KSSQSLLNSRTRKNYLA<br>SEQ ID NO: 13 | SYWMH<br>SEQ ID NO: 16 | RSSKSLLQNNGNTYLY<br>SEQ ID NO: 19 | DYELH<br>SEQ ID NO: 22 |
| CDR2 | WASTRES<br>SEQ ID NO: 14 | AIYPGNSDTRDNQKFKG<br>SEQ ID NO: 17 | RMSNLAS<br>SEQ ID NO: 20 | ASDPETGGSAYNQKFKG<br>SEQ ID NO: 23 |
| CDR3 | KQSYNLWT<br>SEQ ID NO: 15 | YYFDGAGYFDF<br>SEQ ID NO: 18 | MQHLEYPLT<br>SEQ ID NO: 21 | RIFYFGSRGDFFDY<br>SEQ ID NO: 24 |

TABLE 1A and 1B. The amino acid sequences of the light and heavy chains of two antibodies that bind Her3, Her3.B9A11.H1 and Her3.F9B10.3, are shown in Table 1A. The clonal isolates from which the sequences were derived are shown and the complementarity-determining regions (CDRs) are underlined. The light and heavy chains are denoted by "_LC" or "_HC", respectively. Table 1B shows the three CDRs for the B9A11.H1 light and heavy chains and the F9B10.3 light and heavy chains, respectively.

In a preferred embodiment, the method comprises mixing (i) a sample that may contain Her-3 and/or Her-3 in a complex; (ii) a proximity probe that is capable of binding Her-3 and/or at least one other analyte, the proximity probe having an effective proximity and (iii) at least one binding compound, the at least one binding compound being capable of binding Her-3 and having one or more signaling molecules attached, wherein binding of the proximity probe and the binding compound within the effective proximity produces a signal from the molecular tags that correlates with the presence and/or quantity of Her-3 and/or Her-3 in a complex. In a preferred embodiment, the proximity probe and/or binding compound is capable of binding specifically to Her-3. In a preferred embodiment, the proximity probe and/or binding compound further comprises an antibody and each antibody may bind to a specific epitope on Her-3. In a preferred embodiment, the antibody is raised against one of the peptides having SEQ ID NOs: 1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively (Table 1B). In a preferred embodiment, the antibody is the antibody with the amino acid sequence having SEQ ID NOs:9 and 11 as set forth in Table 1A for the light and heavy chains, respectively, and/or SEQ ID NOs:10 and 12 as set forth in Table 1A for the light and heavy chains, respectively. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample as discussed herein. For example, in a certain embodiments, the breast cancer is early stage (i.e., adjuvant) breast cancer or metastatic breast cancer. In certain embodiments, the level of Her-2 expression in the breast cancer is high. In certain embodiments, high Her-2 expression is a log 10H2T≧about 1.14-1.25. In certain embodiments, the high Her-2 expression comprises expression that is very high and/or moderately high. In certain embodiments, the very high Her-2 expression is a log 10H2T≧about 1.84-2.21. Or, other ranges may be used depending upon the patient cohort.

In a preferred embodiment, the sample is an FFPE sample or solubilized FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range. In a preferred embodiment, the wide dynamic range is approximately 2 logs. In a more preferred embodiment, the wide dynamic range is about 1-1.5 logs in breast cancer samples. In a preferred embodiment, the method provides a quantitative continuum of Her-3 expression. In a preferred embodiment, the measurement or quantity is sensitive to at least about 1000 receptors per cell to about 200,000 receptors per cell as determined by accuracy studies utilizing well-characterized cell line models and cross-validating technologies such as ELISA and flow cytometry. In a preferred embodiment, the measurement or quantity is sensitive to at least about 5000 receptors per cell to about 200,000 receptors per cell. In a preferred embodiment, the measurement or quantity is sensitive to at least about 10,000 receptors per cell to about 200,000 receptors per cell. In a preferred embodiment, the measurement or quantity is sensitive to at least about 25,000 receptors per cell to about 200,000 receptors per cell. In a preferred embodiment, the measurement is specific as determined using isotype control antibodies and comparison with conventional IHC methods.

In a preferred embodiment, determining the presence and/or quantity of binding compound bound to Her-3 further comprises providing a second binding compound, the second binding compound being able to specifically bind the binding compound bound to Her-3 and determining the presence and/or quantity of the second binding compound as correlative of the presence and/or quantity of the binding compound bound to Her-3. In a preferred embodiment, the second binding compound is an antibody.

The use of a second binding compound that is capable of specifically binding the first binding compound and has one or more molecular tags may have practical advantages. For example, multiple Her-3-specific first binding compounds may be tested using a single second binding compound to which is attached one or more molecular tags, abrogating the need for attaching molecular tags to each of the multiple Her-3-specific first binding compounds. In a preferred embodiment, the first binding compound is a mouse antibody and the second binding compound is an anti-mouse antibody raised in a non-mouse species (e.g., goat anti-mouse antibodies) to which cleavable molecular tags have been attached.

Second binding compounds are typically labeled with probes useful for detection. Detection systems commonly used for detecting second binding compounds include but are not limited to cleavable molecular tags, as described herein; radiolabels (i.e., radioisotopes such as I-125); enzymes that convert a chemical into a measurable colorimetric, fluorescent or electrochemical signal (e.g., peroxidases) and fluorescent proteins (e.g., green fluorescent protein and its many derivatives).

The antibody can be monoclonal, polyclonal or recombinant and can be prepared by techniques that are well known in the art. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab' and the like. Antibodies may also be single-chain antibodies, chimeric antibodies, humanized antibodies or any other antibody derivative known to one of skill in the art that retains binding activity that is specific for a particular binding site. In addition, aggregates, polymers and conjugates of immunoglobulins or their fragments can be used where appropriate so long as binding affinity is maintained.

To facilitate the development of methods to measure Her-3 in biological samples, Her-3-specific monoclonal antibodies were created. Mice were immunized against peptides from Her-3 (shown in FIG. 2A) and standard methods as set forth further herein and as known to one skilled in the art were used to create hybridomas. Many methods are known for the creation and production of monoclonal antibodies, for example, the hybridoma method as first described by Koehler et al. (1975) *Nature* 256:495-497 or other methods described in the literature (see Goding, J W (1980) *J. Immunol. Methods* 34:285-308; Harlow E and Lane D (1988) in *Antibodies: A Laboratory Manual*, Chapter 6; Kennett R H et al. (1980) *Monoclonal Antibodies*, Plenum Press; Zola H (1987) *Monoclonal Antibodies: A Manual of Techniques*, CRC Press).

In one embodiment, the method of creating hybridomas begins with immunizing a host animal, such as a mouse, to elicit the production of lymphocytes that produce antibodies targeted to the peptide or protein(s) of interest. Lymphocytes may also be immunized in vitro. The antigen used may be a peptide, a protein or a cell displaying the antigen on the cell surface. Lymphocytes are collected then fused by chemical (e.g., with PEG) or electrical (e.g., by electrofusion) methods with myeloma cells to form hybridoma cells, typically under conditions that prevent the growth and/or survival of the parent myeloma cells. Fused cells are allowed to grow because they contain enzymes that facilitate survival in the culture medium. In a preferred embodiment, the culture medium contains hypoxanthine, aminopterin and thymidine (HAT medium), which prevents the growth of cells lacking hypoxanthine quinine phosphoribosyl transferase (HPRT). The HPRT is supplied to the fused cell by the lymphocyte partner, allowing survival of the hybridoma but preventing survival of the parent myeloma cells, which lack HPRT.

Figure 2B:
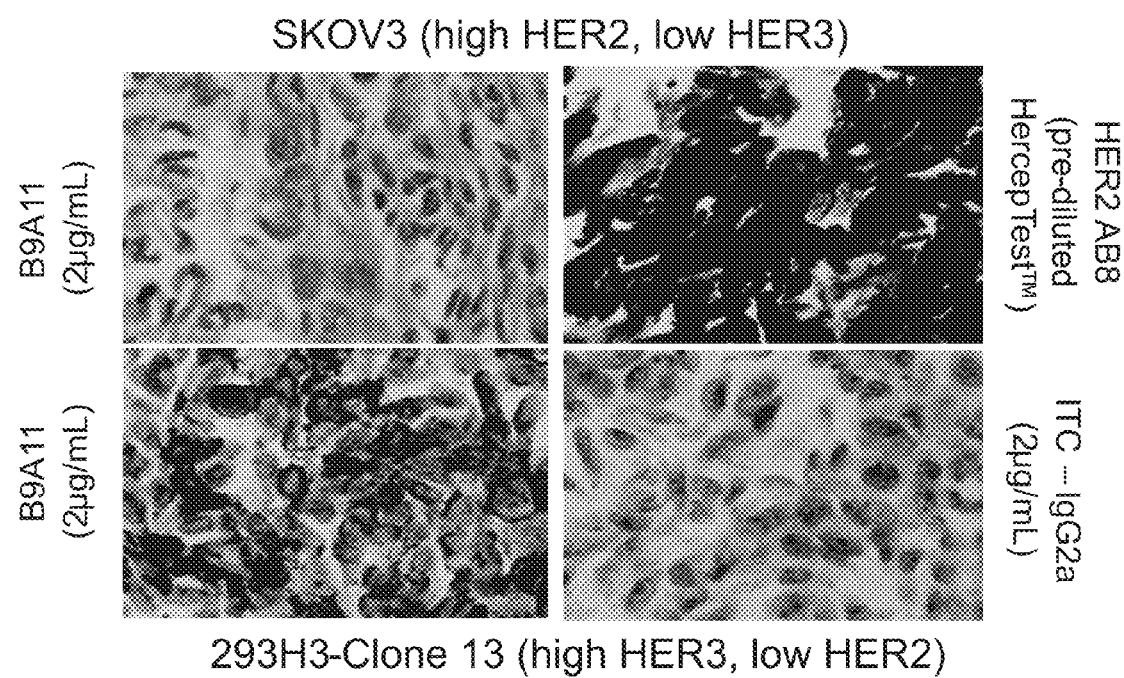
FIG. 2B shows the results of IHC studies in which two cell lines were screened with B9A11, an Her-3-specific antibody raised against one of the Her-3 peptides, an Her-2-specific antibody Ab8 (Hercept-Test™), and a control antibody ITC-IgG2a. One cell line, SKOV3 (upper panels), is known to express high levels of HER2 and low levels of HER3. The other cell line, 293H3-clone1 (lower panels), is the stably-transfected cell line described in Example 1 and shown in FIG. 1 to over-express HER3 but which expresses low levels of HER2. The IHC results show a strong signal of B9A11 with the 293H3-clone 1 cells but not the SKOV3 cells, as expected.
Figure 3:
FIG. 3 shows HER3 levels as determined by VERATAG® in FFPE blocks from 4 different cell lines, cross-validated with data from three other assays (IHC, ELISA, and flow cytometry). Cell lines expressing varying levels of HER3 were chosen for these studies: 293H3-Clone 1, MDA-MB-453, MDAMB-468 and SKOV3 (the latter 3 from ATCC). The cell lines were chosen to represent HER3 receptor levels that spanned greater than 2 logs. FFPE blocks were prepared as described in Example 3 for testing with the HER3 VER-ATAG® assay and IHC. A portion of the cells from the same lot were tested for HER3 receptor number using flow cytometry. Further, a whole cell lysate was prepared from the same lot of cells for quantifying HER3 with an ELISA kit (Human ErbB3-DuoSet ELISA: R&D Systems, Inc.). The data shows a wide dynamic range for the VERATAG® assay, with results consistent with all three other methodologies.

Culture media in which hybridomas are grown (i.e., conditioned media) are typically assayed for the production of monoclonal antibodies directed against the antigen using a variety of techniques (see Voller, et al. (1978) *J. Clin. Pathol.* 31:507-520), including but not limited to, immunoprecipitation or an in vitro binding assay such as enzyme-linked immunosorbant assay (ELISA; see Engvall E (1977) in *Biomedical Applications of Immobilized Enzymes and Proteins*, edited by TMS Chang, 2:87-96, Plenum Press), radioimmunoassay (RIA; see Sonksen P H (1974) *Brit. Med. Bull.* 30:1-103), Western blots or flow cytometry. Conditioned media from the hybridomas were profiled in a series of assays including ELISA (FIG. 1), Western blot (FIG. 2) and flow cytometry (FIG. 3). In preferred embodiments, studies using both native and permeabilized and fixed cells are performed to identify antibodies that may perform well in applications that use fixed cells or tissues, such as immunohistochemistry (IHC). Clones of interest may be subcloned by limiting dilution or single cell flow cytometry.

As will be known to those skilled in the art, monoclonal antibodies secreted by hybridoma clones (or subclones) can be purified using conventional purification procedures such as, but not limited to, dialysis, affinity chromatography, gel electrophoresis or protein A-sepharose (or protein L-agarose) chromatography.

One antibody generated, B9A11 (i.e., SEQ ID NOs: 9 and 11), which was raised against the peptide CFDNPDYWHSR-LFPKANA (SEQ ID NO: 6) from Her-3, was chosen for use in the Her3—VERATAG® assay experiments described herein. The hybridoma cell lines that produce antibodies B9A11 and F9B10 were deposited with the American Type Culture Collection, 10801 University Boulevard, Manassas, Va. 20110, on Jan. 12, 2010, under the terms of the Budapest Treaty and were accorded the ATCC accession numbers PTA-10574 and PTA-10575.

Many methods and reagents are commonly used to prepare biological samples for analysis. Several methods are outlined or referenced herein and many others are known to those skilled in the art. Samples containing Her-3 suitable for use as biomarkers may come from a wide variety of sources, including cell cultures, animal or plant tissues, patient biopsies, blood or the like. Preferably, samples are human patient samples. Samples are prepared for assays of the invention using conventional techniques, which may depend on the source from which a sample is taken. For biopsies and medical specimens, guidance is provided in the following references: Bancroft J D & Stevens A, eds. 1977, *Theory and Practice of Histological Techniques*, Churchill Livingstone, Edinburgh; Pearse, 1980, *Histochemistry. Theory and applied.* $4^{th}$ ed., Churchill Livingstone, Edinburgh.

Examples of patient tissue samples that may be used include, but are not limited to tissues of breast, prostate, ovary, colon, lung, endometrium, stomach, salivary gland or pancreas. The tissue sample can be obtained by a variety of procedures including surgical excision, aspiration or biopsy. The tissue may be fresh or frozen. In one embodiment, the biological sample may be cells cultured in vitro and collected by centrifugation as a cell pellet. In one embodiment, the samples may be patient blood samples or specific blood cell types or subsets of blood cell types (e.g., buffy coats). In one embodiment, the biological sample may be exosomes or samples containing exosomes. Exosomes are small (30-200 nm) vesicles that can be secreted by most cell types, including tumor cells (see Mignot et al (2006) *J. Cell. Mol. Med.* 10:376-3 88), in vivo and in vitro. Tumor-derived exosomes are thought to play a role in the ability of tumors to evade the immune system and have potential for both diagnostic and therapeutic applications (see Taylor and Black (1985) *J. Natl. Cancer Inst.* 74:859-867) and are therefore biological samples of interest.

In a preferred embodiment, the sample is a tumor sample. Examples of types of tumor samples include cancers such as, without limitation, carcinomas, sarcomas, myelomas, leukemias, lymphomas and mixed type cancers. In one embodiment, the cancer is a bone cancer, for example, Ewing's sarcoma, osteosarcoma and rhabdomyosarcoma and other soft-tissue sarcomas. In another embodiment, the cancer is a brain tumor, for example, oligodendroglioma, ependymoma, menengioma, lymphoma, schwannoma or medulloblastoma. In another embodiment, the cancer is breast cancer. In another embodiment, the cancer is an endocrine system cancer, for example, adrenal, pancreatic, parathyroid, pituitary and thyroid cancers. In another embodiment, the cancer is a gastrointestinal cancer, for example, anal, colorectal, esophageal, gall bladder, gastric, liver and small intestine cancers. In another embodiment, the cancer is a gynecological cancer, for example, cervical, endometrial, uterine, fallopian tube, gestational trophoblastic disease, choriocarcinoma, ovarian, vaginal or vulvar cancer. In another embodiment, the cancer is a head and neck cancer, for example, laryngeal, oropharyngeal, parathyroid or thyroid cancer. In another embodiment, the cancer is melanoma, squamous cell carcinoma or basal cell carcinoma. In another embodiment, the cancer is a leukemic cancer, for example, acute lymphocytic leukemia, acute myelogenous leukemia, chronic lymphocytic leukemia, chronic myelogenous leukemia, hairy cell leukemia or a myeloproliferative disorder. In another embodiment, the cancer is a lung cancer, for example, a mesothelioma or non-small cell lung cancer. In another embodiment, the cancer is a lymphoma, such as cutaneous T cell lymphoma, Hodgkin's disease or non-Hodgkin's disease. In another embodiment, the cancer is metastatic cancer. In another embodiment, the cancer is a myeloma, for example, a multiple myeloma. In another embodiment, the cancer is penile cancer. In another embodiment, the cancer is prostate cancer. In another embodiment, the cancer is testicular cancer. In another embodiment, the cancer is thyroid cancer, for example, papillary, follicular, medullary or anaplastic or undifferentiated thyroid carcinoma. In another embodiment, the cancer is a urinary tract cancer, for example, bladder, kidney or urethral cancer.

Methods for preparing cells cultured in vitro as fresh, frozen or fixed samples are known to those with skill in the art and exemplary methods are described herein. In one embodiment, assays of the invention are carried out on tissue samples that have been fixed and embedded in paraffin and a step of deparaffination may be carried out. A tissue sample may be fixed (i.e., preserved) by conventional methodology. See, e.g., Lee G. Luna, HT (ASCP) Ed., 1960, *Manual of Histological Staining Method of the Armed Forces Institute of Pathology* $3^{rd}$ edition, The Blakston Division McGraw-Hill Book Company, New York; Ulreka V. Mikel, Ed., 1994, *The Armed Forces Institute of Pathology Advanced Laboratory Methods in Histology and Pathology*, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology according to conventional techniques or as described herein. Once the tissue sample is embedded, the sample may be sectioned by a microtome according to conventional techniques. Sections may have a thickness in a range from about three microns to about twelve microns, and preferably, a thickness from about 5 microns to about 10 microns. In one embodiment, a section may have an area from about 10 mm$^2$ to about 1 cm$^2$. Once cut, the sections may be attached to slides by several standard methods. Examples of slide adhesives include, but are not limited to, silane, gelatin and poly-L-lysine. Paraffin-embedded sections may be attached to positively charged slides and/or slides coated with poly-L-lysine.

If paraffin has been used as the embedding material, the tissue sections are generally deparaffinized and rehydrated prior to detection of biomarkers. Tissue sections may be deparaffinized by several conventional standard methodologies. For example, xylenes and a gradually descending series of alcohols may be used according to conventional techniques described by the references provided herein. Alternatively, commercially available deparaffinizing non-organic agents such as Hemo-De® (CMS, Houston, Tex.) may be used.

Cell lysates of mammalian tissue culture cells or fresh or frozen tissues may be prepared by conventional cell lysis techniques (e.g., 0.14 M NaCl, 1.5 mM MgCl$_2$, 10 mM Tris-Cl (pH 8.6), 0.5% Nonidet P-40, and protease and/or phosphatase inhibitors as required). For fresh mammalian tissues, sample preparation may also include a tissue disaggregation step, such as crushing, mincing, grinding or sonication.

Stable cell lines expressing varying levels of Her-3 were generated. Cell lines stably expressing varying levels of a protein of interest are useful in validating new assays, such as the Her-3 VERATAG® assay, with respect to many parameters such as optimal antibody concentrations, accuracy, sensitivity, reproducibility, precision, linearity, specificity and dynamic range. HEK 293 cells were used to create the stable Her-3-expressing cell lines. HEK 293 cells are a specific cell line originally derived from human embryonic kidney cells transformed with adenovirus DNA (see Graham et al. (1977) J. Gen. Virol. 36: 59-74). HEK 293 cells are easy to grow in culture, transfect readily and have been widely used in cell biology research as well as in protein production for the biotechnology industry for many years. The generation of the Her-3-expressing cell lines is described in Example 1 and the results of ELISA assays to determine the level of Her-3 in each of these cell lines is shown in FIG. 1.

In a further preferred embodiment, the proximity probe comprises an antibody and a first nucleic acid and the binding compound comprises an antibody and a second nucleic acid, wherein the first and the second nucleic acids are complementary to each other and able to hybridize to determine the effective proximity and produce the signal, directly or indirectly, through hybridization. In a preferred embodiment, the proximity probe and/or binding compound is capable of binding specifically to Her-3. In a preferred embodiment, the binding compound and/or the proximity probe further comprises an antibody and each antibody binds to a different epitope on Her-3. In a preferred embodiment, the antibody is raised against one of the peptides having SEQ ID NOs: 1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively (Table 1B). In a preferred embodiment, the antibody is the antibody with the amino acid sequence having SEQ ID NOs:9 and 11 as set forth in Table 1A for the light and heavy chains, respectively, and/or SEQ ID NOs:10 and 12 as set forth in Table 1A for the light and heavy chains, respectively. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample as described herein. In a preferred embodiment, the sample is an FFPE sample or solubilized FFPE sample. In a preferred embodiment, the sample is a blood, plasma or lymph sample. In a preferred embodiment, the blood or plasma sample contains circulating tumor cells. In a preferred embodiment, the sample contains exosomes and/or other vesicles. In a preferred embodiment, the sample comprises cell lines. In a preferred embodiment, the measurement may be quantitative across a wide dynamic range. In a preferred embodiment, the wide dynamic range is about 2 logs. In a more preferred embodiment, the wide dynamic range is about 1-1.5 logs in breast cancer samples. In a preferred embodiment, the method provides a quantitative continuum of Her-3 expression. In a preferred embodiment, the measurement or quantity is sensitive to at least about 1000 receptors per cell to about 200,000 receptors per cell as determined by accuracy studies utilizing well-characterized cell line models and cross-validating technologies such as ELISA and flow cytometry. In a preferred embodiment, the measurement or quantity is sensitive to at least about 5000 receptors per cell to about 200,000 receptors per cell. In a preferred embodiment, the measurement or quantity is sensitive to at least about 10,000 receptors per cell to about 200,000 receptors per cell. In a preferred embodiment, the measurement or quantity is sensitive to at least about 25,000 receptors per cell to about 200,000 receptors per cell. In a preferred embodiment, the measurement is specific as determined using isotype control antibodies and comparison with conventional IHC methods. Examples of proximity probes and binding compounds, as set forth herein, can be found, for example, in U.S. Pat. Nos. 7,306,904; 7,320,860 and 7,351,528, each of which is incorporated by reference herein, including any drawings.

Proximity assays are increasingly useful for the understanding of the biological role of molecular complexes, as well as in the study of biomarkers. For example, binding compounds that specifically bind Her-3 or Her-3 in a complex can be coupled with many different detection systems to measure the presence and/or quantity of Her-3 or Her-3 in a complex. Any method known to one of skill in the art to be useful for determining an amount of Her-3 or Her-3 in a complex can be used in accordance with the present invention. Such methods include but are not limited to Foerster resonance energy transfer (FRET), bioluminescence resonance energy transfer (BRET), biomolecular fluoresence complementation, proximity ligation assay (PLA), scintillation proximity assays (SPA) and rolling circle amplification (RCA) or any other method for detecting nucleic acid duplexes formed by the proximity of a binding probe and a proximity probe with complementary strands of nucleic acids.

In conducting the methods of the invention, a combination of the assay components is made, including the sample being tested, the binding compounds and optionally the proximity probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages.

The amounts of each reagent can generally be determined empirically. The amount of sample used in an assay will be determined by the predicted number of target complexes present and the means of separation and detection used to monitor the signal of the assay. In general, the amounts of the binding compounds and the proximity probe can be provided in molar excess relative to the expected amount of the target molecules in the sample, generally at a molar excess of at least about 1.5, more desirably about 10-fold excess, or more. In specific applications, the concentration used may be higher or lower, depending on the affinity of the binding compound or proximity probe and the expected number of target molecules present on a single cell.

The assay mixture can be combined and incubated under conditions that provide for binding of the probes to the cell surface molecules, usually in an aqueous medium, generally at a physiological pH (comparable to the pH at which the cells are cultured), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually about 25° to 37° C.

In a preferred embodiment, the proximity probe comprises a cleaving probe that has a cleavage-inducing moiety and the at least one binding compound has one or more molecular tags attached to the binding compound by a cleavable linkage, wherein the cleavable linkage may be cleaved within the effective proximity, producing a signal that correlates with the presence and/or quantity of Her-3. In a preferred embodiment, the cleaving probe and/or binding compound is capable of binding specifically to Her-3. In a preferred embodiment, the binding compound and/or the proximity probe further comprises an antibody and each antibody binds to a different epitope on Her-3. In a preferred embodiment, the antibody is raised against one of the peptides having SEQ ID NOs: 1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs:19, 20 and 21, respectively, and (b) a heavy chain variable region comprising CDR1, CDR2 and CDR3 having sequences as set forth in SEQ ID NOs:22, 23 and 24, respectively. In a preferred embodiment, the antibody is the antibody with the amino acid sequence having SEQ ID NOs:9 and 11 as set forth in Table 1A for the light and heavy chains, respectively, and/or SEQ ID NOs:10 and 12 as set forth in Table 1A for the light and heavy chains, respectively. In a preferred embodiment, the sample is a biological sample. In a preferred embodiment, the sample is a tissue sample. In a preferred embodiment, the sample is a fixed sample, a frozen sample or a lysate. In a preferred embodiment, the sample is a tumor sample. In a preferred embodiment, the sample is a frozen tumor tissue sample. In a preferred embodiment, the sample comprises a tumor lysate. In a preferred embodiment, the sample comprises a breast cancer sample as described herein. In a preferred embodiment, the sample is an FFPE sample or solubilized FFPE sample. In a preferred embodiment, the sample is a blood, plasma or lymph sample. In a preferred embodiment, the blood or plasma sample contains circulating tumor cells. In a preferred embodiment, the sample comprises cell lines. In a preferred embodiment, the measurement may be quantitative across a wide dynamic range. In a preferred embodiment, the wide dynamic range is about 2 logs. In a more preferred embodiment, the wide dynamic range is about 1-1.5 logs in breast cancer samples. In a preferred embodiment, the method provides a quantitative continuum of Her-3 expression. In a preferred embodiment, the measurement or quantity is sensitive to at least about 1000 receptors per cell to about 200,000 receptors per cell as determined by accuracy studies utilizing well-characterized cell line models and cross-validating technologies such as ELISA and flow cytometry. In a preferred embodiment, the measurement or quantity is sensitive to at least about 5000 receptors per cell to about 200,000 receptors per cell. In a preferred embodiment, the measurement or quantity is sensitive to at least about 10,000 receptors per cell to about 200,000 receptors per cell. In a preferred embodiment, the measurement or quantity is sensitive to at least about 25,000 receptors per cell to about 200,000 receptors per cell. In a preferred embodiment, the measurement is specific as determined using isotype control antibodies and comparison with conventional IHC methods.

A two antibody proximity assay was optimized. Ab-6 (LabVision), a Her-3-specific monoclonal antibody with epitope specificity to the cytoplasmic terminus of Her-3, was conjugated to the VERATAG® reporter (Pro 11) for use as the proximity probe (Ab-6-Pro11). The proprietary monoclonal antibody, B9A11, was conjugated to biotin for use as the cleaving probe (B9A11-biotin) when complexed with streptavidin-methylene blue ("molecular scissors"). The assay methods are described in Example 5. Several cell lines that expressed varying levels of Her-3 ranging from very high levels (in one of the stably transfected HEK 293 cell lines, called 293H3-Clone 1) to moderate to low levels (MDA-MB-468 and MDA-MB-453, respectively) to low to no detectable Her-3 (in SKOV3 cells) were used in the optimization studies. The optimization process included determining the optimal antibody concentration for maximizing dynamic range (see Example 7 and FIG. 6), determining the accuracy of the assay (see Example 8 and FIG. 7), testing the sensitivity, reproducibility, and precision of the assay (see Example 9/FIG. 8, Example 10/FIG. 9 and Example 11/FIG. 10, respectively), the linearity of the assay in different sample sizes (see Example 12 and FIG. 11) and the specificity of the assay by testing for non-specific binding using isotype controls (see Example 13 and FIG. 12).

Isotype controls are typically performed to eliminate the possibility that the binding results are due to the particular isotype of the antibody rather than the individual antibody. Additionally, one skilled in the art will appreciate that any signal "noise" seen in the isotype controls can be subtracted from the total signal, potentially yielding a more refined result. When an isotype control experiment was performed, the contribution of non-specific binding was observed to be very low (see FIG. 12).

Many advantages are provided by measuring Her-3 or the Her-3 in a complex using releasable molecular tags, including separation of released molecular tags from an assay mixture providing greatly reduced background and a significant gain in sensitivity and separation and detection providing a convenient multiplexing capability so that multiple receptor complex components may be readily measured simultaneously in the same assay. Assays employing such tags can have a variety of forms and are disclosed in the following references: U.S. Pat. Nos. 7,105,308; 6,627,400; 7,402,397; 7,402,398 and 7,402,399, as well as International Patent Publication No. WO 2004/011900, each of which is incorporated herein by reference in its entirety. A wide variety of separation techniques may be employed that can distinguish molecules based on one or more physical, chemical or optical differences among molecules being separated including electrophoretic mobility, molecular weight, shape, solubility, pKa, hydrophobicity, charge, charge/mass ratio or polarity. In one embodiment, molecular tags in a plurality or set differ in electrophoretic mobility and optical detection characteristics and are separated by electrophoresis. In another embodiment, molecular tags in a plurality or set may differ in molecular weight, shape, solubility, pKa, hydrophobicity, charge, polarity and are separated by normal phase or reverse phase HPLC, ion exchange HPLC, capillary electrochromatography, mass spectroscopy or gas phase chromatography.

Sets of molecular tags are provided that can be separated into distinct bands or peaks by a separation technique after they are released from binding compounds. Identification and quantification of such peaks provides a measure or profile of the presence and/or amounts of Her-3. Molecular tags within a set may be chemically diverse; however, for convenience, sets of molecular tags are usually chemically related. For example, they may all be peptides or they may consist of different combinations of the same basic building blocks or monomers or they may be synthesized using the same basic scaffold with different substituent groups for imparting different separation characteristics. The number of molecular tags in a plurality may vary depending on several factors including the mode of separation employed, the labels used on the molecular tags for detection, the sensitivity of the binding moieties and the efficiency with which the cleavable linkages are cleaved.

Measurements made directly on tissue samples may be normalized by including measurements on cellular or tissue targets that are representative of the total cell number in the sample and/or the numbers of particular subtypes of cells in the sample (see, for example, United States Patent Application Publication No. US 2009/0191559 which is incorporated by reference herein in its entirety, including any drawings). The additional measurement may be preferred, or even necessary, because of the cellular and tissue heterogeneity in patient samples, particularly tumor samples, which may comprise substantial fractions of normal cells.

In one embodiment, a binding compound can be represented by the following formula:

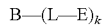

$$B\text{—}(L\text{—}E)_k$$

wherein B is binding moiety; L is a cleavable linkage and E is a molecular tag. In homogeneous assays, cleavable linkage, L, may be an oxidation-labile linkage, and more preferably, it is a linkage that may be cleaved by singlet oxygen. The moiety "—$(L\text{—}E)_k$" indicates that a single binding compound may have multiple molecular tags attached via cleavable linkages. In one aspect, k is an integer greater than or equal to one, but in other embodiments, k may be greater than several hundred, e.g. 100 to 500 or k is greater than several hundred to as many as several thousand, e.g. 500 to 5000. Usually each of the plurality of different types of binding compounds has a different molecular tag, E. Cleavable linkages, e.g. oxidation-labile linkages, and molecular tags, E, are attached to B by way of conventional chemistries.

Preferably, B is an antibody that specifically binds to a target, such as Her-3. Antibodies specific for Her-3 epitopes are provided in the examples set forth herein. Antibody compositions may be readily formed from a wide variety of commercially available antibodies, either monoclonal or polyclonal or by methods disclosed herein.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages within an effective proximity of the proximity probe are cleaved. Typically, such an agent must be activated by making a physical or chemical change to the reaction mixture so that the agent produces a short lived active species that diffuses to a cleavable linkage to affect cleavage.

In a non-homogeneous format, because specifically-bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen or the like, but also linkages that are labile to agents that operate throughout a reaction mixture, such as base-labile linkages, photocleavable linkages, linkages cleavable by reduction, linkages cleaved by oxidation, acid-labile linkages and peptide linkages cleavable by specific proteases. References describing many such linkages include Greene and Wuts, 1991, *Protective Groups in Organic Synthesis, Second Edition*, John Wiley & Sons, New York; Hermanson, 1996, *Bioconjugate Techniques*, Academic Press, New York; and U.S. Pat. No. 5,565,324, each of which is incorporated by reference herein.

Molecular tag, E, in the present invention may comprise an electrophoric tag as described in the following references when separation of pluralities of molecular tags are carried out by gas chromatography or mass spectrometry: See, e.g., Zhang et al., 2002, *Bioconjugate Chem.* 13:1002-1012; Giese, 1983, *Anal. Chem.* 2:165-168; and U.S. Pat. Nos. 4,650,750; 5,360,819; 5,516,931; and 5,602,273, each of which is hereby incorporated by reference in its entirety.

Molecular tag, E, is preferably a water-soluble organic compound that is stable with respect to the active species, especially singlet oxygen, and that includes a detection or reporter group. Otherwise, E may vary widely in size and structure. In one embodiment, E has a molecular weight in the range of from about 50 to about 2500 daltons, more preferably, from about 50 to about 1500 daltons. E may comprise a detection group for generating an electrochemical, fluorescent or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one embodiment, the chromatographic or electrophoretic separation characteristic is retention time under a set of standard separation conditions conventional in the art, e.g., voltage, column pressure, column type, mobile phase or electrophoretic separation medium. In another embodiment, the optical property is a fluorescence property, such as emission spectrum, fluorescence lifetime or fluorescence intensity at a given wavelength or band of wavelengths. Preferably, the fluorescence property is fluorescence intensity. One or two or more of the molecular tags of a plurality may have identical migration or retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by a conventional capillary electrophoresis apparatus, either in the presence or absence of a conventional sieving matrix. During or after electrophoretic separation, the molecular tags are detected or identified by recording fluorescence signals and migration times (or migration distances) of the separated compounds or by constructing a chart of relative fluorescent and order of migration of the molecular tags (e.g., as an electropherogram). Preferably, the presence, absence and/or amounts of molecular tags are measured by using one or more standards.

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH and hydroxyl radicals, phenoxy radical, superoxide and the like. Illustrative quenchers for active species that cause oxidation include polyenes, carotenoids, vitamin E, vitamin C, amino acid-pyrrole N-conjugates of tyrosine, histidine and glutathione. See, e.g. Beutner et al., 2000, *Meth. Enzymol.* 319:226-241.

One consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one embodiment, cleavable linkages preferably are within about 1000 nm and preferably within about 20-200 nm of a bound cleavage-inducing moiety. More preferably, for photosensitizer cleavage-inducing moieties generating singlet oxygen, cleavable linkages are within about 20-100 nm of a photosensitizer in a receptor complex. One of ordinary skill in the art will recognize that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation or chemical activation will release a molecule of singlet oxygen. The best known members of this class of compounds include the endoperoxides such as 1,4-biscarboxyethyl-1,4-naphthalene endoperoxide, 9,10-diphenylanthracene-9,1 0-endoperoxide and 5,6,11,12-tetraphenyl naphthalene 5,12-endoperoxide. Heating or direct absorption of light by these compounds releases singlet oxygen. Further sensitizers are disclosed by Di Mascio et al. 1994, *FEBS Lett.* 355:287 and Kanofsky, 1983, *J. Biol. Chem.* 258:5991-5993; Pierlot et al., 2000, *Meth. Enzymol.* 319:3-20.

Photosensitizers may be attached directly or indirectly, via covalent or non-covalent linkages, to the antibodies. Guidance for constructing such compositions are available in the literature, e.g. in the fields of photodynamic therapy, immunodiagnostics and the like. Exemplary guidance may be found in Ullman et al., 1994, *Proc. Natl. Acad. Sci. USA* 91, 5426-5430; Strong et al., 1994, *Ann. New York Acad. Sci.* 745: 297-320; Yarmush et al., 1993, *Crit. Rev. Therapeutic Drug Carrier Syst.* 10: 197-252; and U.S. Pat. Nos. 5,709,994, 5,340,716, 6,251,581, and 5,516,636.

A large variety of light sources are available to photoactivate photosensitizers to generate singlet oxygen. Both polychromatic and monochromatic sources may be used as long as the source is sufficiently intense to produce enough singlet oxygen in a practical time duration. The length of the irradiation depends on the nature of the photosensitizer, the nature of the cleavable linkage, the power of the source of irradiation and its distance from the sample. In general, the period for irradiation may be less than about a second to as long as about 3 hours and is usually in the range of 15 minutes to 2 hours. Exemplary light sources include lasers such as, e.g., helium-neon lasers, argon lasers, YAG lasers, He/Cd lasers and ruby lasers; photodiodes; mercury, sodium and xenon vapor lamps and incandescent lamps such as, e.g., tungsten and tungsten/halogen and flashlamps. An exemplary photoactivation device suitable for use in the methods of the invention is disclosed International Patent Publication No. WO 03/051669, which is incorporated by reference herein, including any drawings. In such embodiments, the photoactivation device is an array of light emitting diodes (LEDs) mounted in housing that permits the simultaneous illumination of all the wells in a 96-well plate.

Examples of photosensitizers that may be utilized in the present invention are those that have the above properties and those disclosed by U.S. Pat. Nos. 5,536,834, 5,763,602, 5,565,552, 5,709,994, 5,340,716, 5,516,636, 6,251,581 and 6,001,673; published European Patent Application No. 0484027; Martin et al., 1990, *Methods Enzymol.* 186:635-645 and Yarmush et al., 1993, *Crit. Rev. Therapeutic Drug Carrier Syst.* 10:197-252, all of which are incorporated by reference herein, including any drawings. As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically according to routine methods.

Following cleavage, the sample can then be analyzed to determine the identity of molecular tags that have been released. Where an assay employing a plurality of binding compounds is employed, separation of the molecular tags will generally precede their detection. The methods for both separation and detection are determined in the process of designing the molecular tags for the assay. A preferred mode of separation employs electrophoresis, in which the various tags are separated based on known differences in their electrophoretic mobilities.

In a second aspect, the invention is drawn to a method for determining whether a subject with a cancer is likely to respond to treatment with a targeted therapy, for predicting a time course of disease and/or for predicting the probability of a significant event in the time course of the subject's cancer, comprising measuring in a biological sample from the subject's cancer an amount of Her-3, wherein the method is dependent on the level of Her-3. In certain embodiments, if the level of Her-3 is high, the patient is less likely or unlikely to respond to the targeted therapy. In certain embodiments, if the level of Her-3 is low, the patient is more likely to respond to the targeted therapy. In certain embodiments, as described in more detail herein, the therapy is a Her acting agent. In further embodiments, the therapy is at least one of a Her-2 acting agent or a Her-3-targeted agent.

In a certain embodiments, the breast cancer is early stage (i.e., adjuvant) breast cancer or metastatic breast cancer. In certain embodiments, the level of Her-2 expression in the breast cancer is high. In certain embodiments, high Her-2 expression is a log $10H2T \geq$ about 1.14-1.25. In certain embodiments, the high Her-2 expression comprises expression that is very high and/or moderately high. In certain embodiments, the very high Her-2 expression is a log $10H2T \geq$ about 1.84-2.21. Or, other ranges may be used depending upon the patient cohort.

In a preferred embodiment, a time course is measured by determining the time between significant events in the course of a patient's disease, wherein the measurement is predictive of whether a patient has a long time course. In a preferred embodiment, the significant event is the progression from primary diagnosis to death. In a preferred embodiment, the significant event is the progression from primary diagnosis to metastatic disease. In a preferred embodiment, the significant event is the progression from primary diagnosis to relapse. In a preferred embodiment, the significant event is the progression from surgery to death. In a preferred embodiment, the significant event is the progression from surgery to relapse. In a preferred embodiment, the significant event is from surgery to metastases. In a preferred embodiment, the significant event is the progression from metastatic disease to death. In a preferred embodiment, the significant event is the progression from metastatic disease to relapse. In a preferred embodiment, the significant event is the progression from relapse to death. In a preferred embodiment, the time course is measured with respect to overall survival rate, time to progression and/or using the RECIST or other response criteria.

Figure 13:
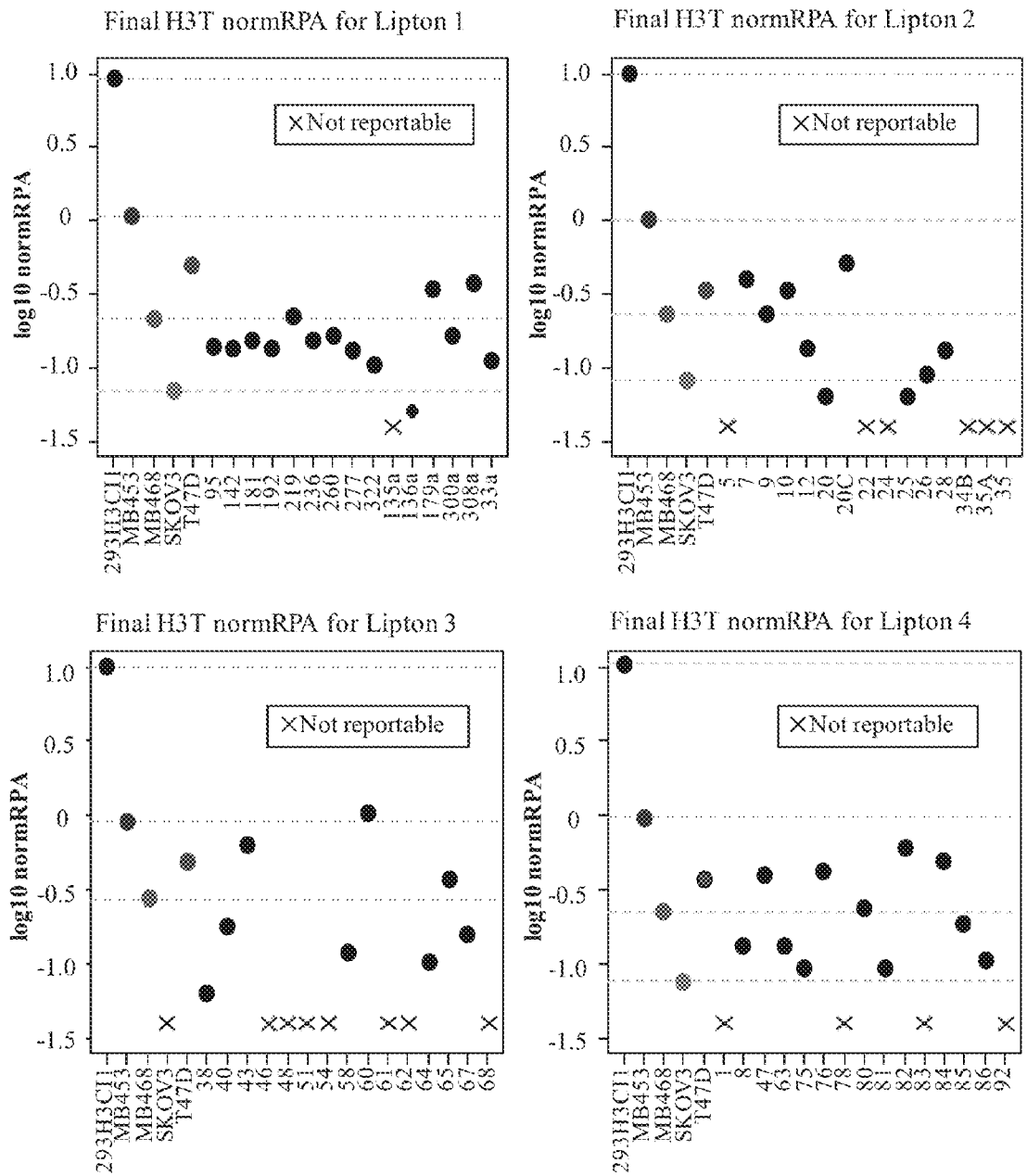
FIG. 13 shows VERATAG® data on tumor samples from the International Serum Her-2/neu Study Group trial. This cohort of patients (n=105) was prospectively observed during trastuzumab treatment between 1999 and 2006. All patients were determined to be Her-2 positive by either IHC or FISH and had not been exposed to trastuzumab prior to the study. The samples were evaluated for HER3 levels using the HER3 VERATAG® assay in eight separate batches. The results are shown in the 8 panels in this figure. Each panel also includes results for 5 control cell lines: 293H3-Clone 1, MDA-MB-453, MDA-MB-468, SKOV3 and T47D (shown on the left of each panel). Results are shown in $\log_{10}$ normalized RPA units.
Figure 13:
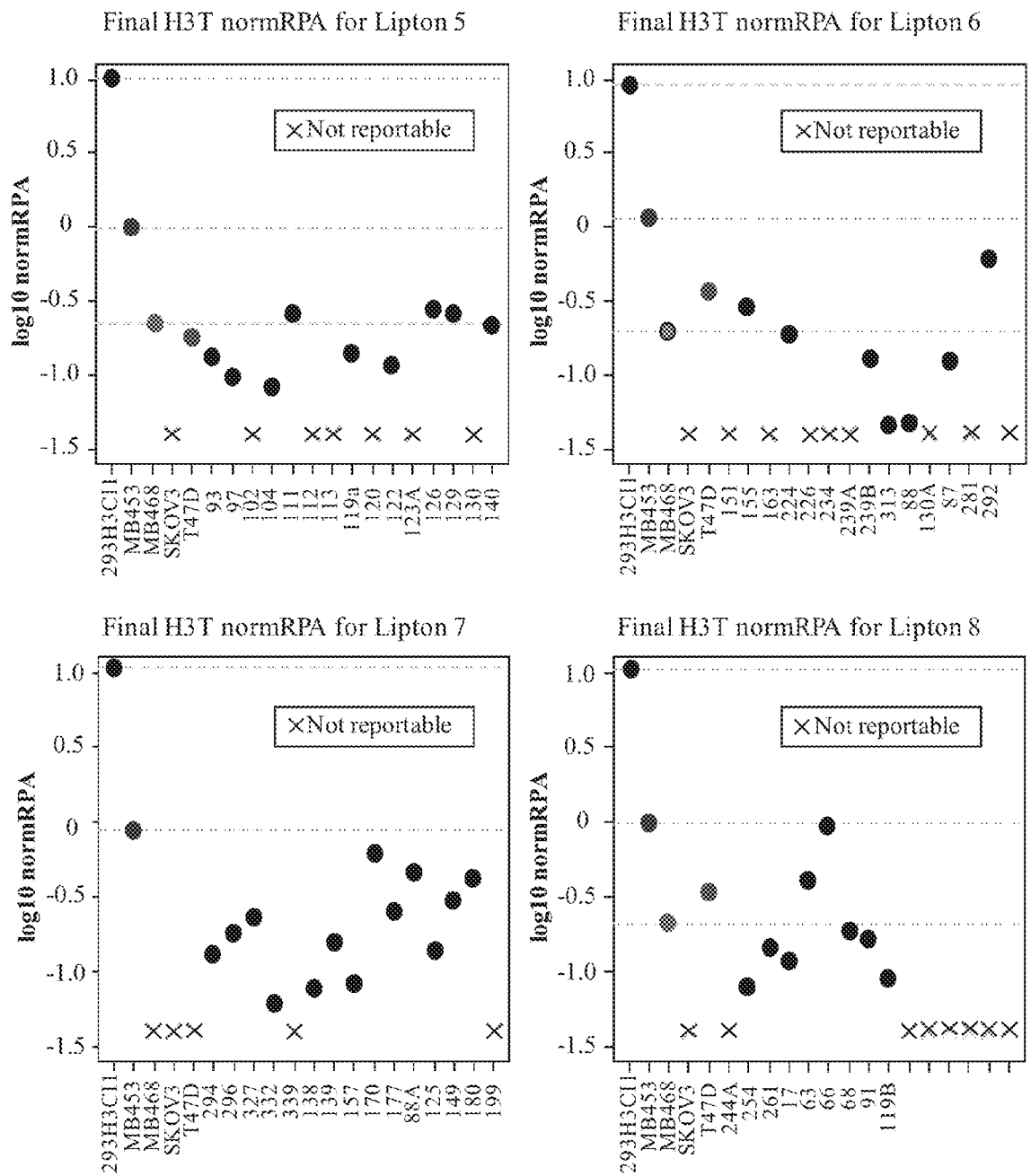

The Her-3 VERATAG® assay was used to examine the Her-3 levels in a cohort of patients from the International Serum Her-3/neu Study Group trial. These patients (n=105) were selected primarily by IHC for Her-2 positively performed at a central location by a single pathologist and all received trastuzumab. Only patients with Her-2 over-expressing tumors (>10% of tumor cells IHC 3+ as determined by HercepTest) and/or ErbB2-amplified (with positive FISH testing mandatory on all IHC 2+ cases) metastatic breast cancer were included in this study (see Example 14 for additional details). The Her3 VERATAG® assay was performed on these patient samples and out of 105 samples on which the assay was performed, 85 had measurable Her-3 levels above the limit of detection (8 had no detectable tumor, 1 sample had a fluorescein failure, and 8 samples were below the limit of detection and considered low/negative in the assay). The results are shown in FIG. 13.

Her-3 levels and in particular Her-3 levels in Her-2 positive tumors have been implicated in having prognostic value with respect to the time course of disease progression and overall survival as well as response to therapy and particularly with respect to escape from EGFR-family-targeted therapeutics. See Sergina et al. (2007) *Nature* 445:437-441, Osipo et al. (2007) *Int J Oncol.* 30:509-520, De Alava et al. (2007) *Clinical Oncol.* 25:2656-2663, Ma and Bose (2008) *E-Updates* in HER1 and HER2 Targeting in Breast Cancer, Volume 2, Tovey et al. (2006) *J. Pathol.* 210:358-362, Menendez and Lupu (2007) *Breast Cancer Res.* 9:111, Fuchs et al. (2006) *Anticancer Res.* 26:4397-4402, Lee-Hoeflich et al. (2008) *Cancer Res.* 68:5878-5886.

Her-3 expression has been examined in many cancers, including tumors of patients treated with therapeutics targeted to EGFR family members (e.g., trastuzumab, pertuzumab, lapitinib, cetuximab, gefitinib and erlotinib) as well as chemotherapeutics. In comparing Her-family member levels with clinical outcome, data suggest specifically that Her-3 expression and/or the relative amounts of Her-2 and Her-3 may be of use as a prognostic and predictive diagnostic biomarker in ovarian cancer (see Amier et al. (2008) *J Clin. Oncol.* 26:abstract 5552, Amier et al. (2008) Meeting: 2008 *Molecular Markers*, abstract 25 and Xu et al. (1999) *Clin. Cancer Res.* 5:3652-3660) and non-small-cell lung cancer (Cappuzzo et al. (2005) *Brit. J. Cancer* 93:1334-1340). In a preferred embodiment, the method further comprises determining whether the level of Her-3 is high or low by dividing a sample group of Her-2-positive patients into at least two subgroups comprising one subgroup with a high amount of Her-3 and at least one other subgroup with a low amount of Her-3, wherein if the Her-3 is low, then the patient is likely to respond to Her-2-targeted therapy, the time course of the disease is likely to be long and the patient is not likely to have a significant event. In a preferred embodiment, the subject's cancer is breast cancer, colorectal cancer, ovarian cancer, bladder cancer, prostate cancer, non-small cell lung cancer, melanoma, pharyngeal cancer, pancreatic cancer, esophageal cancer, glioma, bile duct carcinoma, biliary tract carcinoma, cholangiocarcinoma, gastric cancer, endometrial cancer, gall bladder cancer, squamous cell carcinoma or basal cell carcinoma. In a preferred embodiment, the subject's cancer is breast cancer, melanoma, colorectal cancer or ovarian cancer. In a preferred embodiment, the subject's cancer is a Her-2 positive breast cancer. In a preferred embodiment, the breast cancer is early stage (i.e., adjuvant) breast cancer or metastatic breast cancer.

In a preferred embodiment, the targeted therapy is at least one Her family-targeted agent. In a preferred embodiment, the Her family-targeted agent is a multi- or single-targeted agent. In a preferred embodiment, the multi-targeted agent is a dual kinase inhibitor or a bispecific antibody. In a preferred embodiment, the Her family targeted agent is trastuzumab, lapatinib or pertuzumab. In a preferred embodiment, the at least one Her family-targeted agent is at least two agents, wherein the at least two agents are one or more Her-2-targeted monoclonal antibodies and/or EGFR-targeted monoclonal antibodies and/or an EGFR and Her-2 dual kinase inhibitor. In a preferred embodiment, the monoclonal antibody is trastuzumab. In a preferred embodiment the EGFR-targeted monoclonal antibody is cetuximab or panitumumab. In a preferred embodiment, the EGFR-targeted monoclonal antibody is zalutumumab, nimotuzumab, and matuzumab. In a preferred embodiment, the dual kinase inhibitor is lapatinib, erlotinib or gefitinib. In a preferred embodiment, the targeted therapy is a Her-3 or Her-3 signaling pathway acting agent. In a preferred embodiment, the Her-3 or Her-3 signaling pathway targeted agent is a Her-3 monoclonal antibody, a Her-3 dimerization inhibitor, a Her-3 phosphorylation inhibitor and/or an inhibitor of a Her-3 signaling pathway member selected from the group consisting of PI3K, Akt, mTOR, ERK½, or PYK2. In a preferred embodiment, likeliness to respond, likeliness to have a long time course and/or likeliness to have a significant event is measured as an overall survival rate, as time to progression, as disease-free survival, as progression-free survival, and/or as objective tumor response using the RECIST criteria. Signal transduction refers to any process by which cells convert one kind of signal into another. Typically, this involves some type of signal on the cell surface (for example, the binding of a ligand to a cell surface receptor), followed by a cascade of biochemical reactions inside the cell, which are carried out by enzymes, resulting in a signal transduction pathway or signaling pathway, effecting a multitude of cellular functions. In the case of the EGFR family of tyrosine kinase receptors, each of the four receptors in the family has an extracellular domain, comprising both a dimerization domain and a ligand-binding domain, as well as a trans-membrane domain and an intracellular domain with tyrosine kinase activity (see Burgess et al. (2003) *Mol Cell.* 12:541-542). In Her-3, the kinase domain is not functional but through dimerization with other family members, Her-3 can exert significant signaling pathway effects. Evidence suggests that cooperation of multiple ErbB receptors and ligands is required for initiating cell transformation. When activated, this family of receptors sustains a complex network of signaling pathways. All EGFR family members have been found to be expressed and/or altered in a variety of cancers and may play a significant role in tumor development, including proliferation, apoptosis, and metastasis (see Burgess (2008) *Growth Factors* 26:263-274 and Normanno et al. (2006) *Gene* 366:2-16). Intense interest in targeting the EGFR family members (see Bianco et al. (2007) *Int. J. Biochem. Cell. Biol.* 39:1416-1431), particularly EGFR and Her-2, has resulted in several approved targeted therapeutics. Based on promising preclinical data in both in vitro and in vivo test models, the results in clinical trials have been somewhat disappointing, resulting in increased interest in other family members such as Her-3, as well as downstream signaling pathway members.

Her-3 signaling has been linked to cancer and, in particular, Her-2/Her-3 dimer formation may be crucial for increased aggression in tumors that over-express Her-2, leading to interest in targeted therapeutics that inhibit dimer formation as well as downstream pathways activated by Her-3. Her-3 is particularly adept at signaling because it has 6 binding sites for phosphoinositide 3'-kinases (PI3K) which in turn, activate protein kinase B (also called AKT). The "PI3K/AKT" signaling pathway has been shown to be required for an extremely diverse array of cellular activities—most notably cellular proliferation and survival—fueling the interest in targeting both Her-3 as well as downstream signaling pathway members to create novel targeted therapeutics or to potentiate the therapeutic value of current EGFR-family targeted therapeutics. (For review, see Stern (2008) *J Mammary Gland Biol Neoplasia* 13:215-223, Sithanandam and Anderson (2008) *Cancer Gene Ther.* 15:413-448 and Arkin and Moasser (2008) *Curr. Opin. Investig. Drugs* 9:1264-1276).

In a preferred embodiment, whether the cancer is Her-2 positive is determined by IHC, FISH, CISH, quantitative mRNA, hybridization array or VERATAG®. In a preferred embodiment, determining the level of Her-3 is performed using IHC, FISH, CISH, quantitative mRNA, hybridization array or VERATAG®. In a preferred embodiment, the method further comprises determining whether an amount of Her-3 protein is low by comparing the amount of Her-3 in the subject's cancer to a pre-determined cutoff. In a preferred embodiment, the method further comprises determining the level of Her-3 by dividing a sample group of Her-2-positive patients into at least two subgroups comprising one subgroup with a high amount of Her-3 and at least one other subgroup with a low amount of Her-3, wherein if the Her-3 is high, then the patient is unlikely to respond to Her-2-targeted therapy, the time course of the disease is likely to be short and/or the patient is likely to have a significant event.

In a preferred embodiment, the method further comprises determining that a subject is afflicted with a Her-2 positive cancer that is unlikely to respond to treatment according to a method of the invention, then advising a medical professional of the treatment option of administering to the subject an effective amount of a different therapeutic agent.

In a third aspect, the invention is drawn to a purified antibody that binds to Her-3. In a preferred embodiment, the antibody is a polyclonal antibody or a monoclonal antibody. In a preferred embodiment, the antibody is a monoclonal antibody. In a preferred embodiment, the antibody is raised against one of the peptides having SEQ ID NOs:1-8, as set forth in Example 2 and shown in FIG. 2A. In a preferred embodiment, the antibody is a monoclonal antibody comprising (a) a light chain variable region comprising CDR1, CDR2 and CDR3 having sequences as set forth in SEQ ID NOs:13, 14 and 15, respectively, and (b) a heavy chain variable region comprising CDR1, CDR2 and CDR3 having sequences as set forth in SEQ ID NOs:16, 17 and 18, respectively; and/or a monoclonal antibody comprising (a) a light chain variable region comprising CDR1, CDR2 and CDR3 having sequences as set forth in SEQ ID NOs: 19, 20 and 21, respectively, and (b) a heavy chain variable region comprising CDR1, CDR2 and CDR3 having sequences as set forth in SEQ ID NOs:22, 23 and 24, respectively (Table 1B). In a preferred embodiment, the antibody is the antibody with the amino acid sequence having SEQ ID NOs:9 and 11 as set forth in Table 1A for the light and heavy chains, respectively, and/or SEQ ID NOs:10 and 12 as set forth in Table 1A for the light and heavy chains, respectively.

In a preferred embodiment, the invention is drawn to the DNA encoding the antibody. The DNA encoding the monoclonal antibodies is isolated and sequenced using techniques commonly known to those skilled in the art of cloning. Once isolated, the DNA can be ligated into expression vectors and transfected into appropriate host cells to obtain recombinant antibodies from cultured cells (see Plueckthun (1992) *Immunological Rev.* 130: 151-188).

Those with skill in the art will appreciate that the amino acid sequence of an antibody can be modified and that modifications may be desirable to enhance the properties of the antibody for therapeutic, analytical or diagnostic use. Further it will be appreciated that one or more amino acids in these antibodies may be changed by insertion, deletion or substitution without appreciably diminishing the binding characteristics of the antibody. Exemplary amino acid changes would be substitutions using amino acids with similar molecular characteristics (i.e., conservative substitutions, e.g., changing amino acids from within the following subgroups of aromatic amino acids, acidic amino acids, basic amino acids or amino acids with amides or sulphurs). Other non-conservative substitutions or insertions may be made without appreciably altering molecular integrity or binding characteristics. Further, some amino acid changes or collection of amino acid changes will enhance properties of the antibody, including but not limited to, better binding affinity, greater stability, (e.g., resistance to proteases) selectivity and/or ease of production. Methods for changing amino acid sequences and/or selecting for molecules with better properties are known to those with skill in the art. Preferably, in intact antibodies, the degree of sequence identity after modification is at least 50% and more preferably, at least 75% and most preferably at least 90-95%. Each of these antibodies is intended to be within the scope of the contemplated invention.

In a preferred embodiment, antibodies targeted to Her-3 may be used to develop additional Her-3-targeted molecules. Modifications of the antibodies described herein may be desirable to improve qualities including, but not limited to, increasing effector function, decreasing immunogenicity, increasing stability, improving pharmacologic properties such as serum half-life and aiding in ease and yield of production. Each of these targeted molecules is intended to be within the scope of the contemplated invention.

In a preferred embodiment, humanized antibodies comprising the antigen binding regions of the antibodies described herein (see Table 1A) in a human framework may be used for therapeutic applications. Several methods for humanizing antibodies have been reported (see Jones et al. (1986) *Nature* 321:522-525, Riechmann et al. (1988) *Nature* 332:323-327 and Verhoeyen et al. (1988) *Science* 239:1534-1536). Typically, the non-human sequences of the variable domain are screened computationally against the entire repertoire of human light and heavy chain variable domain sequences to find the human variable framework sequences closest to the rodent sequences (see Sims et al. (1993) *J.*

Immunol. 151:2296-2308, Chothia et al. (1987) *J. Mol. Biol.* 186:901-917). Alternatively, consensus frameworks can be used (see Carter et al. (1992) *Proc. Natl. Acad. Sci. USA* 89:4285-4289 and Presta et al. (1993) *J. Immunol.* 151:2623-2632). In a preferred embodiment, computer-aided design is used to select sequences that confer stability and retain or improve binding characteristics. Each of these is intended to be within the scope of the contemplated invention.

In another embodiment, the antibody CDRs may be used to create targeted binding molecules that bind the same epitope in Her-3 but are contained within a framework that is not a native antibody. For example, one skilled in the art would appreciate that methods are available for creating binding molecules in which the framework may be a portion of an antibody, for example, an scFv or F(ab')$_2$ (see WO 93/16185 and Carter et al. (1992) *Bio/Technology* 10:163-167, respectively), each of which is incorporated by reference herein. One skilled in the art may also appreciate that a completely unrelated protein (such as a bacterial beta-lactamase) can properly display the binding domain(s) to form a binding compound. In this sense, related antibodies, as defined herein, are intended to be within the scope of the invention.

The antibody may act therapeutically through binding alone or through other properties (e.g., enzymatic activity or toxic warheads). In one embodiment, the targeted protein may be modified to exert a therapeutic effect or a greater therapeutic effect via antigen-dependent cell-mediated cytotoxicity (ADCC) or complement-dependent cytotoxicity (CDC). In another embodiment, toxins may be conjugated to the antibody or targeted protein. Exemplary small molecule toxins include but are not limited to maytansine, calicheamicin and CC-1065 (see, e.g., Carter and Senter (2008) *Cancer J.* 14:154-169). Additionally, radiolabels can be linked to antibodies to create targeted therapeutics. Biologic toxins may also be linked to targeted proteins and include, but not be limited to, diphtheria toxin, *Pseudomonas* exotoxin, abrin and ricin (see Kreitman (2006) *AAPS J.* 18:E532-551)

In a further embodiment, the targeted antibodies (or fragments thereof) may be fused to enzymes for use in antibody-directed enzyme prodrug therapy (ADEPT; see Bagashawe (1987) *Br. J. Cancer* 58:700-703 and Senter et al. (1988) *Proc. Natl. Acad. Sci. USA* 85:4842-4846). In another embodiment, the antibodies or targeted proteins may be fused to molecules such as polyethylene glycol, that enhance pharmacologic properties, such as serum half-life (see Harris and Chess (2003) *Nat. Rev. Drug Discov.* 2:214-221).

EXAMPLES

The present invention may be better understood by reference to the following non-limiting examples.

Example 1

Generation of Stable Cell Lines Expressing Varying Levels of HER3 Protein

A commercially available cDNA (Origene Technologies, Inc.) for full-length HER3 (NM_001982.2) was digested with the restriction enzymes Not I and Xba I and the resulting fragment was subcloned into pcDNA.3 1 Zeocin selectable expression vector. The resulting plasmid was transformed into bacteria and screened to verify the correct insert. Positive clones were sequence verified, expanded in bacteria and the plasmid purified using the Qiagen Maxi-prep kit. Human embryonic kidney cells (HEK-293) were purchased from the American Type Culture Collection and maintained in DMEM supplemented with 10% FBS, 1× penicillin-streptomycin (100× is 10,000 U/ml penicillin-G and 10,000 ug/ml streptomycin), and Glutamax (GIBCO) at 37 C in 5% $CO_2$. The day prior to transfection, the cells were split to approximately 25-30% confluence and incubated overnight in media without pen-strep. The cells were then transfected with Fugene HD (Roche) according to the manufacturer's instructions. The next day the media was replaced with fresh complete media and the cells were incubated for 48 hours prior to the addition of 400 mg/mL Zeocin (Invitrogen) in complete media. The concentration of Zeocin was determined by performing a killing curve using varying concentrations of Zeocin on wild-type 293 cells that do not contain the transfected plasmid. Approximately 16 Zeocinresistant clones were isolated using cloning rings and frozen in liquid nitrogen. A subset of the original clones could be expanded successfully and tested using an HER3-specific ELISA kit (R & D Systems, Inc), according to the manufacturers instructions and verified as over-expressing HER3 (FIG. 1). One clone with high expression of HER3 as demonstrated by ELISA (293-H3 clone 1) was selected as a control for use in the optimized assay.

Example 2

Generation and Screening of Antibodies Against HER3

A HER3-specific monoclonal antibody (Ab-6) with epitope specificity to the cytoplasmic terminus of HER3 was purchased from LabVision. The VERATAG® reporter (Pro1 1) and streptavidin-conjugated methylene blue ("molecular scissors") were synthesized and purified according to protocol described previously (see, for example, above and U.S. Pat. No. 7,105,308, which is incorporated by reference herein, including any drawings). Antibody-VERATAG® and antibody-biotin conjugates, i.e., Ab6-Pro11 and B9A11-biotin, were made using sulfo-NHS-LC-LC-biotin (Pierce) as linker according to manufacturer's protocol and conjugation products purified by HPLC (Agilent). A series of proprietary antibodies were generated as follows. Mice were immunized with fixed 293 clone 13 cells or a series of peptides representing different epitopes contained within the c-terminal region of the HER3 protein (FIG. 2A). During the immunization period, each mouse received several immunizations over a 4 week period. Hybridomas were produced and clones isolated using limiting dilution. Conditioned media from individual clones were profiled by a series of assays, including Cell-Spot™ or ELISA screening, followed by scale-up and then further screening by immunohistochemistry (IHC) (FIG. 2B), and then finally by VERATAG® Technology using either a chemical release method (Methylene Blue) (FIG. 2C) or the dual-antibody light release method (FIG. 2D). Several antibodies that performed well using these methods and are described in FIG. 2A. One in particular, B9A11, was the most robust and gave the best dynamic range and sensitivity and was carried forward to develop the final format of the assay as described below in Example 5.

Example 3

Generation of Blocks and FFPE Sections from a Panel of Cell Lines Expressing Varying Levels of HER3 by FACS and ELISA Three cell lines with varying expression of HER3 protein, MDA-MB-453, MDA-MB-468 and SKOV-3, were purchased from American Type Cell Culture Collection. MDA- MB-453 and MDA-MB-468 cell lines were maintained at 37° C. and 5% $CO_2$ in Dulbecco's modified Eagle medium (DMEM), 10% FBS, 1× penicillin-streptomycin and 1× Glutamax. SKOV3 cells were maintained at 37° C. and 5% $CO_2$ in McCoy's 5a Media supplemented with 10% FBS, 1× penicillin-streptomycin and 1× Glutamax (GIBCO). 293-H3 clone 1 cells were maintained at 37° C. and 5% $CO_2$ in DMEM supplemented with 10% FBS, 1× penicillin-streptomycin and 1× Glutamax. Cells were grown to near confluence on at least ten 500 mm culture plates for each cell line. After removal of medium, the cells were washed once with cold 1×PBS and 15 mL of 1× Pen-fix (Thermo Scientific) was added to each plate. Cells were scraped and the cell solution fixed overnight (>16 hrs) at 4° C. Following the overnight fixation the cells were centrifuged at 3200×g for 15 min. The cell pellet was transferred to a rubber O-ring, wrapped with filter paper and placed in a processing cassette. An automatic Tissue-Tek processor was used for processing. Briefly, the cell pellet was exposed to increasing concentrations of alcohol, Clear-rite (xylene substitute) and paraffin. After processing, the pellet was embedded in a block using a paraffin embedding station. All solvents used for cell pellet processing were obtained from Richard-Allen Scientific. The proportion of the same lot of cells was tested for HER3 receptor number using flow cytometry by the following method. A whole cell lysate was prepared from the preparation of cells for quantifying levels of HER3 receptor by using a commercially available ELISA kit and following manufacturer's recommendations (Human ErbB3-DuoSet ELISA; R & D systems). Sections of 7 um in thickness were sliced with a microtome (LEICA) and placed on positively charged glass slides (VWR). Slides were air-dried for 30 min and then baked in a heated oven set at 70° C. for 1.5 hr. All sample slides were stored at 4° C. for future assays. Results of the ELISA, flow cytometry, IHC and VERATAG® comparison are shown in FIG. 3.

Example 4

Generation of Sections from Commercially Available Breast Cancer FFPE Sections

Figure 4:
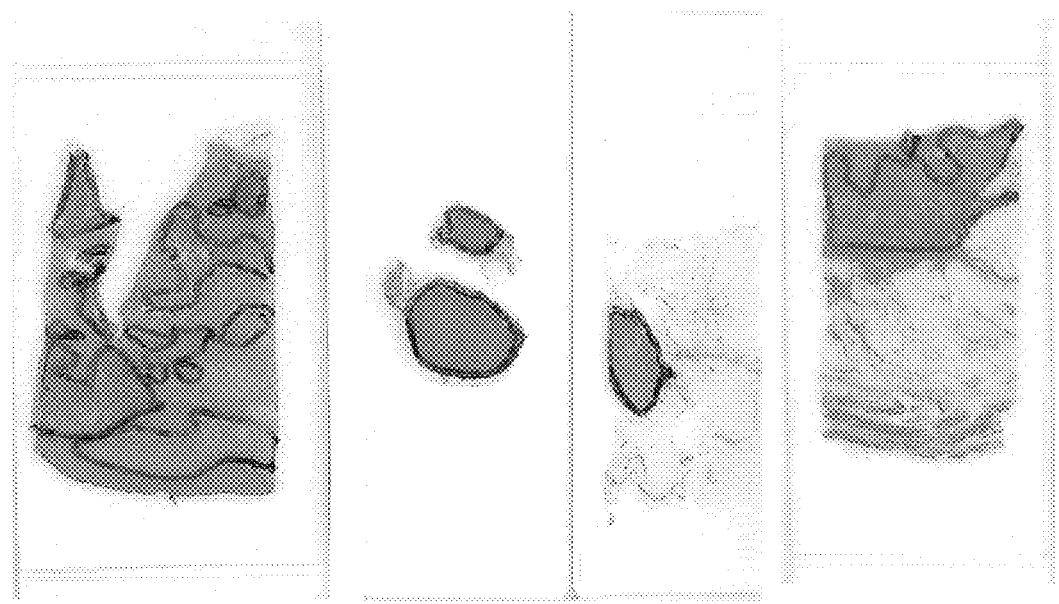
FIG. 4 shows examples of patient tumor samples in which a Board-certified pathologist has circled the tumor area.

FFPE breast cancer blocks were purchased from Asterand. Sections of 5 um in thickness were sliced with a microtome (LEICA) and placed on positively charged glass slides (VWR). Sections were air-dried for 30 min and then baked in an oven at 70° C. for 1.5 hr. All sample slides were stored at 4° C. for future assays. Previously sectioned breast tumors from clinical material were also used for these studies. Examples of H & E stained tumors on glass slides are shown in FIG. 4.

Example 5

Figure 5:
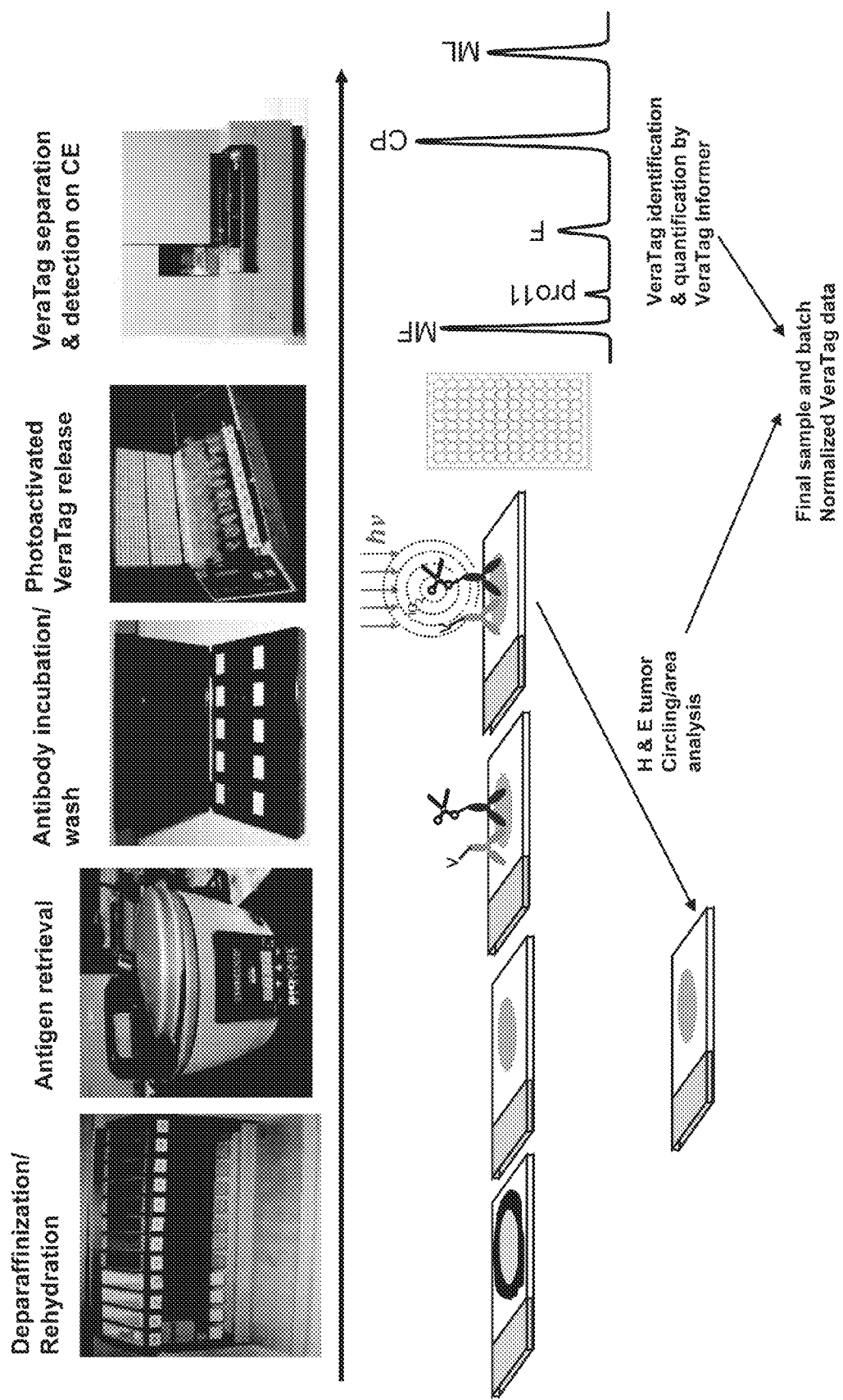
FIG. 5 shows the equipment used and the work flow of the HER3 VERATAG® assay. FFPE samples are first deparaffinized and rehydrated using a series of solvents (top panel 1). Antigen retrieval is accomplished using 1×DAKO (Lab Vision) in a pressure cooker (top panel 2). The samples are then rinsed with water and a hydrophobic pen is used to draw a circle around the sample, retaining reagents on the slide. The samples are then blocked and treated with a mixture of VERATAG®-conjugated Ab-6 (Lab Vision) and biotin-conjugated B9A11 (top panel 3). After incubation and washing, streptavidin-conjugated methylene blue reagent is added, incubated and washed, and then illumination buffer containing fluorescein and two capillary electrophoresis internal markers (MF and ML, marker first and last, respectively) is added. The bound VERATAG® is released using an LED array, which photoactivates cleavage of the VERATAG® (top panel 4). VERATAG® intermediates are reduced to a quantifiable form using sodium borohydride and the VERATAG® reporters are separated and detected using capillary electrophoresis (ABI3130 CE instrument, top panel 5).

Her-3 VERATAG® Assay in Formalin Fixed, Paraffin Embedded (FFPE) Cell Lines and Breast Tissue FFPE samples were deparaffinized/rehydrated using a series of solvents. Briefly, slides were sequentially soaked in xylene (2×, 5 min), 100% ethanol (2×, 5 min), 70% ethanol (2×, 5 min) and deionized water (2×, 5 min). Heat-induced epitope retrieval of the rehydrated samples was performed in a slide holder containing 250 mL of 1×DAKO (pH 9.0) (Lab Vision) using a pressure cooker (Biocare). After being cooled for 30 min at room temperature, the slides were rinsed once with deionized water. A hydrophobic circle was drawn on slide using a hydrophobic pen (Zymed) to retain reagents on slides. The samples were then blocked for 1 hr with blocking buffer that contains 1% mouse serum, 1.5% BSA and a cocktail of protease and phosphatase inhibitors (Roche) in 1×PBS. After removal of the blocking buffer with aspiration, a mixture of VERATAG®-conjugated (Ab-6: LabVision, 1 ug/mL) and biotin-conjugated (B9A1 1; Monogram proprietary, 2 ug/mL) antibodies prepared in blocking buffer was added and binding reactions were incubated overnight in a humidified chamber at 4° C. with shaking. The antibody mix was aspirated and samples were washed with wash buffer containing 0.25% TritonX-100 in 1×PBS and streptavidin-conjugated methylene blue at concentration of 2.5 ug/mL in 1×PBS was added. After 1 hr incubation at room temperature, the excess streptavidin-methylene blue reagent was aspirated and the samples were washed in wash buffer once followed by 3 changes of deionized water. Illumination buffer containing 3 pM fluorescein and two CE internal markers (MF and ML) in 0.01×PBS was added on sample sections. The bound VERATAG® was released at ~4° C. by photo-activated cleavage using an in-house LED array illuminator equipped with an electronic chiller block (Torrey Pine Scientific). After illumination, VERATAG® intermediates are reduced to a quantifiable form by the addition of sodium borohydride. The CE sample containing the released VERATAG® reporters was collected from above the tissue section on the slides and the released VERATAG® reporters in the CE samples were separated and detected on ABI3130 CE instrument (22-cm capillary array; Applied Biosystems) under CE injection condition of 6 kV and 50 sec at 30° C. The general workflow of the H3T assay in the clinical lab is illustrated in FIG. 5.

Example 6

CE Peak Analysis, Tumor Area Normalization and Batch Normalization

The identification and quantification of VERATAG® was carried out using VERATAG® Informer software (see, for example, United States publication number 2007-0203408-A1). To analyze the VERATAG® signals in a raw CE electropherogram, two CE internal markers, MF (first marker) and ML (last marker), were used to identify the VERATAG® peaks according to their electrophoretic mobility or migration time, t, relative to the two markers, i.e., [t(VERATAG®)-t(MF)]/[t(ML)-t(MF)]. The identified VERATAG® peaks were then quantified by peak area calculation for each VERATAG®. To correct for variability in VERATAG® recovery from the tissue section, and the run variability in CE injection efficiency and/or detection sensitivity across capillary array, fluorescein (3 pM) was included in the illumination buffer, and co-electrophoresed as an internal reference control in each sample run. The area of each VERATAG® peak is then reported as RFU or RPA by area normalization of the VERATAG® peak (VERATAG® peak area) to the internal fluorescein peak (fluorescein peak area/3 pM. This is quantified as RPA*IB vol/TA for variable tumor samples (=Relative peak area multiplied by the illumination buffer volume (IB) loaded onto sample section; divided by the tumor area in $mm^2$ (RPA*IB vol/TA=pmole/L*L/$mm^2$=pmole/$mm^2$). Specifically, the CE fluorescence signal intensity of a VERATAG® reporter, or the peak area ($PA_{VeraTag®}$), is given in relative fluorescent units (signal height) integrated across time (RFU-S/S). The relative peak area ($RPA_{VeraTag®}$ is measured by normalizing the VERATAG® peak area ($PA_{VeraTag®}$) with respect to the internal fluorescein standard of known concentration ($PA_F$), and is therefore proportional to the initial concentration of the analyte being measured. As the VERATAG®assay signal is a quantitative readout that scales with tumor content, accurate comparison of VERATAG® assay signals across clinical samples requires adjustment for differences in this parameter. Therefore, tumor content is measured on the sample VERATAG® assay signal data collection, and the tumor content is used to normalize the VERATAG® assay result. It should be noted that, if the tumor sample is either very small or very large the reaction volumes (i.e., volume of antibody, streptavidin-conjugated methylene blue and illumination buffer reagents) are adjusted, and this adjustment is reflected in the tumor content normalization. After adjusting VERATAG® peak areas for migration time, fluorescein, illumination buffer and tumor area, controls and samples are normalized by multiplying their adjusted peak area with the respective calculated Batch Normalization Factor (BNF). Each adjusted RPA value is multiplied by the respective BNF to obtain a normalized RPA value. Because this normalized RPA value is unitless by definition, its value is referred to in VERATAG® units. All reportable (not failed, and not saturated) normalized values for a given sample are averaged to determine a final value for that sample.

Various quality control checks have been developed to ensure data is of highest quality.
1. Fluorescein out of range. A sample trace with fluorescein out of range is failed. The fluorescein range is calculated by using the median of the adjusted fluorescein value+/− XX %. The XX % value, typically 20-40%, is adjustable and is associated with individual templates. Sample peaks are failed if the absolute height of the peak is >7000 units, referred to as a saturated peak.
2. RPA must be greater than or equal to 0.03.
3. If an undiluted converted peak sample is failed due to RPA <0.03, then all of the corresponding converted peak diluted samples are also failed.
4. At least 2 converted peak controls must have called values for converted peak batch normalization to proceed.
5. A sample or control with poor trace quality is failed.
6. If illumination buffer-only controls have contamination, samples may be failed if trace quality may be affected, e.g., if the contaminating peak overlaps with the released peak
7. A batch with poor batch normalization is failed.
8. A batch with an abnormally high batch normalization factor is failed.

For each sample, following the VERATAG® assay, an H&E (Hematoxylin and Eosin) staining and evaluation is performed to assure presence of tumor cells and to enable an estimation of tumor area. These slides are deparaffinized, hydrated, stained, and then dehydrated and mounted using standard procedures before microscopic examination.

Example 7

Optimization of Antibody Concentration to Increase Dynamic Range

Figure 6:
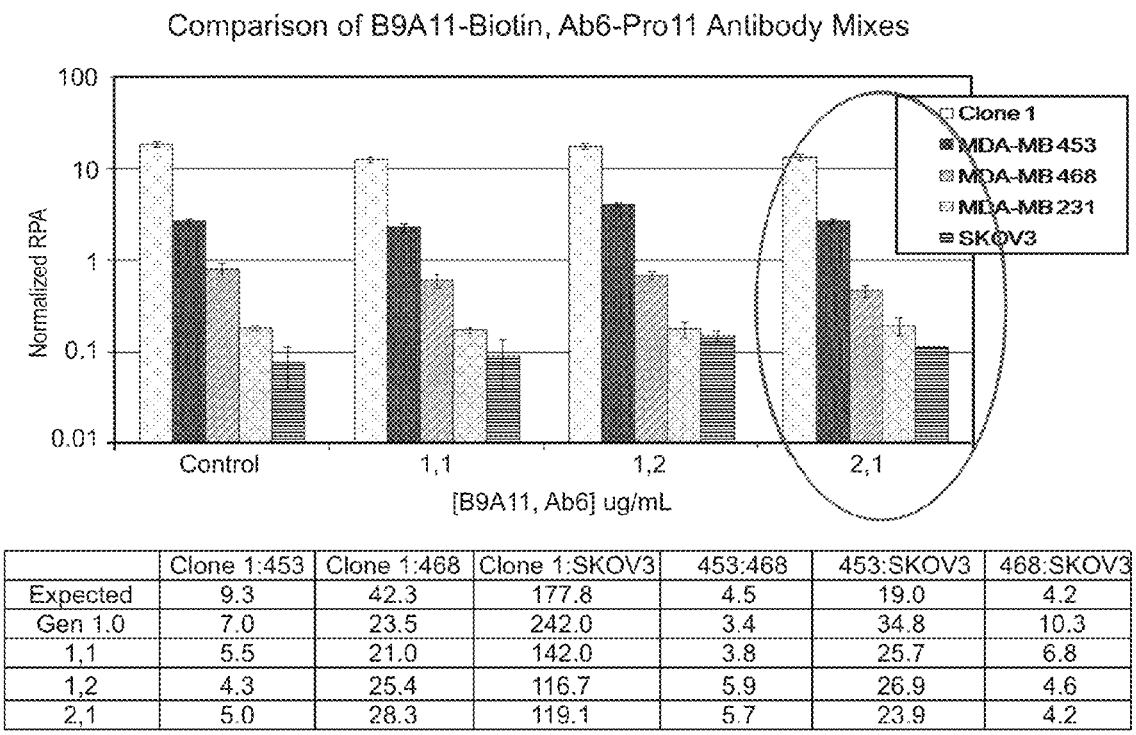
FIG. 6 shows the results from an experiment designed to identify the optimal antibody concentration for maximizing the dynamic range of the VERATAG® assay. Cell lines spanning the entire dynamic range of the assay were chosen: 293H3-Clone 1, MDA-MB-453, MDA-MB-468, MDA-MB-231 and SKOV3. The concentration of the antibodies B9A11-biotin and Ab-6 Pro-11 were varied (column 1 of the table) as follows: 1 mg/mL B9A11-biotin and 1 mg/mL Ab-6 Pro-11, 1 mg/mL B9A11-biotin and 2 mg/mL Ab-6 Pro-11 and 2 mg/mL B9A11-biotin and 1 mg/mL Ab-6 Pro-11, in rows 4, 5 and 6, respectively. The results for each cell line are shown in the bar graph. Expected fold changes for pair-wise comparisons were based on HER3 flow cytometry and ELISA results from the same cell line FFPE block preparation. An optimal concentration of 2 mg/mL B9A11-biotin and 1 mg/mL Ab-6 Pro-11 was chosen (circled) for best performance based on the accurate detection of HER3 as compared with the expected fold changes shown in row 2 of the table. The dynamic range shown here is approximately 2 logs.
Figure 7:
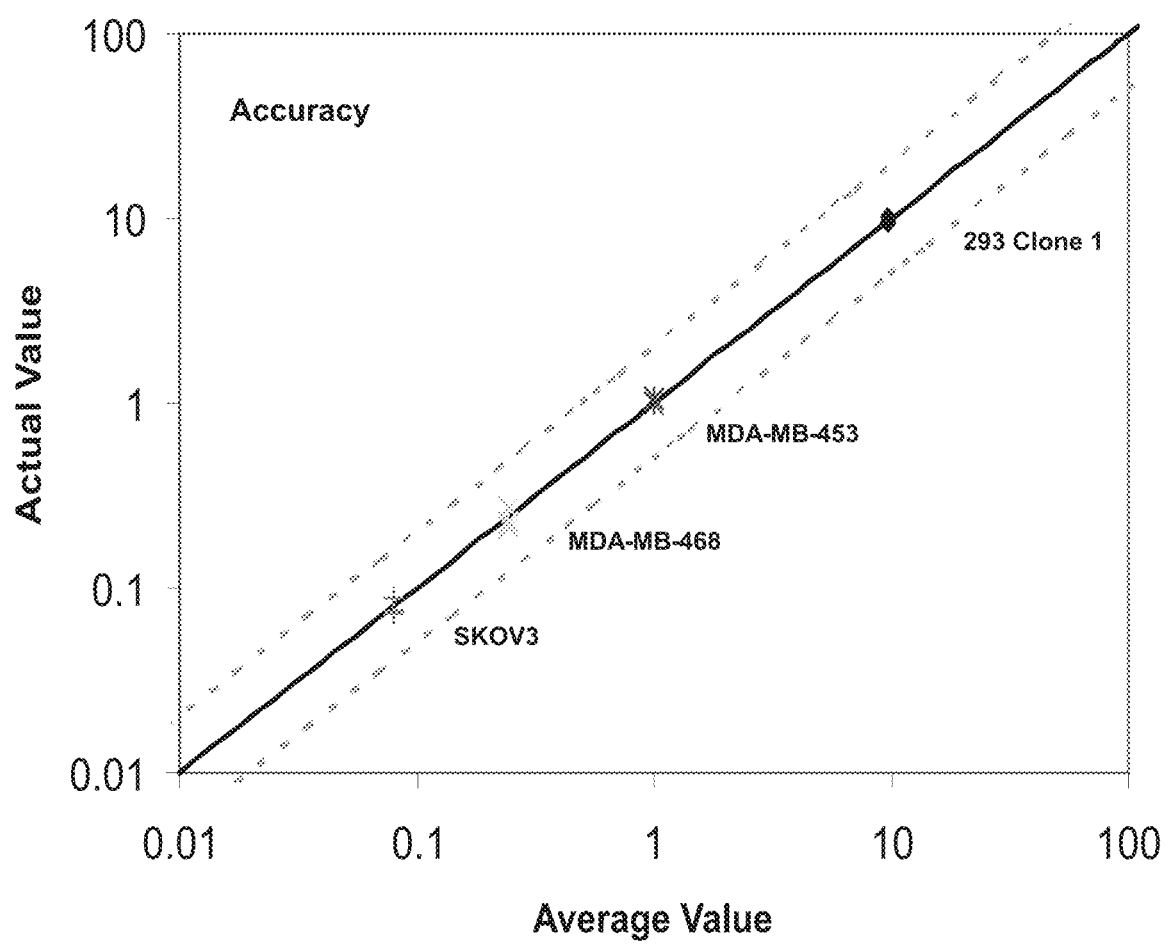
FIG. 7 shows the accuracy of the HER3 VERATAG® assay using three successful replicates from four well-characterized cell lines (293H3-Clone 1, MDA-MB-453, MDA-MB-468 and SKOV3). The VERATAG® measurements were compared with in-house generated flow cytometry and ELISA data. 100% of the results matched the in-house data from flow cytometry and ELISA in that 293H3-clone 1>MDA-MB-453>MDA-MB-468>SKOV3. No overlap was observed between signal levels for any of the four cell line samples.

Optimal concentrations of the Ab-6 and the B9A11 antibody were determined by varying the final concentrations in the VERATAG® HER3 total assay (as described above) on a cell line panel spanning the entire dynamic range of the assay (293H3-clone 1, MDA-MB-453, MDA-MB-468, and SKOV3). These results were then compared with expected fold changes based on HER3 flow cytometry and ELISA results from the same cell line FFPE block preparation. An optimal concentration of 2 mg/mL B9A11-biotin and 1 mg/mL of Ab-6 Pro-11 was selected for performance based on the accurate detection of HER3 as compared with the expected fold changes as compared to ELISA and flow cytometry in this same set of cell lines as shown in FIG. 6 where a 2:1 ratio of B9A11 to Ab-6 is circled.

Example 8

Accuracy of HER3 Total VERATAG® Assay

One batch of the HER3 total VERATAG® assay was performed using three successful replicates from four well-characterized cell lines (293H3-clone 1, MDA-MB-453, MDA-MB468, MDA-MB-231 and SKOV3) and then compared for accuracy of VERATAG® measurement with in-house generated flow cytometry and ELISA data. 100% of the results matched the in-house data from flow cytometry and ELISA in that 293H3-clone 1>MDA-MB-453>MDA-MB468> SKOV3. No overlap was observed between signal levels for any of the four cell line samples, i.e., each cell line separated completely. Internal datasets on HER3 Total levels were generated by both ELISA and flow cytometry. Results for the four accuracy cell lines are presented in FIG. 7. Results from HER3 flow cytometry were very similar to results from HER3 ELISA in that the same rank order preservation was demonstrated by using these cross-validating technologies.

Example 9

Sensitivity of HER3 Total VERATAG® Assay

Figure 8:
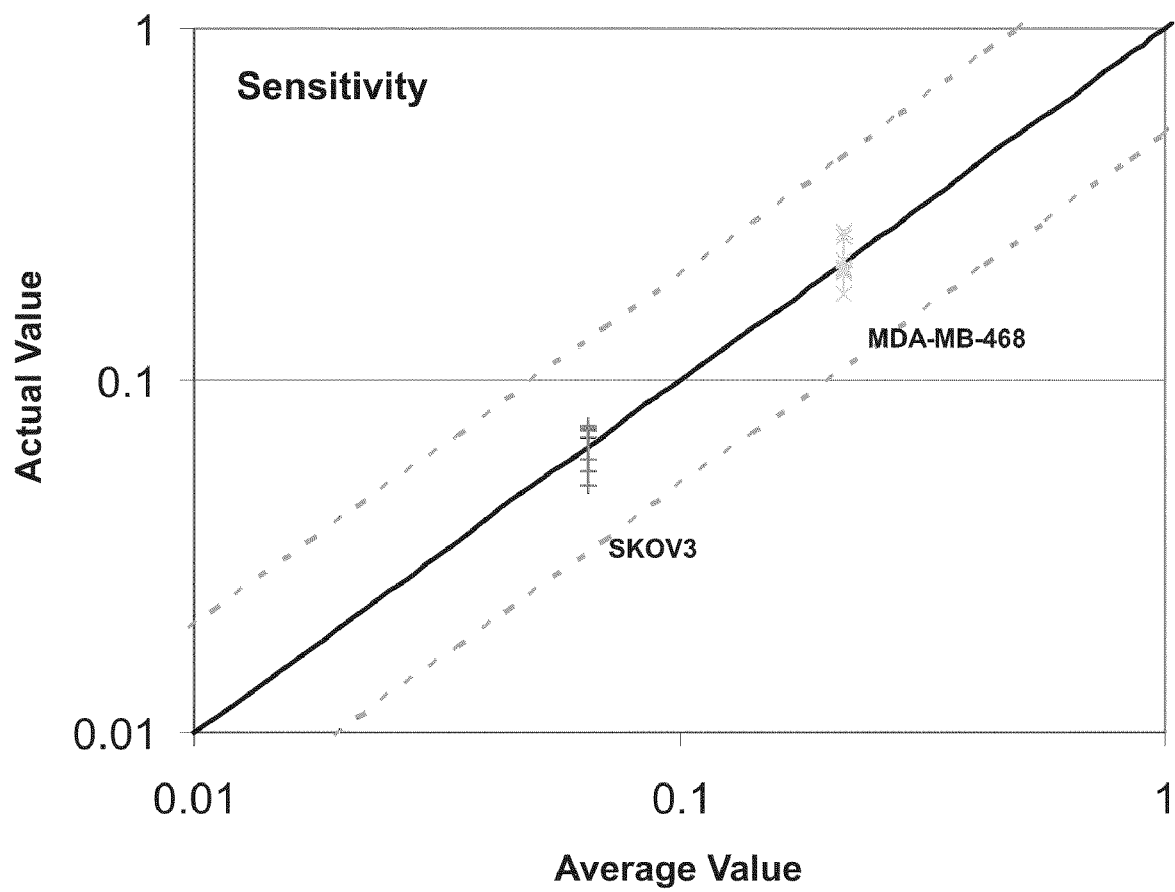
FIG. 8 demonstrates the sensitivity of the HER3 VERATAG® assay. One batch containing 8 replicates of the low HER3 expression control cell line, MDA-MB-468, was compared with 8 replicates of the low/negative HER3 expression control cell line, SKOV3, to determine sensitivity. All of the pairwise comparisons (64/64) between MDA-MB-468 and SKOV3 resulted in MDA-MB-468 having higher levels of HER3 than SKOV3.
Figure 9:
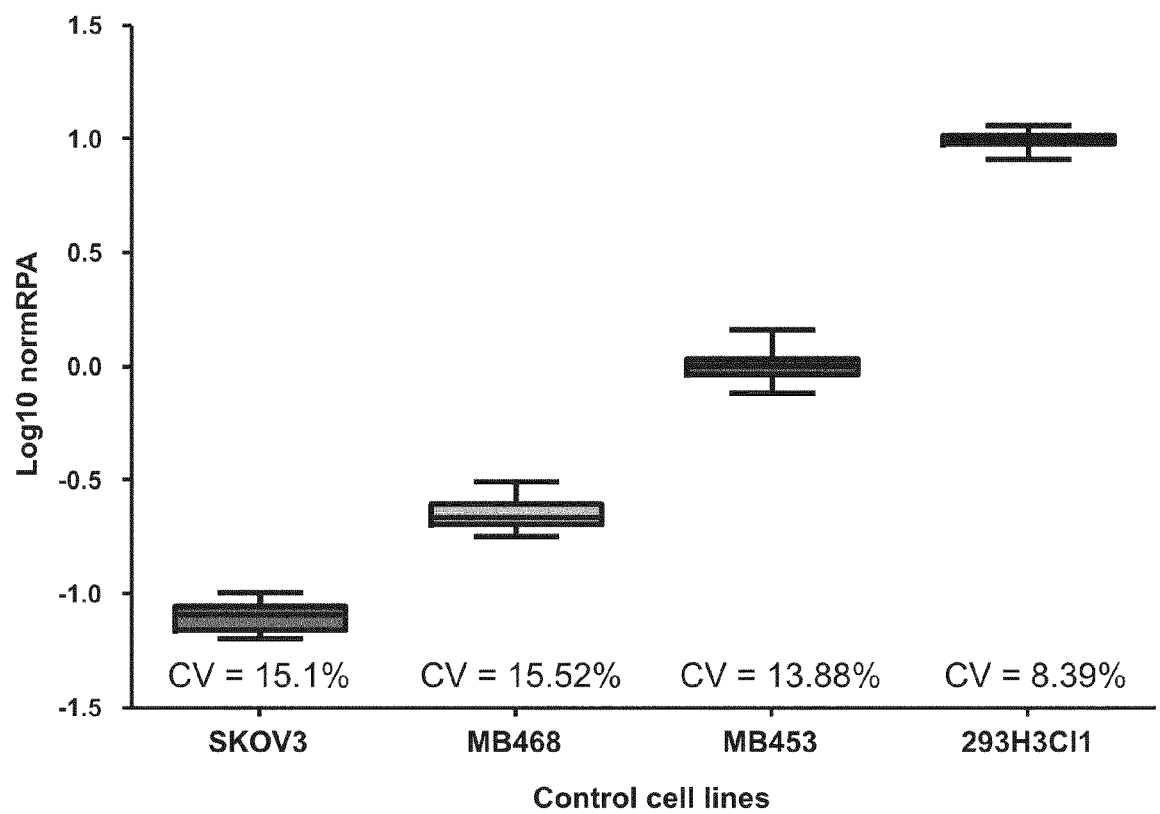
FIG. 9 shows the inter-assay reproducibility of the HER3 VERATAG® assay. Eight separate HER3 total VERATAG® assays were performed on the four well-characterized cell lines, 293H3-Clone 1, MDA-MB-453, MDA-MB-468 and SKOV3, using different CE illuminators, several operators and on different days over a 4 week period. Following batch normalization procedures, the data was compared across the 8 batches to ascertain reproducibility. The coefficient of variability across the dynamic range was between 8 and 15%. Values are represented as the $\text{Log}_{10}$ normRPA, which is the log of the normalized relative peak area/tumor area and then batch normalized using expected values.

The sensitivity of the HER3 total VERATAG® assay was determined by comparing one batch containing 8 replicates of the low HER3 expression control cell line, MDA-MB-468 with 8 replicates of the low/negative HER3 expression control cell line, SKOV3. The values for each replicate of MDA-MB-468 were compared with SKOV3 replicates by pairwise comparisons to determine sensitivity. 100% (64/64) of the pairwise comparisons between MDA-MB-468 and SKOV3 resulted in MDA-MB-468>SKOV3 (FIG. 8).

Example 10

Reproducibility of HER3 Total VERATAG® Assay

Inter-assay reproducibility was determined by performing 8 separate batches of the HER3 total VERATAG® assay as described above on 4 well characterized cell lines (293H3-clone 1, MDA-MB-453, MDA-MB-468 and SKOV3) using different instrumentation (CE, illuminators), several operators, and performing the assay over a 4 week period. Following batch normalization procedures, the data was compared across the 8 batches to determine reproducibility. The reproducibility across the dynamic range was between 8-15% (see FIG. 9).

Example 11

Precision of HER3 Total VERATAG® Assay

Figure 10:
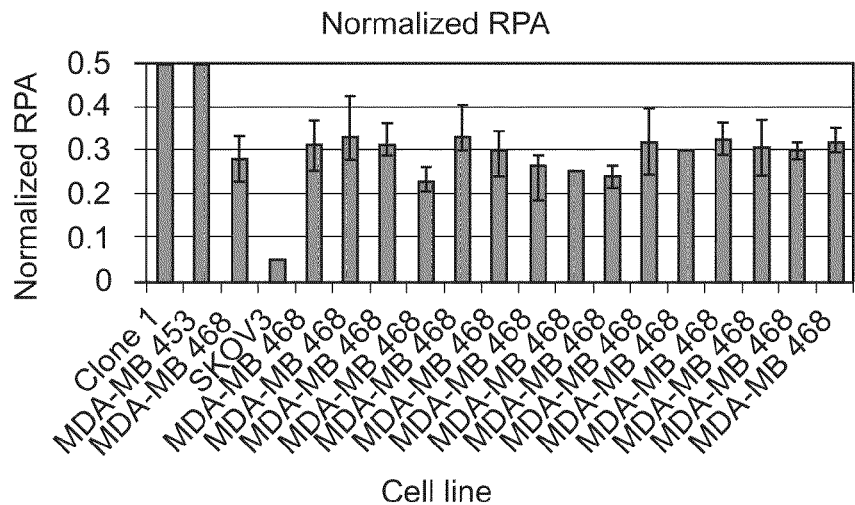
FIG. 10 shows the precision of the HER3 VERATAG® assay. The intra-assay reproducibility of the HER3 VERATAG® assay was demonstrated by comparing the performance of 15 replicates of each of the 3 control cell lines, 293H3-Clone 1, MDA-MB-453 and MDA-MB468. Pairwise comparisons were made of the 15 replicates in each batch to determine precision. 95% of the 293H3-Clone 1 data was within 1.2-fold and 95% of the MDA-MB-468 data is within 1.37-fold. The VERATAG® data (shown in normalized RPA) for the 15 replicates of each cell line is shown by the 15 bars on the right of each panel. The control data for the 3 cell lines expressing moderate to high levels of HER3 and a low/negative HER3 expressing cell line, SKOV3, are shown on the left of each panel.
Figure 10:
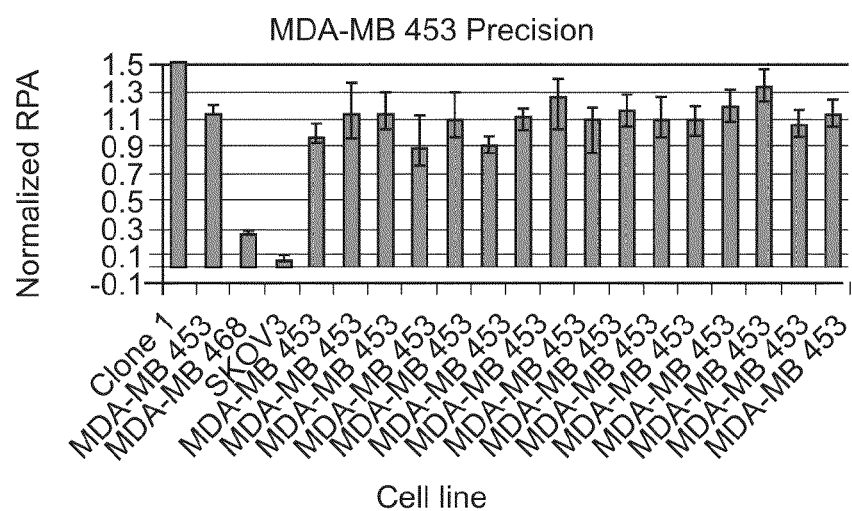
Figure 10:
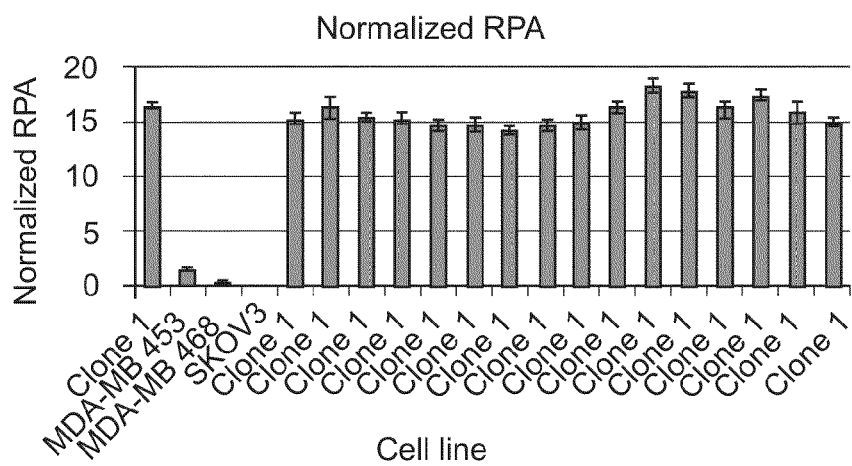

Intra-assay reproducibility was determined by performing 1 batch/cell line of the HER3 total VERATAG® assay and comparing the performance of 15 replicates of each of the 3 control cell lines (293H3-clone 1, MDA-MB-453, MDA-MB-468). Pairwise comparisons were made of the 15 replicates in each batch to determine precision of the assay. 95% of the 293H3-clone 1 data was within 1.2 fold, 100% of the MDA-MB-453 data was within 1.23-fold, and 95% of the MDA-MB-468 data is within 1.37-fold. Results are shown in FIG. 10.

Example 12

Linearity of the HER3 Total VERATAG® Assay

Figure 11:
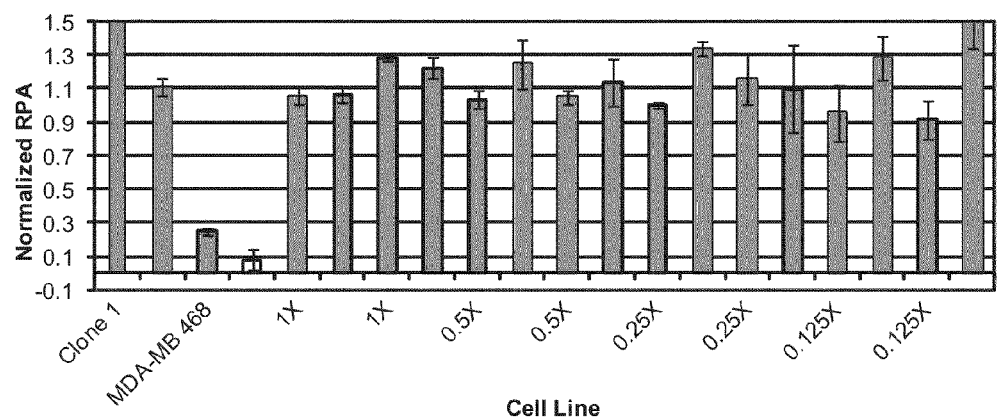
FIG. 11 shows the linearity of the HER3 VERATAG® assay using different sample sizes. Samples of diminishing size (1×, ½×, ¼×, ⅟₁₆×) from each of the 3 well-characterized cell lines, 293H3-Clone 1, MDA-MB-453 and MDA-MB-468, were tested in the VERATAG® assay and the data was compared in a pairwise manner to assess the linearity of the assay. The MDA-MB-453 cell line shows linearity down to approximately $\frac{1}{16}^{th}$ of the original sample size; MDA-MB-468 shows linearity down to approximately $\frac{1}{2}^{th}$ of the original sample size.
Figure 11:
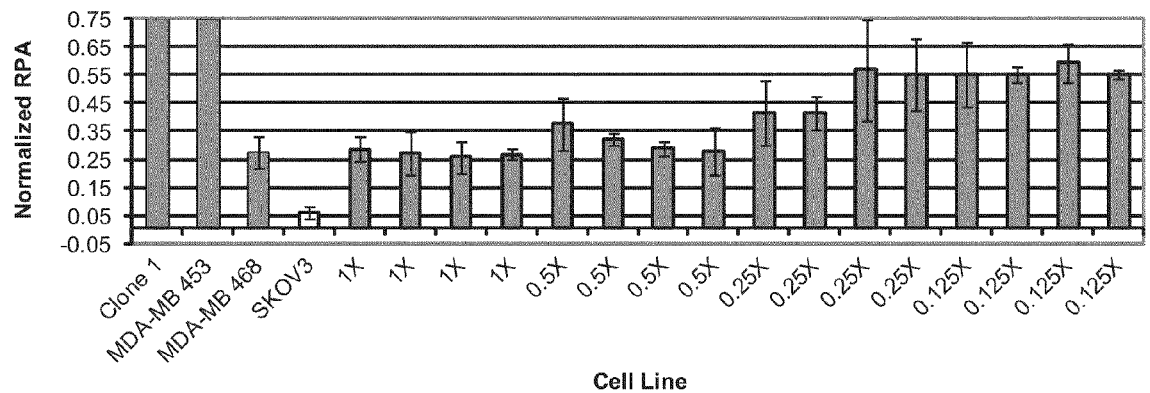

The linearity of the HER3 VERATAG® result was determined by taking well-characterized cell line controls 293H3-clone 1, MDA-MB-453, MDA-MB-468) and performing successive "cut-down" experiments to create FFPE sections with the following dimensions 1, ½, ¼, 1/16. These "cut-down" sections were then run in the H3T VERATAG® assay and the final section area normalized data was compared in a pairwise manner to understand the linearity of the assay with respect to section size (FIG. 11). MDA-MB-453 is linear down to approximately 1/16 of the original section size, while MDA-MB-468 is linear down to approximately should be ½ of the original section size. Results are shown in FIG. 11.

Example 13

Specificity of the HER3 Total VERATAG® Assay

Figure 12:
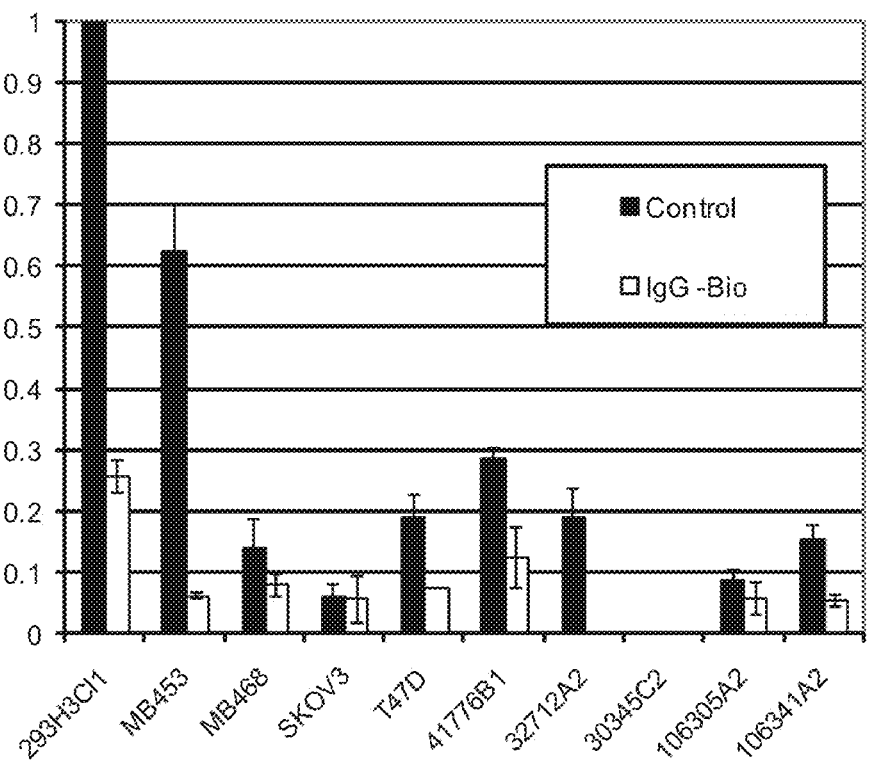
FIG. 12 shows the specificity of the HER3 VERATAG® assay as determined by isotype controls. Isotype control antibodies were tested in the VERATAG® assay format to ascertain the non-specific background of the assay. For the HER3 Ab-6-Pro11 antibody, the isotype control was IgG1-Pro11. For the HER3 B9A11-biotin antibody, the isotype control was IgG1-biotin. Signal derived using these isotype controls is not antigen-specific and therefore represents non-specific background. In the each panel, the VERATAG® results are shown for the normal assay format using the HER3 Ab6-Pro11 and B9A11-biotin antibodies in the bars labeled "control." In the left panel, the VERATAG® data is shown for the HER3 Ab6-Pro11 and IgG1-biotin antibodies in the bars labeled "IgG-bio." In the right panel, the VERATAG® data is shown for the HER3 B9A11-biotin and IgG1-Pro11 antibodies in the bars labeled "IgG-Pro11." Each antibody pairing was tested on an array of FFPE samples including standard cell line controls (293H3-Clone 1, MDA-MB-453, MDA-MB468, SKOV3 and T47D) as well as several tumor samples (41776B1, 32712A2, 30345C2, 106305A2, and 106341A2). Units are normalized RPA*IB/TA.
Figure 12:
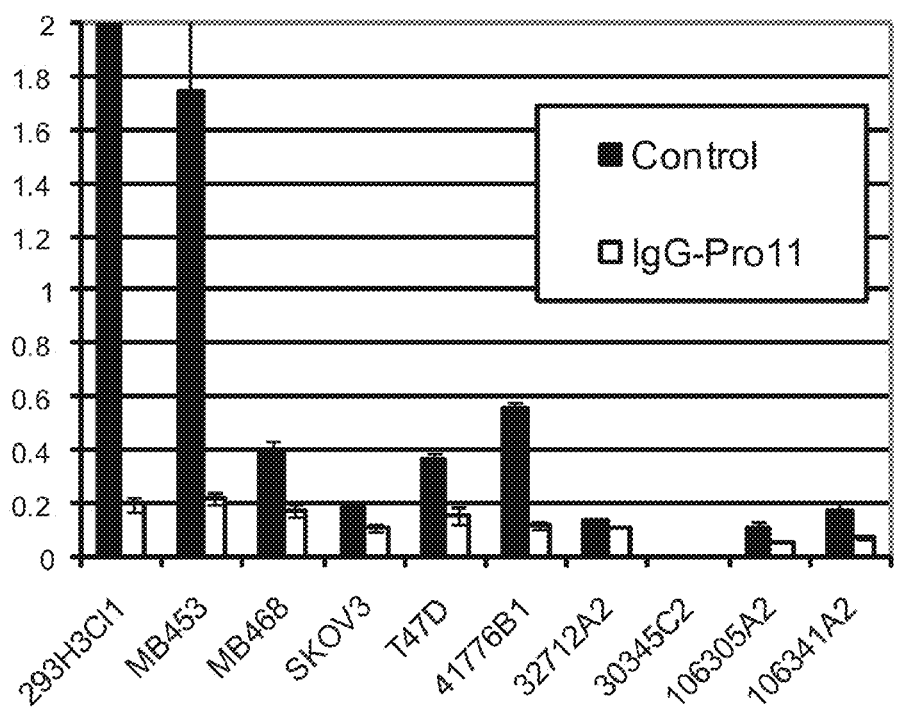

Patient-derived tumor samples and cell line controls were run using the VERATAG® HER3 Total Assay and using isotype control antibodies. For the HER3 Ab-6-Pro11, the matched isotype control was IgG1-Pro11. For the HER3 B9A11-biotin, the matched isotype control was also IgG1-biotin. Signal from these reactions is not antigen-specific, and would represent non-specific background. Samples were run in each of the following three formats and run within the same batch side by side:
Format 1: HER3 Ab6-Pro11/B9A11-biotin (normal format)
Format 2: HER2 Ab6-Pro11/IgG1-biotin
Format 3: IgG1-Pro11/B9A11-biotin Sample results from each IgG1 format (Format 2 and Format 3) were compared to the negative control, SKOV3, present in each batch (comparison parameter A). Samples results were also compared to the respective actual HER3 Total signals (Format 1). Results are shown in FIG. 12.

Example 14

Measurement of Clinical Breast Tumors and Dynamic Range

The study population comprised patients (n=105) that were prospectively observed during trastuzumab-based therapy at a single institution between 1999 and 2006 (the International Serum Her-2/neu Study Group trial). Only outpatients (ECOG PS 0-2, age>18 years, estimated life expectancy>12 weeks) with HER-2/neu-overexpressing (>10% of tumor cells IHC 3+ as determined by the HercepTest; DAKO Diagnostics, Austria) and/or ERBB2-amplified (with positive FISH testing mandatory in all IHC 2+ cases) MBC were included. In addition, patients were required to be trastuzumab-naïve and have bi-dimensionally measurable disease progressing within 4 weeks before initiation of treatment (excluding previously irradiated lesions). Samples from this study group trial were run in the H3T VERATAG® assay in eight separate batches. For each batch, CE peak analyses were performed, as well as tumor area analyses and the batch was normalized accordingly. Out of the 105 patient samples run in the assay, 85 samples had measurable H3T levels above the limit of detection, 8 patient samples had no detectable tumor, 1 sample demonstrated a fluorescein failure excluding the data, and finally there were 8 patient samples that were below the limit of detection of the assay and considered low/negative in H3T expression. The results are shown in FIG. 13.

Example 15

Determination of Optimal Cutoff for Trastuzumab Response

Figure 14:
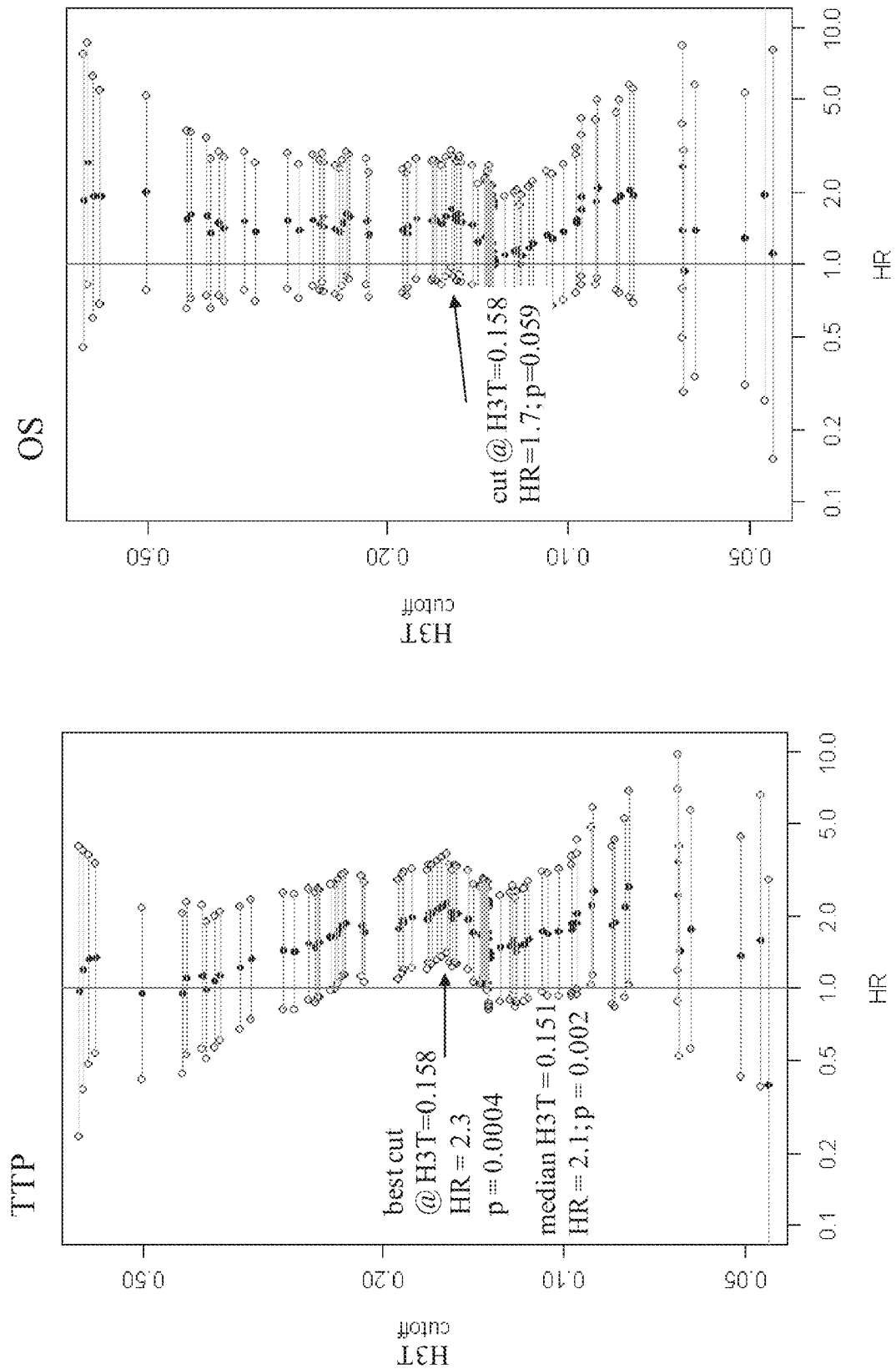
FIG. 14 shows the data from positional scanning analyses used to determine the optimal cut-off for trastuzumab (i.e., herceptin) response. In the left panel, patients above the statistically significant cut-off (see arrow) had an unfavorable time to progression (TTP) compared to patients below the cut-off (hazard ratio=2.3; p=0.0004). In the right panel, a significant cutoff could not be determined, but using the cut-off found for TTP, a trend for worse overall survival (OS) in patients above the cut-off (indicated by the arrow) was observed (hazard ratio=1.7; p=0.059).

Using positional scanning analysis an optimal cut-off was determined whereby patients above statistically significant cut-off had an unfavorable time to progression (TTP) compared to patients that were below this cut-off (FIG. 14). The cut-off was ~ the median of the results of the population tested (0.158, HR=2.3, p=0.0004. TTP was defined as the time from the initiation of trastuzumab-containing treatment to progression (SWOG) or censor, and OS was defined as the time from initiation of trastuzumab-containing treatment to death or censor. When looking at overall survival in this population of patients no significant cut-off could be determined, however there was a trend in OS using the 0.158 cut-off (HR=1.7; p=0.059).

Example 16

Kaplan Meier (KM) Analysis for TTP

Figure 15:
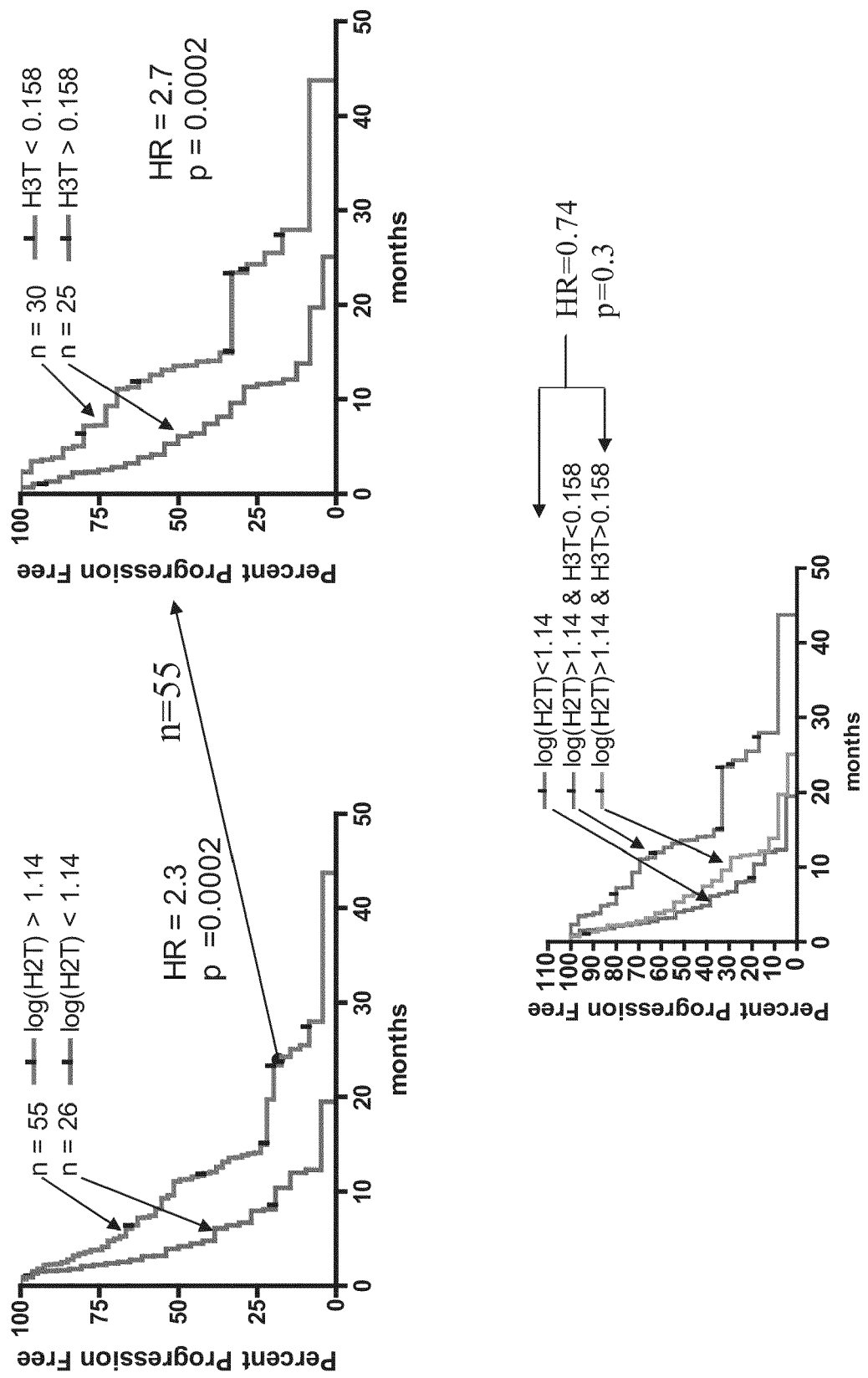
FIG. 15 shows Kaplan-Meier plots for a cohort of 82 trastuzumab-treated patients stratified first by total HER2 levels (H2T) and then further stratified by total HER3 levels (H3T). In the upper left panel, a Kaplan-Meier plot shows the percent of patients with progression-free survival (months) for two groups of patients subdivided (based on a previously reported cut-off) into HER2-normal and HER-2 over-expressing groups. The HER2 over-expressing group was then further subdivided, using the cut-off shown in FIG. 14, into two subgroups based on the level of HER3. The Kaplan-Meier plot of these two subgroups is shown in the upper right panel. The lower panel shows three sets of results from the upper panels: the normal HER2 group (log(H2T)<1.14), the HER2-high, HER3-low group (log(H2T)>1.14, H3T<0.158) and the HER2-high, HER3-high group (log(H2T)>1.14, H3T>0.158). Univariate Cox proportional hazards analyses examining the HER3-over-expressing subgroup identified H3T (high vs low) as the most significant predictor of time to progression (TTP; HR=2.98, p=0.0004).

A previously reported H2T cutoff (logH2T≧1.14) was used to sub-divide the patients into HER2-normal (N=26, median TTP=4.1 mos) and HER2-overexpressing (N=55, median TTP=11.1 mos, HR=0.43, p=0.0002) groups. In the HER2-overexpressing group, levels of H3T expression above an optimal cutoff (H3T>0.158; FIG. 14), as defined by a positional scanning predicted shorter median time to progression (N=25, median TTP=6.1 mos) compared with H3T expression below the cutoff (N=30, median TTP=13.1 mos, HR=2.7, p=0.0002). Univariate Cox proportional hazards analyses examining the HER2-overexpressing sub-group identified H3T (above vs below a particular cutoff) as the most significant predictor of TTP (HR=2.98, p=0.0004). These results are shown in FIG. 15.

Example 17

HER3 Total Expression by VERATAG® in Other Malignancies

Figure 16:
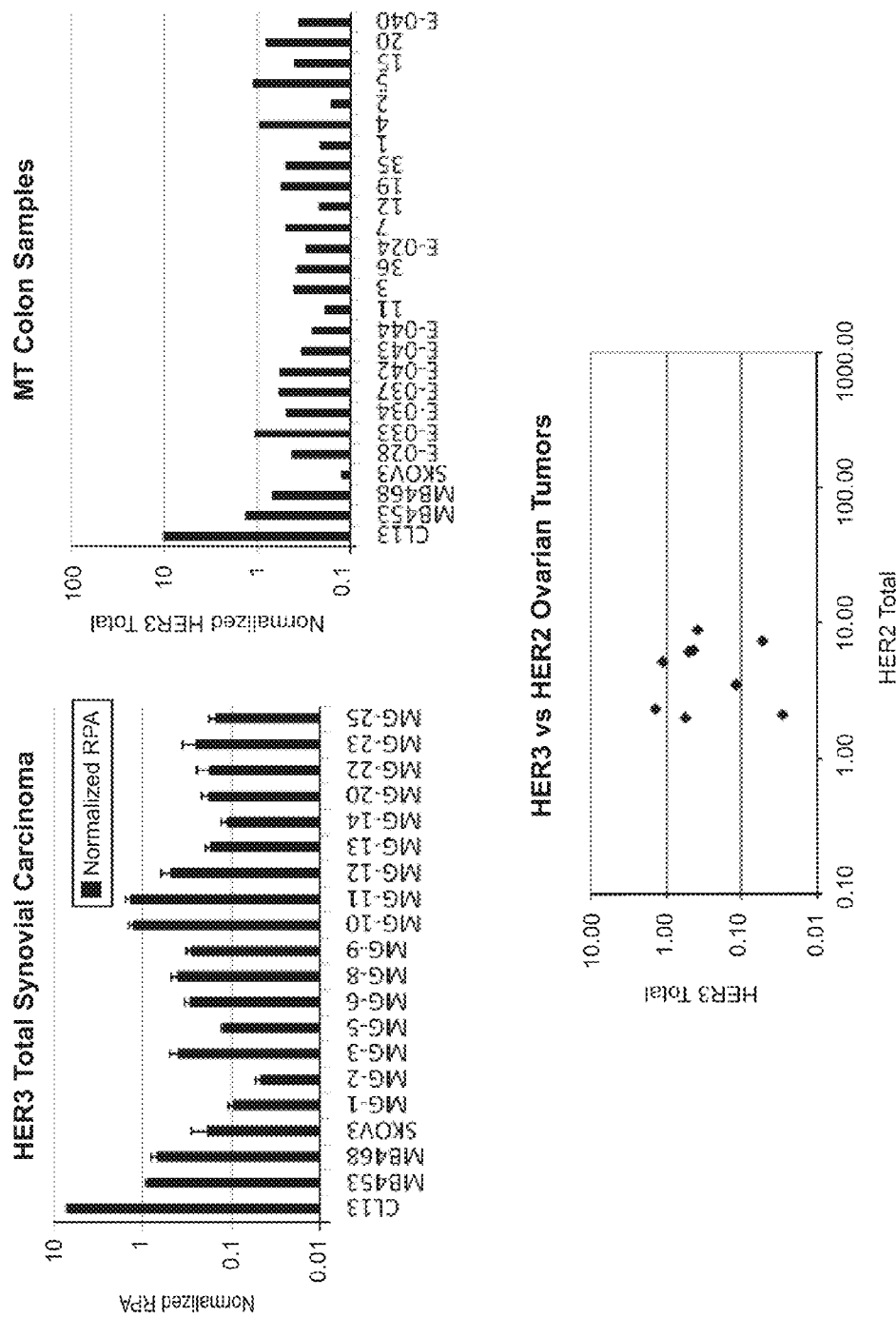
FIG. 16 shows the results of HER3 VERATAG® assays in synovial carcinoma, colon cancer and ovarian cancer. The top panel shows the results for a panel of synovial carcinoma samples. The 4 bars on the left are control samples (293H3-Clone 13, MDA-MB-453, MDAMB-468 and SKOV3, from left to right, respectively). The middle panel shows the results for a panel of colon cancer samples. The same control cell lines are used (shown in the left 4 bars). The lower panel shows results comparing HER2 expression to HER3 expression in a panel of ovarian tumor samples. Results are shown in normalized RPA units. The dynamic range of these tumor samples ranges from 0.5-1.5, depending on the cancer.

H3T VERATAG® assay was performed on a number of different malignancies other than breast cancer, including colon, ovarian, synovial tumors (FIG. 16). Similar dynamic ranges were observed for all of these cancers with the following rank order of range: Ovarian>Synovial Carcinoma>/=Colon. The dynamic range in these tumors ranges from 0.5-1.5 logs depending on the cancer.

Example 18

Figure 17:
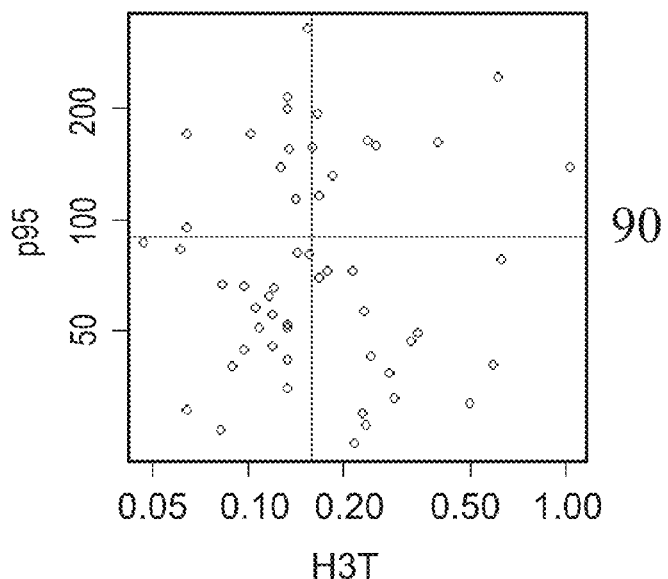
FIG. 17 shows that with the High HER2 (H2T) group (log 10H2T>1.25, or >13.8 on the linear scale), the ability to subgroup patients into different groups based on High or low p95 (p95>90 or <=90) and high or low HER3 (H3T) allows further stratification of clinical outcomes as measured by median TTP. Univariate KM analysis with the p95 and H3T subgroups combined, gives the results in the KM plots in this Figure. These data suggest that HER2-positive breast cancer patients as assessed by HERmark/VERATAG® (i.e., high H2T, i.e. log 10H2T>1.25, or >13.8 on the linear scale) can be classified into at least 4 sub-groups with different outcomes following trastuzumab treatment. In the KM, the group with low H3T (in generation 1 of the HER3 assay, H3T<0.158) and low p95 (p95<90) has a median TTP of 15.0 months, compared with 9.3 months for the group with low H3T (H3T<0.158) and high p95 (p95>90); compared with 6.4 months for the high H3T group (H3T>0.158 in generation 1 of the HER3 assay) and low p95 group, and compared with 3.2 months for the high H3T (H3T>0.158) and high p95 (p95>90). The trend for the differences among the groups is significant (p<0.0001).
Figure 17:
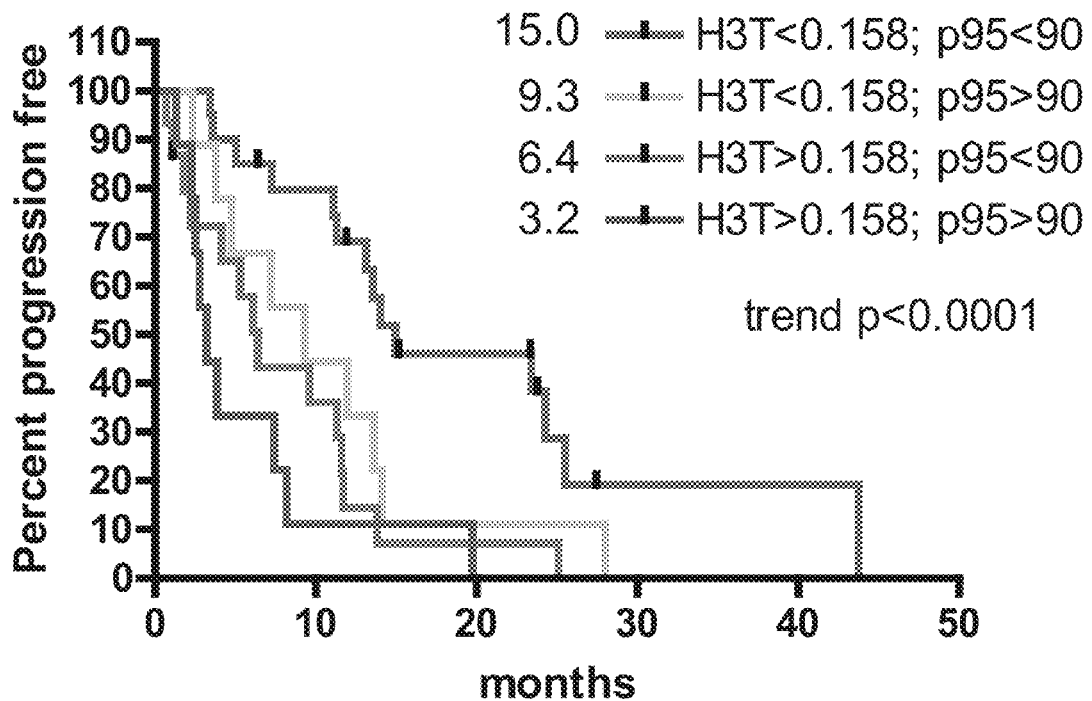

Measurement of HER3 in Conjunction with P95 and Correlation with Trastuzumab Response A previously reported P95 cut-off (U.S. patent application Ser. No. 12/629,037) was used to further stratify the HER-2 over-expressing patients described above after initial subdivision based on their level of HER3 to produce 4 patient subgroups as shown in FIG. 17. Patients with a low level of P95 and HER3, defined as below an optimal cut-off predicted by positional scanning, had a longer median time to progression (TTP=15.0 mos) than any of the other subgroups (logrank test for trend p<0.0001). Patients with a high level of P95 and HER3 had the shortest median time-to-progression (TTP=3.2 mos). The results are shown in FIG. 17

Example 19

Measurement of HER2, HER3 and P95 and Correlation with Trastuzumab Response

Figure 18:
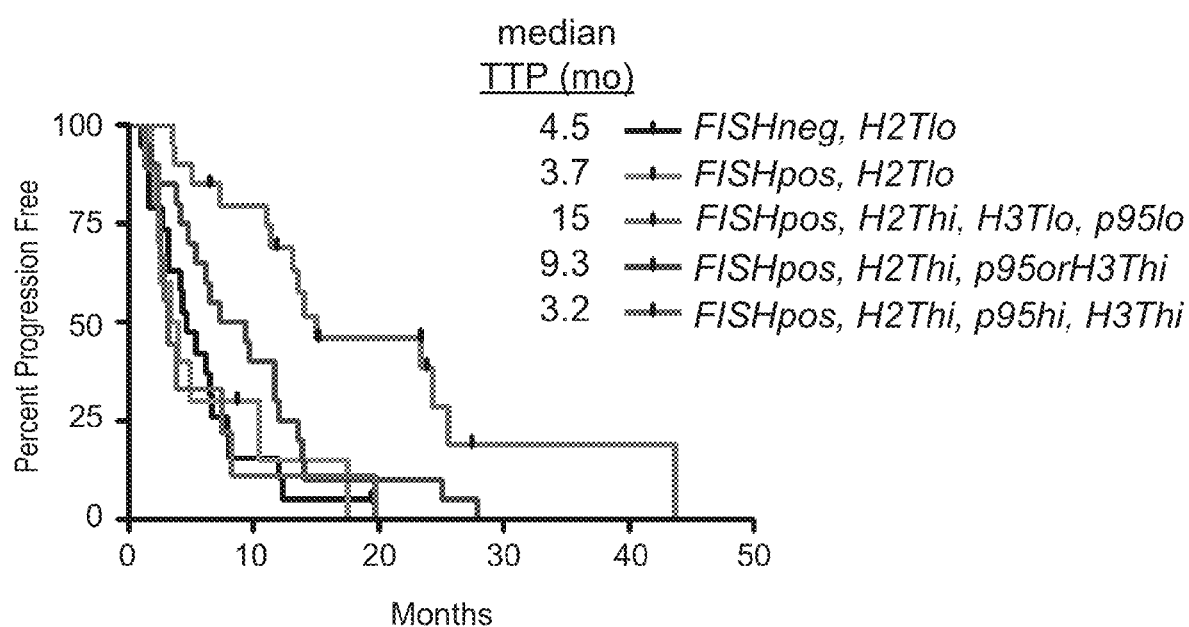
FIG. 18 shows Kaplan-Meier (KM) analyses comparing the percent progression free on the y axis over time on the x axis (time to progression, TTP) of various subgroups from the Lipton cohort, as defined by the combined VERATAG® measurements of HER2 total (H2T high or low), p95HER2 (p95 high or low), and HER3 Total (H3T) high (H3T>0.158, in Generation 1 of the H3T assay) or H3T low (H3T<=0.158 in Generation 1 of the assay). Cut-offs were identified by lowest p-value in a positional scanning analysis. H2T high=(log 10H2T>1.25 or on a linear scale, >13.8). Low H2T=log 10H2T<=1.25 or on a linear scale, <=13.8. p95 low=p95<=90 and p95 high=p95>90 (on a linear scale), and H3T hi>0.158 on a linear scale, and H3Tlo<=0.158 on a linear scale). KM analyses demonstrated that patients who were FISH positive, H2T high, p95 lo (low) and H3T lo (low) had a median TTP of 14.7 months, compared with the 4 other groups that did not fare as well. Three groups with nearly superimposable lines (i.e., FISHnegative/H2Tlo group—median TTP=4.5, FISH positive/H2Tlo(low) group-median TTP=3.7, and FISHpositive/H2Thi (high)/p95hi (high)/H3T hi (high)-median TTP=3.2) all had shorter median TTP than the group FISH positive/H2Thigh/p95lo/H3Tlo-median TTP=15). The group defined as FISH-positive/H2T hi(high)/ and p95 or H3Thigh had a median TTP=9.3, which was in between the group with the best median TTP (FISH positive/H2Thigh/p95lo/H3Tlo) and the 3 groups in red/blue and black. Thus, HERmark assay identified multiple subgroups of HER2 positive patients with varying clinical outcomes as measured by TTP on trastuzumab-based therapy. Neither the magnitude of HER2 over-expression nor the outcome for these subgroups was predictable by FISH/CEP17 copy number. HER2 FISH positive MBC patients with high p95 and/or high H3T may represent subsets of patients with de novo resistance to trastuzumab. While the applicants do not wish to be confined to any particular mechanistic theory, possible mechanisms that may account for the poor response to trastuzumab observed in these subgroups may include insufficient trastuzumab and/or lack of trastuzumab binding target (i.e., p95) and increased signaling via formation of heterodimers that are not completely suppressed by trastuzumab.

The patient population in Example 17 was subdivided by their level of HER2, P95 and HER3 as shown in FIG. 18.

Patients who are HER2-high, P95-low, and HER3-low, as defined by a positional scanning methodology, had a longer time to progression than patients who have a high level of HER2 and a high level of HER3 or P95 or both with the latter showing a similar time to progression as patients who have a low HER2 value as determined by the H2T VERATAG® assay. Within the subgroup with normal HER2 expression levels (H2Tlo) FISH-positive and FISH-negative groups experienced a similar time to progress.

All publications and other materials described herein are used to illuminate the invention or provide additional details respecting the practice and are incorporated by reference in their entirety.

What is claimed is:

1. A method for determining whether a subject with a cancer is likely to respond to treatment with a Her family targeted agent, for predicting a time course of disease during treatment with a Her family targeted agent, and/or for predicting the probability of a significant event in the time course of the subject's cancer during treatment with a Her family targeted agent, comprising:
   (a) obtaining a biological sample from of the subject's cancer;
   (b) measuring the amount of Her-3 in the biological sample using a Her-3 antibody that specifically binds to a polypeptide sequence set forth in one of SEQ ID NOs 1-8;
   (c) determining whether the amount of Her-3 in the subject's sample is above a Her-3 cutoff;
   (d) correlating the amount of Her-3 measured in the biological sample to at least one of determining the relative likelihood of whether a subject with a Her-2 positive cancer will respond to treatment with a Her-family targeted agent, predicting a time course of disease during treatment with a Her family targeted agent, and/or predicting a probability of a significant event in the time course of the subject's cancer during treatment with a Her family targeted agent; and
   (e) indicating that the subject is more likely to respond to the Her family targeted agent, more likely to have a long time course during treatment with a Her family targeted agent, and/or less likely to have a significant event during treatment with a Her family targeted agent if the amount of Her-3 in the biological sample is below the Her-3 cutoff as compared to if the Her-3 in the biological sample is above the Her-3 cutoff.

2. The method of claim 1, wherein the subject's cancer comprises breast cancer, colorectal cancer, ovarian cancer, non-small cell lung cancer or gastric cancer.

3. The method of claim 1, wherein the subject's cancer comprises metastatic breast cancer.

4. The method of claim 1, wherein the subject's cancer comprises early stage breast cancer.

5. The method of claim 1, wherein the Her family-targeted agent comprises a multi-target agent.

6. The method of claim 1, wherein the Her family-targeted agent comprises a dual kinase inhibitor or a bispecific antibody.

7. The method of claim 1, wherein the Her family-targeted agent comprises at least one of trastuzumab, lapatinib, pertuzumab, cetuximab, panitumumab, erlotinib or gefitinib.

8. The method of claim 1, wherein likeliness to respond, likeliness to have a long time course and/or likeliness to have a significant event is measured as at least one of overall survival rate, as time to progression, disease-free survival, progression-free survival, time to distant reoccurrence, hazard ratio and/or objective tumor response or clinical benefit using the RECIST criteria.

9. The method of claim 1, wherein measuring the amount of Her-3 in the biological sample comprises measuring at least one of total Her-3 protein, Her-3 homodimers or Her-3 heterodimers.

10. The method of claim 1, wherein the Her-family targeted agent comprises a single-target agent.

11. The method of claim 1, wherein the Her-family targeted agent comprises at least one of a Her-2 targeted agent or a Her-3 targeted agent.

12. The method of claim 1, wherein measuring the amount of Her-3 in the biological sample comprises the steps of:
  a) contacting the biological sample with the Her-3 antibody;
  b) contacting the Her-3 antibody with a tagged binding composition, wherein the tagged binding composition comprises a molecular tag attached thereto via a cleavable linkage, and wherein the tagged binding composition specifically binds to the Her-3 antibody;
  c) cleaving the cleavable linker of the tagged binding composition, thereby releasing the molecular tag; and
  d) quantitating the released molecular tag to determine the amount of Her-3 protein in the biological sample.

13. The method of claim 1, wherein measuring the amount of Her-3 in the biological sample comprises using immunohistochemistry to quantitate the amount of Her-3.

14. The method of claim 1, further comprising:
  (i) measuring the amount of p95 in the biological sample;
  (ii) determining whether the amount of p95 in the subject's sample is above a p95 cutoff
  (iii) correlating the amount of p95 measured in the biological sample to at least one of determining the relative likelihood of whether a subject with a Her-2 positive cancer will respond to treatment with a Her-family targeted agent, predicting a time course of disease during treatment with a Her family targeted agent, and/or predicting a probability of a significant event in the time course of the subject's cancer during treatment with a Her family targeted agent; and
  (iv) indicating that the subject is more likely to respond to the Her family targeted agent, more likely to have a long time course during treatment with a Her family targeted agent, and/or less likely to have a significant event during treatment with a Her family targeted agent if the amount of p95 in the biological sample is below the p95 cutoff than if the amount of Her-3 and/or p95 in the biological sample are above their respective cutoffs.

15. The method of claim 14, wherein measuring the amount of p95 in the biological sample comprises quantitation of p95 gene expression levels.

16. The method of claim 14, wherein measuring the amount of p95 in the biological sample comprises measuring the amount of total p95 protein.

17. The method of claim 14, wherein measuring the amount of p95 in the biological sample comprises the steps of:
  a) contacting the biological sample with a p95 binding composition that specifically binds to p95 protein;
  b) contacting the p95 binding composition with a tagged binding composition, wherein the tagged binding composition comprises a molecular tag attached thereto via a cleavable linkage, and wherein the tagged binding composition specifically binds to the p95 binding composition;
  c) cleaving the cleavable linker of the tagged binding composition, thereby releasing the molecular tag; and
  d) quantitating the released molecular tag to determine the amount of p95 protein in the biological sample.

18. The method of claim 1, wherein measuring the amount of Her-3 in the biological sample comprises the steps of:
  a) contacting the biological sample with a tagged Her-3 binding composition that specifically binds to Her-3 protein, wherein the tagged Her-3 binding composition comprises the Her-3 antibody and a molecular tag attached thereto via a cleavable linkage;
  b) contacting the biological sample with a cleaving agent;
  c) cleaving the cleavable linkage of the tagged Her-3 binding composition, thereby releasing the molecular tag; and
  d) quantitating the released molecular tag to determine the amount of Her-3 protein in the biological sample.

19. The method of claim 18, wherein measuring the amount of Her-2 in the biological sample comprises measuring at least one of total Her-2 protein or Her-2 homodimers.

20. The method of claim 1, wherein the Her 3 antibody is at least one of a monoclonal antibody comprising (a) a light chain variable region comprising CDR1, CDR2 and CDR3 having sequences as set forth in SEQ ID NOs: 13, 14 and 15, respectively, and (b) a heavy chain variable region comprising CDR1, CDR2 and CDR3 having sequences as set forth in SEQ ID NOs: 16, 17 and 18, respectively; or a monoclonal antibody comprising (a) a light chain variable region comprising CDR1, CDR2 and CDR3 having sequences as set forth in SEQ ID NOs: 19, 20 and 21, respectively, and (b) a heavy chain variable region comprising CDR1, CDR2 and CDR3 having sequences as set forth in SEQ ID NOs: 22, 23 and 24, respectively.

21. The method of claim 1, wherein the Her 3 antibody is at least one of an antibody comprising an amino acid sequence set forth in SEQ ID NOs: 9 and 11 for the light and heavy chains, respectively, or SEQ ID NOs: 10 and 12 forth the light and heavy chains, respectively.

22. The method of claim 1, wherein the subject's cancer has been characterized as Her-2 positive based on the level of Her-2 in the biological sample being above a Her-2 cutoff.

23. The method of claim 22, wherein measuring the amount of Her-2 in the biological sample comprises measuring at least one of total Her-2 protein or Her-2 homodimers.

24. The method of claim 22, wherein characterization of the subject's cancer as Her-2 positive comprises the steps of:
  a) contacting the biological sample with a Her-2 binding composition that specifically binds to Her-2 protein;
  b) contacting the Her-2 binding composition with a tagged binding composition, wherein the tagged binding composition comprises a molecular tag attached thereto via a cleavable linkage, and wherein the tagged binding composition specifically binds to the Her-2 binding composition;
  c) cleaving the cleavable linker of the tagged binding composition, thereby releasing the molecular tag; and
  d) quantitating the released molecular tag to determine the amount of Her-2 protein in the biological sample.

25. The method of claim 22, wherein the method by which the subject's cancer has been characterized as Her-2 positive comprises quantitation of Her-2 gene expression levels or Her-2 gene copy number.

26. The method of claim 22, wherein the method by which the subject's cancer has been characterized as Her-2 positive comprises using in situ hybridization, immunohistochemistry, quantitative mRNA analysis or a hybridization array to quantitate the amount of Her-2 in the biological sample.

27. The method of claim 22, wherein characterization of the subject's cancer as Her-2 positive comprises the steps of:
   a) contacting the biological sample with a tagged Her-2 binding composition that specifically binds to Her-2 protein, wherein the tagged Her-2 binding composition comprises a molecular tag attached thereto via a cleavable linkage;
   b) contacting the biological sample with a cleaving agent;
   c) cleaving the cleavable linkage of the tagged Her-2 binding composition, thereby releasing the molecular tag; and
   d) quantitating the released molecular tag to determine the amount of Her-2 protein in the biological sample.

28. A method for determining whether a subject with a cancer is likely to respond to treatment with a Her family targeted agent, for predicting a time course of disease during treatment with a Her family targeted agent, and/or for predicting the probability of a significant event in the time course of the subject's cancer during treatment with a Her family targeted agent, comprising:
   (a) obtaining a biological sample from the subject's cancer;
   (b) measuring the amount of Her-3 and p95 in the biological sample, wherein the amount of Her-3 antibody that specifically binds to a polypeptide sequence set forth in one of SEQ ID NOs 1-8;
   (c) determining whether the amount of Her-3 in the subject's sample is above a Her-3 cutoff and whether the p95 in the subject's sample is above a p95 cutoff; and
   (d) correlating the amount of Her-3 and p95 measured in the biological sample to at least one of determining the relative likelihood of whether a subject with a Her-2 positive cancer will respond to treatment with a Her-family targeted agent, predicting a time course of disease during treatment with a Her family targeted agent, and/or predicting a probability of a significant event in the time course of the subject's cancer during treatment with a Her family targeted agent; and
   (e) indicating that the subject is more likely to respond to the Her family targeted agent, more likely to have a long time course during treatment with a Her family targeted agent, and/or less likely to have a significant event during treatment with a Her family targeted agent if the amount of Her-3 in the biological sample is below the Her-3 cutoff than if the Her-3 and/or p95 in the biological sample are above their respective cutoffs.

29. The method of claim 28, wherein measuring the amount of Her-3 in the biological sample comprises measuring at least one of total Her-3 protein, Her-3 homodimers or Her-3 heterodimers.

30. The method of claim 28, wherein measuring the amount of p95 in the biological sample comprises measuring the amount of total p95 protein.

31. The method of claim 28, wherein the subject's cancer comprises breast cancer, colorectal cancer, ovarian cancer, non-small cell lung cancer or gastric cancer.

32. The method of claim 28, wherein the subject's cancer comprises-metastatic breast cancer.

33. The method of claim 28, wherein the subject's cancer comprises early stage breast cancer.

34. The method of claim 28, wherein the Her-family targeted agent comprises at least one of a Her-2 targeted agent or a Her-3 targeted agent.

35. The method of claim 28, wherein the Her-family targeted agent comprises a single-target agent.

36. The method of claim 28, wherein the Her family-targeted agent comprises a multi-target agent.

37. The method of claim 28, wherein the Her family-targeted agent comprises a dual kinase inhibitor or a bispecific antibody.

38. The method of claim 28, wherein the Her family-targeted agent comprises at least one of trastuzumab, lapatinib, pertuzumab, cetuximab, panitumumab, erlotinib or gefitinib.

39. The method of claim 28, wherein likeliness to respond, likeliness to have a long time course and/or likeliness to have a significant event is measured as at least one of overall survival rate, time to progression, disease-free survival, progression-free survival, time to distant reoccurrence, hazard ratio and/or objective tumor response or clinical benefit using the RECIST criteria.

40. The method of claim 28, wherein measuring the amount of Her-3 in the biological sample comprises the steps of:
   a) contacting the biological sample with the Her-3 antibody;
   b) contacting the Her-3 antibody with a tagged binding composition, wherein the tagged binding composition comprises a molecular tag attached thereto via a cleavable linkage, and wherein the tagged binding composition specifically binds to the Her-3 antibody;
   c) cleaving the cleavable linker of the tagged binding composition, thereby releasing the molecular tag; and
   d) quantitating the released molecular tag to determine the amount of Her-3 protein in the biological sample.

41. The method of claim 28, wherein measuring the amount of Her-3 in the biological sample comprises using immunohistochemistry, to quantitate the amount of Her-2 in the biological sample.

42. The method of claim 28, wherein measuring the amount of p95 in the biological sample comprises quantitation of p95 gene expression levels.

43. The method of claim 28, wherein measuring the amount of p95 in the biological sample comprises the steps of:
   a) contacting the biological sample with p95 binding composition that specifically binds to p95 protein;
   b) contacting the p95 binding composition with a tagged binding composition, wherein the tagged binding composition comprises a molecular tag attached thereto via a cleavable linkage, and wherein the tagged binding composition specifically binds to the p95 binding composition;
   c) cleaving the cleavable linker of the tagged binding composition, thereby releasing the molecular tag; and
   d) quantitating the released molecular tag to determine the amount of p95 protein in the biological sample.

44. The method of claim 28, wherein measuring the amount of Her-3 in the biological sample comprises the steps of:
   a) contacting the biological sample with a tagged Her-3 binding composition that specifically binds to Her-3 protein, wherein the tagged Her-3 binding composition comprises the Her-3 antibody and a molecular tag attached thereto via a cleavable linkage;

b) contacting the biological sample with a cleaving agent;
c) cleaving the cleavable linkage of the tagged Her-3 binding composition, thereby releasing the molecular tag; and
d) quantitating the released molecular tag to determine the amount of Her-3 protein in the biological sample.

45. The method of claim 28, wherein the Her 3 antibody is at least one of a monoclonal antibody comprising (a) a light chain variable region comprising CDR1, CDR2 and CDR3 having sequences as set forth in SEQ ID NOs: 13, 14 and 15, respectively, and (b) a heavy chain variable region comprising CDR1, CDR2 and CDR3 having sequences as set forth in SEQ ID NOs: 16, 17 and 18, respectively; or a monoclonal antibody comprising (a) a light chain variable region comprising CDR1, CDR2 and CDR3 having sequences as set forth in SEQ ID NOs: 19, 20 and 21, respectively, and (b) a heavy chain variable region comprising CDR1, CDR2 and CDR3 having sequences as set forth in SEQ ID NOs: 22, 23 and 24, respectively.

46. The method of claim 28, wherein the Her 3 antibody is at least one of an antibody comprising an amino acid sequence set forth in SEQ ID NOs: 9 and 11 for the light and heavy chains, respectively, or SEQ ID NOs: 10 and 12 forth the light and heavy chains, respectively.

47. The method of claim 28, wherein the subject's cancer has been characterized as Her-2 positive based on the level of Her-2 in the biological sample being above a Her-2 cutoff.

48. The method of claim 47, wherein characterization of the subject's cancer as Her-2 positive comprises the steps of:
a) contacting the biological sample with a Her-2 binding composition that specifically binds to Her-2 protein;
b) contacting the Her-2 binding composition with a tagged binding composition, wherein the tagged binding composition comprises a molecular tag attached thereto via a cleavable linkage, and wherein the tagged binding composition specifically binds to the Her-2 binding composition;
c) cleaving the cleavable linker of the tagged binding composition, thereby releasing the molecular tag; and
d) quantitating the released molecular tag to determine the amount of Her-2 protein in the biological sample.

49. The method of claim 47, wherein characterization of the subject's cancer as Her-2 positive comprises the steps of:
a) contacting the biological sample with a tagged Her-2 binding composition that specifically binds to Her-2 protein, wherein the tagged Her-2 binding composition comprises a molecular tag attached thereto via a cleavable linkage;
b) contacting the biological sample with a cleaving agent;
c) cleaving the cleavable linkage of the tagged Her-2 binding composition, thereby releasing the molecular tag; and
d) quantitating the released molecular tag to determine the amount of Her-2 protein in the biological sample.

50. The method of claim 47, wherein the method by which the subject's cancer has been characterized as Her-2 positive comprises quantitation of Her-2 gene expression levels or Her-2 gene copy number.

51. The method of claim 47, wherein the method by which the subject's cancer has been characterized as Her-2 positive comprises using in situ hybridization, quantitative mRNA analysis, a hybridization array, immunohistochemistry to quantitate the amount of Her-2 in the biological sample.

* * * * *

UNITED STATES PATENT AND TRADEMARK OFFICE
CERTIFICATE OF CORRECTION

| | | |
|---|---|---|
| PATENT NO. | : 8,349,574 B2 | Page 1 of 1 |
| APPLICATION NO. | : 12/688798 | |
| DATED | : January 8, 2013 | |
| INVENTOR(S) | : Michael Bates et al. | |

It is certified that error appears in the above-identified patent and that said Letters Patent is hereby corrected as shown below:

On the Title Page,
References Cited Page 8 should read: Larson, J.S. et al., "Analytical validation of a highly sensitive, accurate, and reproducible assay (HERmark) for the measurement of HER2 total protein and HER2 homodimers in FFPE breast cancer tumor specimens," Pathol. Res. Intl, 2010: Article ID 814176 (2010) (pub. online Jun. 28, 2010).

In the Specifications

Column 12, Line 13 Insert -- - -- between "MB" and "468".

Column 12, Line 52 Insert -- - -- between "MB" and "468".

Column 13, Line 34 Insert -- - -- between "MDA" and "MB".

Column 46, Line 14 Insert -- - -- between "MB" and "468".

Column 46, Line 19 Insert -- - -- between "MB" and "468".

In the Claims

Column 62, Line 45 Insert -- set -- between "12" and "forth".

Column 65, Line 22 Insert -- set -- between "12" and "forth".

Signed and Sealed this
Fourteenth Day of May, 2013

Teresa Stanek Rea
*Acting Director of the United States Patent and Trademark Office*